(12) United States Patent
Uppalapati et al.

(10) Patent No.: US 8,138,392 B2
(45) Date of Patent: Mar. 20, 2012

(54) DISEASE RESISTANT PLANTS

(75) Inventors: Srinivasa Rao Uppalapati, Lone Grove, OK (US); Kirankumar Mysore, Admore, OK (US); Wensheng Li, St. Louis, MO (US); Lloyd Sumner, Ardmore, OK (US); Richard A. Dixon, Ardmore, OK (US)

(73) Assignee: The Samuel Roberts Noble Foundation, Inc., Ardmore, OK (US)

( * ) Notice: Subject to any disclaimer, the term of this patent is extended or adjusted under 35 U.S.C. 154(b) by 221 days.

(21) Appl. No.: 12/502,968

(22) Filed: Jul. 14, 2009

(65) Prior Publication Data

US 2010/0017913 A1    Jan. 21, 2010

Related U.S. Application Data

(60) Provisional application No. 61/080,633, filed on Jul. 14, 2008.

(51) Int. Cl.
C12N 15/82 (2006.01)
C12N 15/10 (2006.01)
C12N 15/63 (2006.01)
C12N 15/00 (2006.01)
A01H 5/00 (2006.01)

(52) U.S. Cl. ........ 800/285; 800/286; 800/284; 800/278; 800/295; 800/298; 435/320.1; 435/468; 435/410; 536/23.1; 536/23.2; 536/23.6; 536/24.5

(58) Field of Classification Search .................. None
See application file for complete search history.

(56) References Cited

U.S. PATENT DOCUMENTS

2005/0260754 A1* 11/2005 Kock et al. .................... 435/455

FOREIGN PATENT DOCUMENTS

WO     WO 01/73090    10/2001

OTHER PUBLICATIONS

Guo et al 2001 Transgenic Research 10:457-464, provided by Applicant.*
A Compendium of Alfalfa Diseases, American Phytopathological Society, Graham et al. (Eds), St. Paul, MN, 1979.
Benedito et al., "A gene expression atlas of the model legume, *Medicago truncatula*," *Plant J.*, 55:504-513, 2008.
Bennett et al., "Tansley Review No. 72, Secondary metabolites in plant defence mechanisms," *New Phytol.*, 127:617-633, 1994.
Besseau et al., "Flavonoid accumulation in *Arabidopsis* repressed in lignin synthesis affects auxin transport and plant growth," *The Plant Cell*, 19:148-162, 2007.
Bhattacharyya et al., "Differential sensitivity of *Phytophthora megasperma* f. sp. *glycinea* to glyceollin isomers," *Physiol. Mol. Plant Pathol.*, 27:2691-2694, 1985.
Blount et al., "Stress responses in alfalfa (*Medicago sativa* L.) XVI. Antifungal activity of medicarpin and its biosynthetic precursors;

implications for the genetic manipulation of stress metabolites," *Physiological and Molecular Plant Pathology*, 41:333-349, 1992.
Carver et al., "Suppression of host cinnamyl alcohol dehydrogenase and phenylalanine ammonia lyase increases oat epidermal cell susceptibility to powdery mildew penetration," *Physiology and Molecular Plant Pathology*, 44(4):243-259, 1994.
Dauwe et al., "Molecular phenotyping of lignin-modified tobacco reveals associated changes in cell wall metabolism, primary metabolism, stress metabolism and photorespiration," *Plant J.*, 52:263-285, 2007.
Dixon et al., "Flavonoids and isoflavonoids—a gold mine for metabolic engineering," *Trends in Plant Sci.*, 4(10):394-400, 1999.
Dixon et al., "Metabolic engineering: prospects for crop improvement through the genetic manipulation of phenylpropanoid biosynthesis and defense responses," *Gene*, 179:61-71, 1996.
Do et al., "Both caffeoyl coenzyme A 3-O-methyltransferase 1 and caVeic acid O-methyltransferase 1 are involved in redundant functions for lignin, flavonoids and sinapoylmalate biosynthesis in *Arabidopsis*," *Planta*, 226:1117-1129, 2007.
Dwivedi et al., "Modification of lignin biosynthesis in transgenic *Nicotiana* through expression of an antisense O-methyltransferase gene from *Populus*," *Plant Mol. Biol.*, 26:61-71, 1994.
Guo et al., "Downregulation of caffeic acid 3-O-methyltransferase and caffeoyl CoA 3-O-methyltransferase in transgenic alfalfa: impacts on lignin structure and implications for the biosynthesis of G and S lignin," *The Plant Cell*, 13:73-55, 2001.
Guo et al., "Improvement of in-rumen digestibility of alfalfa forage by genetic manipulation of lignin O-methyltransferase," *Transgenic Res.*, 10(5):457-464, 2001.
Harborne, "Chemosystematics and coevolution," *Pure and Appl. Chem.*, 49:1403-1421, 1977.
Lorang et al., "Green fluorescent protein is lighting up fungal biology," *Appl. and Envir. Micro. Biol.*, 67(5):1987-1994, 2001.
Lozovaya et al., "Biochemical response of soybean roots to *Fusarium solani* f. sp. glycines infection," *Crop Sci.*, 44:819-826, 2004.
Lyda et al., "Biology and ecology of *Phymatotrichum omnivorum*," In: Biology of Sclerotial-Forming Fungi, Lyda et al. (Eds.), pp. 67-86, The Texas Agricultural Experiment Station, College Station, 1993.
Lyda et al., "Soil fumigation control of phymatotrichum root rot in Nevada," *Plant Dis. Rep.*, 51:331-333, 1967.
Lyda, "Ecology of *Phymatotrichum omnivorum*," *Ann. Rev. Phytopathol.*, 16:193-209, 1978.
Meyermans et al., "Modifications in lignin and accumulation of phenolic glucosides in poplar xylem upon down-regulation of caffeoyl-coenzyme a O-methyltransferase, an enzyme involved in lignin biosynthesis," *J. of Bio. Chem.*, 275(47)L36899-36909, 2000.

(Continued)

*Primary Examiner* — Brent T Page
(74) *Attorney, Agent, or Firm* — SNR Denton US LLP

(57) ABSTRACT

The invention provides transgenic plants with resistance to infection by a root-infecting fungal plant pathogen such as *Phymatotrichopsis omnivora*. Also provided are methods of making such plants. Further provided are nucleic acid vectors for producing such a plant. Additionally, methods are provided for growing a dicotyledonous plant that is resistant to root rot disease in soil that comprises *Phymatotrichopsis omnivora*, or another pathogen.

29 Claims, 13 Drawing Sheets

OTHER PUBLICATIONS

Nicholson et al., "Phenolic compounds and their role in disease resistance," *Ann. Rev. Phytopathol.*, 30:369-389, 1992.

Pakusch et al., "S-adenosyl-L-methionine: trans-caffeoyl-CoA 3-O-methyltransferase from elicitor-treated parsley cell suspension cultures," *Arch. Biochem. Biophys.*, 271:488-494. 1989.

Parvathi et al., "Substrate preferences of O-methyltransferases in alfalfa suggest new pathways for 3-O-methylation of monolignols," *Plant J.*, 25:193-202, 2001.

Reddy et al., "Targeted down-regulation of cytochrome P450 enzymes for forage quality improvement in alfalfa (*Medicago sativa* L.)," *PNAS*, 102(46):16573-16578, 2005.

Streets et al., "Phymatotrichum root rot," *Am. Phytopathol. Soc. Monogr.*, 8:1-38, 1973.

Tahara, "A journey of twenty-five years through the ecological biochemistry of flavonoids," *Biosci. Biotechnol. Biochem.*, 71(6):1387-1404, 2007.

Tivoli et al., "Annual medicago: from a model crop challenged by a spectrum of necrotrophic pathogens to a model plant to explore the nature of disease resistance," *Annals of Bot.*, 98:1117-1128, 2006.

Uppalapati et al., "Global gene expression profiling during *Medicago truncatula-Phymatotrichopsis omnivora* interaction reveals a role for jasmonic acid, ethylene, and the flavonoid pathway in disease development," *MPMI*, 22(1):7-17, 2009.

Vance, "Lignification as a mechanism of disease resistance," *Ann. Rev. Phytopathol.*, 18:259-288, 1980.

Wrobel-Kwiatkowska et al., "Lignin deficiency in transgenic flax resulted in plants with improved mechanical properties," *J. Biotechnol.*, 128:919-934, 2007.

Ye et al., "An alternative methylation pathway in lignin biosynthesis in *Zinnia*," *Plant Cell*, 6:1427-1439, 1994.

Ye et al., "Caffeoyl coenzyme a O-methyltransferase and lignin biosynthesis," *Phytochemistry*, 57:1177-1185, 2000.

Zhong et al., "Essential role of caffeoyl coenzyme a O-methyltransferase in lignin biosynthesis in woody poplar plants," *Plant Physiology*, 124:563-577, 2000.

\* cited by examiner

SEQUENCE LISTING

<160> NUMBER OF SEQ ID NOS: 27

<210> SEQ ID NO 1
<211> LENGTH: 2003
<212> TYPE: DNA

<213> ORGANISM: Medicago truncatula

<400> SEQUENCE: 1

```
aatctaaact ctactctctt gttaatcatt ttggtccatt taagtataat caaacttcta      60
tagcatatct agtttctaac cctataatat tataaattat gaagcaatac aggataaaat     120
aaaaatctaa cacaaatcat taaagctggt aaagtaggtt gtttaaaatt aaatttgtat     180
tctaaaatca taagattaat aataaaatgt tcaaagaaat atgtatattt taacataaaa     240
ataaaggaga gtgtaattta aactcttttt ttttttaag aaataaagtg taatttaatt      300
taatttactc ttgaaataat tgttccaaaa gtaacaaggt attattctaa atttcttacg     360
tagtaatatc agtatgcaaa ggaactactc ttttttcac caaaataagt gtcacagttt      420
gatgatatat actactcata taacatactt cagtcatata tttttcatt aaaatgaacg      480
caaatgttag tatataaaat gttgaatttg tctcaaaaaa tattttaaa atatcaatat      540
tttataatag ataactaaag atataaatag tcaaagttgt gcattgtcat atatgaaagt     600
taaacggtga catttatttt gagacaaatg aagtaatatt ttattagtta aacttgatat     660
gaatcaccat tttgatcttt ttttacttga ctattttggt ctatgaaatt atataagtca     720
gtacatttct taaaccccca aattaatttc caatgttgtg aattcgagac tcaaaactcg     780
cagcaataaa cgttgatgtg tggagcaagg gtcacttgca accaataacc aaaacaattg     840
caagcaataa taacaatgca aggcaaaacc acatttgaac caaagaacaa caagataaaa     900
aagagaagag aatatagaac aatgcactga taattgtttt caatcccacta tcagtaagtt     960
ctttacaaag agatacaaaa gttacaataa attagccttc aactagctct ccaagaggaa    1020
accttaattt ttacccttct catgaatgtc ttcctctgac aaagcgactc atttcatttt    1080
ccaaagtatt taaaactgtt tcaagacaat atactctacc cctgaaagga atcaacccct    1140
agcttttgat ttttttaaga ataacctcta ttagtctcac aatattcatt caggctgcat    1200
accaatatct caccctttca tgattttttcc atgtgttttc caccccataa atccctcccc    1260
aaaaccaacc cttttccaag aatcgtttct tttggttttc caaaatccac attttttcaca   1320
ctcaaaaccc taaaacttgt gttgcctatt tatacaatag ccaccatgcg catcgcgcag    1380
caagtcgtgc aataaagaaa atccaacatt gaaagatttt gcgcattcat atgagatttc    1440
aaggcacatt tcaacattta aaatacacat tccctcttat ttaagtgtcc attttaaaat    1500
attttattgt ctctgtataa tttgtctctt taaaacacca atcacaatta gtttgatca     1560
agtggttctt tctttggtca tgttagatca agaaattata tagaggttgg atagcttaat    1620
tgtttaagtt aagggagtca agtattctga gtttaaactc gggtgaacgg gtgaatatta    1680
ttaatctaac aactaatttta gtaatatttg tcattaaaaa aataaagaaa ttatatattt    1740
attttagttt tcatgatttg tgttaactaa cgataatgac attggtagta ggtgaacttt    1800
gtacatttgc aatatgatcg ctgttatgtt tcatattatt atatattaca ttacatttta    1860
tatttatttta tcatgtatta taaaaggaat gctcttaaga tcattcacat actcaggaaa    1920
ttaagaagtg ctacgtactt cgcaatcaca catttcttta attttttcca tttgaagtgt    1980
atcgtacgta ccctttagca atg                                           2003
```

<210> SEQ ID NO 2
<211> LENGTH: 2003
<212> TYPE: DNA
<213> ORGANISM: Medicago truncatula

<400> SEQUENCE: 2

```
cttattaggg gttaatagtg tttttcaccc ctgtaatata tatatgtcat ttctggttgt    60
cgtccctata aaattttcgg tttgatttgc accctcgtaa aatttttatt tttcggaaaa   120
caccttaat aggccattca aaaccaaaa tttcttgaaa ataattctg aaaatggcct     180
attagggtg ttttccggaa ataaaaatt ttacgagggt gcaaatcaaa ccgaaaatt     240
ttataaagtc aaaaccgaa ataacatat attacagggg tgaaaatcac tatcaaccct   300
aacgttttgg atgtcagcat atagttggga tttcaaaaca ttttattacg gtaaattggg   360
tgccaacata gttgagaatt caactgtcat attcaacgtt tatcaggata aaaaaaatt   420
atgaagtatt atttaaggga ccattttttt agtgtcattc ataattggtg gatcggccaa   480
actcttctct tgtgtgtttc tctatcctaa tcaaaatcga catacccttag agtgattggg   540
caactatcta aaatatatat acatagtgcc cacatactca aatctcccca tttcacttat   600
cattgttgtg agatcatcaa cctatccaag caactgatat acttcctatt tggttggacc   660
atgtaaattt cctctccatc aaggataagt ctaccaggtc tattgatttg aggaacaagt   720
taaacacacg agcattttca aaacatttca ttgtcatttt attttaggat tgtaaaggat   780
tttattgagt tacacttaaa ttcttagcat gtatatatct ttaggacgac aaaagttacc   840
atttcctttg gcttaattca ttcttacaaa tttggcttat aagatgagga tattgcgttc   900
atttataaac tcatgtccat accctctctt tatttaatat gggattttt aacacatatc   960
tttcacgctc gtgactggac atatcatatg tgacctaaaa gcgatgatct tagcatgtaa  1020
tctaacatat cttagacagg ctctgtaatc ttattagatt tttatattgg gtgaaattca  1080
tcttttgaaa atcgatttac aagatgggga ttacactcat ttataaattc atgatcaagt  1140
cctagtttat ttaatgtgag actctttaac aactaatagg ttctagttta tggttttgtg  1200
gaattttttt gttatgtttc ttgtaaatgg atttgaatat cacttctact cttaacttaa  1260
atagtaaaaa aaaagtttta caaagtataa aaaaattaaa aattaaaaca taaaataaaa  1320
tgccctcatt tttcaaagct aaatagtcat cataagaata acattatcga tatataaaaa  1380
taaaataaaa aatctaatca caagaaaaca cttcttccac ccagtggatc aaagctgact  1440
tgtcatctta gcatcaataa tattaattaa tgatttctat aatgttggga tagcaattag  1500
caccttaat taaccatgat gaagcccact tcagtcattt tataattgta ttaacaacca  1560
cttcctctat gctctaaacc gaccaccata ttaatgtata tatttgtgtg gtgtatatgt  1620
gtttgtgtat aatacaaact gtaacatata tttagttaac ggttagaaca catgatgctg  1680
cacgcacaga ccaaattta atttccataa tacatggcac tatgacaaca ggacattcta  1740
ttttttgttc aattaattaa ataaacacct atgcatggtt gtaaagcaaa accacaaacc  1800
ataacaacat taattaacgt gactgcttgt tccacatact gatcactatc taccatacat  1860
acctccaatt ccaactccta taaattccat cttggggaac actagtttgg cagatcacat  1920
ttcataacta gttcaattca gtttaattat atattattat aataattaag tactagtatt  1980
agtcaaataa ttaatataac atg                                          2003
```

<210> SEQ ID NO 3
<211> LENGTH: 2003
<212> TYPE: DNA
<213> ORGANISM: Medicago truncatula

<400> SEQUENCE: 3

```
taatcttagg tcatatgcaa ctgataatgt taatgggtat catgttatcg agccaaatgt    60
acaagcatta gtattttgtt tgatgattga tattttatt tatatttgta aaacattaaa   120
```

```
tgactgcata tcataaagtt ttaagaatct atatgataga tttggttttt gttacaagta      180
caattgaact tagtggagtt tcctcatgat agcattcagg ttttgggaag ttttttttcc      240
gagttttcaa ttttcatcga cataatattt ttatattttg gcatctaagc ttaatctttg      300
tctaatattt tttttaagtc ctaacatact cgaaaccatg acatttgca cattatttat       360 tctcagtttg tttacaaagt gtggtatcat aggagtggtg tttcactatt taccactgtc      420
ctataagaag caattttttgg gttgagaatg tcttttgaaaa taagacacca ttcatcggtg    480
attgaacaat aaaaaaataa cggtacatca tataattacg gggagaaaag aacgttttag      540
taagactatt aataagacta tgatcaattt tattaacttg tcttaaaaaa aacgacttta      600
taatcgatgt tatccttaac gatcgtacaa catttgcaca ctgcccctcc taattcattt      660
aacatgtttg aggaagagtt gaaagcaata aaaaaacttg ttgcttcctt ttgcagcgta      720
aaaaaaggtg tgaggatttg aatccctttg accatgtcat tttaatttta ttttgtttct      780
cataggtttg gtgcaccgga tgtctgatat tctatttgag ttagtgttgg gtgaacactt      840
attccaatga gatttgaatt tgagttcatc atattataga agtctaacct ctgatgttaa      900
aaacaacctt agtcaatctc cctcggttta aatcattcat ggtgcaaatt atcatacaat      960
taatatgttc cattttcttc aataaatgca gatattcata attcatttat taagataaat     1020
gaattaggtt agaaaaaacc taataataat tcaaatgtag gcataagagt tactatgact     1080
tgtagtgtga taccatgtga ttttatttta ccacacaaac ctatctacta gcattgttaa     1140
gaaaaaagta aaaaaaaaaa atctaaactg aaccagttcg atctggttca attcggtttg     1200
tgagccatca atgcagtgca gttcatttta aaagtttttt ttttttttttt ttttctaaaa    1260 tagtcataat attcaatttg gtatagtttt tgaacttgtt aacaatctta attattagtt     1320
aataatagat atttagtaca attccgttaa aaatagtttt ggttcagttg agaactacaa     1380
aacctatgta caaaacctac atatatcagt ttggttcgga acgaacaatt acagttcagg     1440
tttcttcttt aaccaaacta tgaacaacat agtccaaggt tttgtctaca tgcacatgaa     1500
tgatgataac aatacataat aaagaatata ccgaaaccac taacgctcaa tatttaattt     1560
gctaatttta tatgtagtac atggtgtcac agcatctctt ttgataacct attgttactt    1620
ttccttgtaa gcttccattg catcaatttg tattttataa gaaaatgtag tactctcata     1680
gtcccattaa taataggtca aaagagtaaa caagtactgt taattaaggc tagtagtgat     1740
taaagtgaaa aaagttccat actagctagt atagtatgta agcaacatta tgcactccca     1800
atataattat agtgtaaaat ctcatgctta tgtcaaagcc acttcaagct tagcacagag     1860
caaacctaat ccactacaat aatttcctct cttgaatatt gtaatattcc atgctgtgtt     1920
ttttgatgta tataaatgag taccattctg atacttgttc actctcaagt gaagaaaaga     1980
gaatacaagt tggaacaaaa atg                                             2003
```

<210> SEQ ID NO 4
<211> LENGTH: 2003
<212> TYPE: DNA
<213> ORGANISM: Medicago truncatula

<400> SEQUENCE: 4

```
ccattgttga agatgaaaag ctcaagataa tgaagaaaac aagaagaaaa cagagtaatc       60
aatggtgaat ttgcagaaaa tgcaagaaat tcaaccagaa aacaagaaga aaatagagta      120
atcaatggtg aatttgcaga aaatgcaaga aattcaacca gaaaagagaa gaagacgatg      180
aattgcagcg gaaaagagaa gagaaaaacg gttaggatca gaactactct caaagagagt      240
```

-continued

```
gctctgatac catattatga aacaatagaa aactgaaatg attcttcatt atcaacaaat    300
gagagagtta caatcagtat atataggcaa actaaatgta ctacactaat ctagttgtac    360
tacacaatag ctgaaagtgc aatctaatag tataggtgag attgcttgca ttgcaagtta    420

tcaatctcta agtgttattt ttctcatctc ggtgcttagt gtgtaatagt tgtctttgac    480
aattgacatt ctaactatct aggaacttag tggttatatc cacaatcgca tagaaacttc    540
ttgccaaagt tttcgagtgg ttatttccat accttactca ttactaaggc aagatagcta    600
caatttgata agtgaaatct cagtgaagtt gaagcaacat cgaaaagttc attattagtg    660
tttgtgcaaa caacgaatcg acttaatttc cattggtgat tgcaatctac tccatccttc    720
ctaaattata cgacgttttg gtgctttttc acacatatta aaaactgtat taatttagta    780
agataaaaac atattataaa ttattttaca aaattgtcct tattaaatgg tatgaaaaaa    840
ataaataaaa gaattgaaaa aagatagagt aataaataat taatgttata ataaaaaaaa    900
aaaacattaa tgtttcattg ttttataaaa cgacttaatt taggatggag agagtacatt    960
gtatctcatc aaaacatttc ttgaagcact tctggagaat aacaactttg ttgttgtttc   1020
tattatgagc aaggatagtc attgttcaat taacgacctt gaatcttagg gatgaaatcc   1080
gaaacaagaa aaaaaattgt tgattctaca agtgtgaatc tcaaaagaaa acattctttt   1140
aaattttatg cattcaatta attgaaaatt taaaaattaa atttaatgta ccaattccaa   1200
caaagtattt ctacatttaa tttatagggc acatgatagc tcttaattca ttaacgttgt   1260
cctttaaaag cacaagatga actcgaataa aacaattttt aatcaaactt tatttatttt   1320
ttgatcaact ttaaattatc atatctattt ctcataagag ccaaatagct aacacaaaaa   1380
gtttacacca tcaccgatgt caaatttttt gtcaaaatgt ctataaatta aatgtttttc   1440
gcaattatgt tgaaaacggc gaataaaaca attctatcat attatccaaa aaaaaatgaa   1500
agaaaaaata aacaattcta tcatgtacac aatctttttc atccgttttt ttctttctaa   1560
tacaatattt ttcccgttag tgatgcaagc acttacgaca ccaatttatt ttttagggga   1620
tacgacacac acaacattat tattaccaaa aagttaataa ggtttaatat ataaaaccaa   1680
gggttggttt ggtggtcatg aatattgact taagaccaac atgatatata tattaaaaaa   1740
atgccaacaa catgcatttt atagaaaaaa ttcgtcatat tttgttttct tttcacaatt   1800
ttgtcttttc tcatcttaat taaatccaca acttcatatt caaattgtta tatttgttaa   1860
tgatagcgat ggattggagt aaaaaatcaa agcgatagta acacgtattc tattttactt   1920
tttaatttga atagttgacc aagccaaatg gctccatgga tgaccctatt aaaaagggtt   1980
agtgtttcat ttaggaaaac atg                                            2003
```

<210> SEQ ID NO 5
<211> LENGTH: 2003
<212> TYPE: DNA
<213> ORGANISM: Medicago truncatula

<400> SEQUENCE: 5

```
taaagttgtc aacacaattc caactttctt ttcttgtgtt tcctccacct taatgtattg     60
tgatttcaac catgcaacaa acatttttag atgtgctatg gttcaatgat attaacaaaa    120
ttctcacgat gggacgttaa gatcagataa tggctcaaag tccttatatt ttagttgcat    180
tagactttga ctaagcgaca taaggtttca tgatagtttg taattcaaag ttttgttaaa    240
tttcaattga tactctttga gatatgcatt tttgaaatga cgctttttct tcattgtgtt    300
gtagtatagt atggtcatga tatggaatgg gatttggtgc tgttacagtg tcatgctgta    360
```

```
acagatctcg gccgtctgat tttcatcgat ggctgagatc aaactgtgtg ataattggcc    420
aaacaaattt aaaccattga atcatttata tatggttgag attaactact gcgtataact    480
gcgtgaagca attacagtaa gggatctaga tctgtcatga tataatatag aatgaacttc    540
tcaaacgcta catataaccc tatgctatct agcaagatcc tcttcaaact ccaatgtgta    600
gactcgacct attagttgta gtgttccctc aatgtaaaaa atacaaggat ttctattctc    660
tcgaaaaaat gaaagaaag agtgatagat atcaatataa gagagtaagt tgctaatttt    720
gttacaccca ctcgctagga ccctctatta tttaacaaaa ataacttacc taaatgaatt    780
tgagagagaa ttcattttca aaataaaaaa taaaaaataa ttcgagaaag aaataatatt    840
tttttacgg acatatgaaa tattaaagac tagtttttt tttttttaa ggaaaacact    900
aaagcttatt atttaattct cttgtgttcg gacaattcgg aaagagcgga ataatagaat    960
ttttagcaat aaggaagact taattcatca tcatctcttg ggcaaagcca agttactatc   1020
ttattagtga ccgaaggcaa aatatgttaa tgtagctttt agttatcata atgagtgact   1080
ttagtccctt tttttgtttg ggcgttgact aataactcta ttttatttgt tccctttcat   1140
gttggtttga ttatcttttg taagactctg ctgttcttct ctagtactct ttgtactagg   1200
aagaatgttt tttgctggta atatatttca ttttgacttg ttaaaaacat gtataaattg   1260
gtggtttact ggaataaaat gaaataaaac tatatgattt tccattgtat tcatttcatt   1320
ccccctctct cttttttttc ttataaaaaa aatgtttcat ccttgtgatt tgacttaaat   1380
ggttataagc ttcgtttaat atgaattcca gaagaatttg agttagaatc ttgttcaaaa   1440
taatctttaa acaaacatta tttacctcca atcaaattct gtattattat gaccatagtc   1500
cctatcttaa ggccaaaaaa attccctct cttgtcccca aaacgaattt agccgcaatg    1560
tcagcataat ccttggcaag tatggaaggt aacaactaat aacaatatcc ctcaaaaaaa   1620
attaataaca attgtctcct tccttaaaaa aaaaaaaaaa aattgtctcc tatttgcctt   1680
tctttattg catggaccac actccacttg cacacatttt cagcaattta aatatgaaaa   1740
acaataagat accctaaaaa attctacttc tcaacaaaca gaaagtttca aattttcttt   1800
ctacaagacc catgtcttt cttccctcac aatgtcaaag gttctctata tattacaaca   1860
tttaactacc aatgtagaaa ttgtacacct tctttacata aattaaaagt cttcttcctt   1920
ctcaacttcc tctacctctc aacatgatat actcttcaat actttatatt aatcattatt   1980
aatatccact gtttcatatc atg                                           2003

<210> SEQ ID NO 6
<211> LENGTH: 1697
<212> TYPE: DNA
<213> ORGANISM: Medicago truncatula

<400> SEQUENCE: 6 tactaaccccc gaacccatac ccaaacccta cccgaatgta gaaatgtcat attttttgttt    60
ttgttgaggg ggttgataat gatatgtcat gttatttggt ttgataattg tcatgatata   120
ggaattttca ttgatagtta aaggagcaat cgaattattc ggtatgaaaa tgttaaaata   180
aacgcaaatt gttggataat gcattataat attaccattg aagcttaaaa aaatgctttt   240
tttattaaaa aaaattgatt cactacgggg acgggaatgg ggttggaata cccgaaccca   300
ttggggacag ggatgagatt caatttctca tctccgttgg atataggtag ggtagcggat   360
aagtatatga gagtaggaga tggggatgga gatgaggatg gagattgcaa aacccatccc   420
caccccaccc cattgccatg tttatactta agtgtcgaaa aacgaaaaat tgcggttttg   480
```

-continued

| | |
|---|---|
| aacttgcaaa ctaatatata tcaaatgtat attcattctc ctaccatctt aattgtactt | 540 |
| aagtgacaaa acttggatta atttatttgg actggtttcg taatgagttg tattcaatca | 600 |
| ttctcttctt tacaatttg ggtgaaagtg gtcattgtat tttcttaaat aacttttttg | 660 |
| cttatataaa aagagagaga aaaaagatc gtttattgtc tctactttga ttatagaata | 720 |
| gaagtttaag acttaatcaa acgttataaa ataataaaga tagtaagtct tgcaaataaa | 780 |
| ataaaaaatg agagtgctga taaagccaaa accttacaca aattgaggga ttaaaaagtt | 840 |
| actcacgtct atgcataatc atacttacac tcaatattct ccaccaatga taaaatttga | 900 |
| ggagttactt caactttaga aattaatttt tttttttgac aagactttag aaattaatta | 960 |
| ttatatattg agtgtaatat ggattaatca tatactaatt cattatatgc gtgactagtc | 1020 |
| aaacaagata aacctggatg gtaattgatt gtaatgcacc accaacattg aattaaaaat | 1080 |
| tagcaagttt tttttttgttg gaaaaaatta acaagttaaa taccaaaatg tgatttaatt | 1140 |
| tttttaatac gcaaatttta atggttaatc tgttaggagg aaaaattgtg aattttttag | 1200 |
| tgcataaatc aaaccgttga ccttttattt gaactcgttt agtctcaact catatcattg | 1260 |
| gactctacct tcgagaatgt accaaaatgt gttagttag acctagcagg gccacataaa | 1320 |
| tgaactcgaa catactttc ttgaaaaatt gttcttctcc catttaaat tgctcactcc | 1380 |
| tttgatctat cgggagttaa ctcatactcg gcattattca acggtagcta acccacattg | 1440 |
| tcactgttag attagttcaa tcattttta aatcgagtca accaatctta aaagtctcag | 1500 |
| catgagttaa ctaccgctga aaaatgtcga gcccgagtta acttcatctg aatcaaggga | 1560 |
| atgaacaatt ttaaaaggga gaaaagcaat tttcctttc ttgaactcat taaggttcca | 1620 |
| aattcttta taaagggcc actacactgc tttcatatat gcaccattca tacatagaaa | 1680 |
| ccaatagcca aaaaatg | 1697 |

<210> SEQ ID NO 7
<211> LENGTH: 2002
<212> TYPE: DNA
<213> ORGANISM: Medicago truncatula

<400> SEQUENCE: 7

| | |
|---|---|
| taaaatgaaa ataagtattt gtgttttttg catcaaagac gaatttgagt cattaccgtt | 60 |
| atgtttgctg gcttttgatt tagttatatg ctttggtgga ttttgcaggg aattgcaaaa | 120 |
| aggcttgtga gtactgttct agcgaaagcg gctgctaatg gaatgttac ctgtaatagc | 180 |
| atgatgcatg ctaatctggg acgtggcgat gggaacagga ggtcttttca tgatgatata | 240 |
| agtgtgattg ttgtgttctt tgacaaaacg tcgtttctga ggatgcccgt acataatttg | 300 |
| tcctacaaaa gctcatctga cagacctaca ccatctgctt tgcacggtc tggattaacc | 360 |
| actcattggc tgcagaggct gaagaagact attaaagacc ggtttaaagg aagttcatcg | 420 |
| aatgcatctg gctctcagga tcagaaccct gaaaccctg agggcgagag ctctcaaact | 480 |
| cagagccttt taggtcagag ttctcgggct cagagtcctt ggaagaatct taaacagaat | 540 |
| tagtagaaca aggtggattc cttgcagttt atgataaggt tgatagagtt atatatgact | 600 |
| atctcacaga aaaagctcta aaatctgcat ctaggatcaa tgcttattgt ggtatatgag | 660 |
| gtgcacatct aatggtataa agttagttgg tgactgcttt atgctgtgct atgtatgtgg | 720 |
| aattaaatct aaatttctat agtttccaat ttttattaaa ggagtttgtg gttatgtaat | 780 |
| ttgatgtgaa tgaccttaaa tgaataaata cttactcttg gtcattgaat aatctgtcac | 840 |
| atatgtgaat actttctttt agctctaacc ccagttgaat ggtttcaata tgtaatttcc | 900 |

| tcagcagccc | aaatgagaaa | gagacaagat | tgaaattttg | aaataaatac | aaagaattca | 960 |
| acgttgccct | tgaaagaaga | aaaagattgc | caaacttaga | attataaagt | aaaacaatga | 1020 |
| atatccaaag | gattattcaa | gtggtatgtg | ttagtacatc | aaaaaagtat | tttttaacta | 1080 |
| acaagttcaa | gatttgatct | ctgaggctaa | ccaatcttct | tcaccctaac | aaataaatta | 1140 |
| ctaataatct | gcctataaaa | caaacaagaa | aaacaaaaac | tacataaact | atactaggga | 1200 |
| cttggattaa | ttgtctcact | cttttcatagt | tacataatct | gtggtccaaa | gtttgattgg | 1260 |
| ctcattctgt | caagtttgac | attataaagt | aaatacaaac | tacttagttt | ttacgtttta | 1320 |
| tgttgcagag | gactatgaga | taatgcacaa | actgttaaag | gattagctct | gcaatagtct | 1380 |
| taagtatatg | tttggagtag | acataattga | ttttggaagt | gtaatatgtt | tagtttttcc | 1440 |
| attcattcca | aaaaatttgg | caagtatttt | gatatgatat | caactttctt | tctcatactc | 1500 |
| acattatgtt | tttactttat | ctccttattg | ctttggtttt | tgtgtcaata | cctcttttc | 1560 |
| tttataaaat | tatggttatc | tcaaaagtta | tcaatcagat | agttgttcaa | ataacacaac | 1620 |
| tctatttcct | aagagtctaa | tatggtacgt | ttagatacat | gtgtaaaact | ttttgttttt | 1680 |
| aaaaaaagtt | cttatataaaa | tagaaaaaag | tcccaaagct | ttgtaccaaa | aataaaaaag | 1740 |
| tcccaaagcc | atgacgtttg | tactaaagat | tttaatgcaa | tttttattgt | gaattattgt | 1800 |
| actatcaaac | ttttaatgca | atttttgattg | tggtttattg | tacatatgtg | aacttagcat | 1860 |
| aagatgtgaa | attatttagt | ggtcctgaaa | ataaatatat | taatctcaaa | catacaaggg | 1920 |
| aggtttctca | ggctataaat | caacaccaga | tatagttttcc | tttaccatgc | accaattatt | 1980 |
| ttgagagtga | aagagcatca | tg | | | | 2002 |

<210> SEQ ID NO 8
<211> LENGTH: 2003
<212> TYPE: DNA
<213> ORGANISM: Medicago truncatula

<400> SEQUENCE: 8

| gaatttggcc | atgaaaagtg | ttattggaaa | ggtcaagtga | atgaaggtaa | gtgaggttgg | 60 |
| agaggttagg | gggtagttta | ccagagagtt | taagtcctga | taaggttaga | gattgaactc | 120 |
| tttcatcaac | tttggaacag | ttgacaccat | accaggtaca | atgattagaa | tcttgtttcc | 180 |
| aactggacaa | agcattgttt | ggatcagtta | cttgtaattt | gaatgataga | agaatatctt | 240 |
| tgtcagtgtt | attgctgcaa | atgatgccat | gaaaattatg | aagtgtgatg | cataggaaca | 300 |
| aaataagtcg | tatatggatc | attgtagctt | aggaggtaaa | gtaataatgt | ggcgttacac | 360 |
| tttaatgtat | agctcaatgt | gcttgcaggt | atttatcaaa | ttattataac | tgaaattctg | 420 |
| gttttttagt | agtagttgga | aaagaactgg | tcatggtatg | aacgttgtat | attcaacaca | 480 |
| aacaggcaag | atgatgattt | tttgtttttg | accttcaac | tgttgtatac | atttgtaggc | 540 |
| caatatgtaa | catctatcct | ttgacaaaaa | acacaaatga | tcaatacaca | tattaaagta | 600 |
| ggctgtgttg | ttggttggag | acttggcacc | tccacagaaa | agtcatgcaa | tcactttttac | 660 |
| caaaaaagat | acacaaatat | caacacccgt | gttaattaat | ttctttgctt | tgaccctaaa | 720 |
| gtttacacaa | cttgtgcatg | gtttgacttt | gagattgatt | tcatatatcc | cttcccttcc | 780 |
| aaaataagtg | gcatagttttt | acatacactg | ctcacgcatc | gaactttcag | catacttttt | 840 |
| cactattata | taaaaatgag | cttgttgaat | ttgttttgat | gaatattttt | aaaatactaa | 900 |
| atttttataa | ttttttgctaa | tatataatta | aaattataaa | aagttgcaat | gtcatgtgta | 960 |
| aaaccatcaa | caatatcact | tattttggaa | cggagggagt | attagctata | gtagtattac | 1020 |

```
acgcacactt gcacgcagat ttaaataaat atccacccct aattataagc actaattgtg    1080
agagaaaatt tgtccctaaa tagatctatt tattactccc tccggtccca tttacaagaa    1140
aaaattaatt ttttagatac attgaataat gtatgtatct agtcaataac ctaaactaaa    1200
tacataaatt atttaatgta tcaaaaagt aaattgtttt ttgtaaataa gaccggaggg    1260
agtactacat ccctaaatat aagatctttt tacaaattta ttctcataaa aagggacaat    1320 ttttttctt ctcaaaatga tcttataatt aaggacacat gtaatatttt tttttcaaac    1380
acaaccctaa ttaatatcct ttttctagaa tataaaaagt caattataaa tacattcata    1440
caaatggtaa tttagtctag ttgtacgtaa aatgtataca ttaattacac tatcaatatt    1500
tttatggtta tgctaacaag tgtcctaaag acattgttta aggaatctat tataagaaat    1560
tttatcttga aaacataaat ctaacatatt taaagtaat attacacaag tttgtataca    1620
aaagttaata cttttagttg cttaagcaat atctcgttat atatacgtat agaagaaggt    1680
atatatagtc tctgtgaact ttgctcaatt ggtagggata ttgcataata tatcacttct    1740
ttcacattta aaatgtgtga tcatcaatca ttagactact tgataaaaaa ggaagaagat    1800
atatgtatga attattatta ttatttttg taaaaattat aattagtcag cacacgcttg    1860
taaacatctc tgcttctcta tgaactttc aaaaaaaaaa aaaactgtt tctctataaa    1920 tacctggtcc taagtgatat attatgatca tcccaaactt gcaattaact acatctatag    1980
attactagtt tttgttagaa atg                                           2003

<210> SEQ ID NO 9
<211> LENGTH: 2003
<212> TYPE: DNA
<213> ORGANISM: Medicago truncatula

<400> SEQUENCE: 9
ttaaataacc actttggaaa aaacgaaaaa cttaaaggac ttttagatgc atttgaccta      60
aactttacta caataatgat taccatactc tttgataaag tagaagaaca tgagaaggag     120
ctcattcaat taactaagca tgaagaaaat ggacaaagga caaggagaaa tagtgataac     180
aatgatgtct caagtgataa agagatgagt ctcttcatta aaagatataa caagttttta     240 agaactttg tgatgaaagg cacatgacat atagataatc gggttcgaat agatatgaga     300
tatgatagtc aggattctta gtgtttactt gagtttttac tccttatcga ttgttatatt     360
agttgttgtt agtgaagttt ctactcttcg tcttgtagtt ttttttcttc gaataaaaca     420
actttaagaa aaagaaatcc tattcaattc gaataaaata tttaatgaga cgtatgagcc     480
ggattcttgt acttaaaaat catttaatga gacgttcata ctccatgatt aacttcacat     540
tttgaataaa accaacaagc atggaacatg cttcgaattg aataggattt cttttactta     600
aagttgtttt cgaacaatac ctaaataagt tcttatttaa gaaagggtc atgctaaccg     660 gtgctcccaa gatactggtt aagcatatca taaagggaa ttattaccat caaaagaaac     720 tgttttgac attattataa attaattaca caatttcaat gtattaacta ctatataatt     780 tccttttca tatccttaat cagtgccccg ggacaccggt tagcatttcc cttaagaaaa     840
agactaacag acatcatttt aaaagaaaa ttgctaactg actattgaat gccactgctc     900
agcttttgct tttaattaaa caaattaaa gtgtatacaa tatatctata ttaaataaga     960
attaaaatat aggtgtgttt aatatggacc tctaaaaaaa tactcttgtg attctttagc    1020
atttttagta aaaaaaataa taattataat aaaaaagag aataaaaata ttttttatta    1080
aattgtacag tttattcgaa aattgagactc acactactaa aaaaacaaaa attagtgaga   1140
```

```
-continued gaaattttgt gagggaaaat gtgaaatccc tctctaattc cgtcactaaa ttttgcgact    1200
atgaaatttg tgaggaattt cattttttcc gtcactaatt tccctcgcta attttgtttt    1260
ttctagtagt gtcaacaact tctaaaatct tttgtagtct ttagataaat gcatctgtct    1320
tcacaagata acatatcttt ccaacgagat tgaaagaaca atgtataaaa ctcattcatt    1380
ttttttttta aaggaatat aaaactcatt catatatacg ttcattttca cttttgaata    1440 tgcatttgt gtatatattt tttcttttct ttgtgcattt tacctaggta gttttgtcca    1500
tgatgtttct tgcatcttaa ctcgtacgct tgtattctta atccattaac ttagaaacca    1560
taagaatcta actttaacac tagattgctt tttcgagttc attcatttaa tttgtttgaa    1620
aggaaatact ttcacgccaa gactctttat aagctttcat ttatatatat atatatcatc    1680
catgcataac atatgggttc caacttttga ccacaaaatt ttttaaatcg gtaatacccca   1740 attaaattga aaggtttgat ttacctttaa acccttttac gatagggcga ttcatactaa    1800
ggactaagga gtagtcttaa aatatttaat tcctcatttc aatcaagaat aagaaatata    1860
taataaataa tttgtacaca ttttcattg tcctattatt atattgacaa ccatgtttct     1920
cttaactaga gaaatgtct atataaagaa caaaaccctc cacaacacaa taagcaatta     1980
agtgaacaac tatattaaga atg                                            2003

<210> SEQ ID NO 10
<211> LENGTH: 2003
<212> TYPE: DNA
<213> ORGANISM: Medicago truncatula

<400> SEQUENCE: 10
aaaaaaaaat aaaactaccg gcaaagagag aaggtgcaat gatggccatg cgggaacgat     60
gacgagggtg gcggtgaaaa aagcagcaac ttcgttgttg atgacgatga cgtttacaga    120
gaaggtggaa caatggccat gccgaaacga cgatgagggt ggtggtgaaa tcaaatggtg    180
attcactttc actgctggaa gctcgtggga aattaaagga gattgaacga ggaagctcca    240
aaagacaact acaaggaagc tcaaaacaaa tcaagaaatt ttaaagttca agacaacttc    300
ttttggcctt gaagaaggct aacgtaacca atggtagtta gtagatccct ccattaaaaa    360
agaagtgatt tagcatatct ctaactaaat gaaacatatg tcattacttt atatatattg    420
atcatctaaa aggatcacat gaaccaattc cttgtagtaa gaaaatttta tggcttaaaa    480
tacacttgtt aaattaaaaa ttgtagtcag gaaggactaa atcaaaataa gcagaagcac    540
taaaccaaac taagttccct ttaaatacac ttccaaagtt ccaatacaac caccactagg    600
actaagaaga aacgaaaatc tcaccaaagg agggacactg gaccataaac aaaaccatca    660
caaattgtca ataaactctc aaatttagag accgaaacag gaagttacaa gggataaaaa    720
acataaataa aaatattgca acaaaaataa ggaaaactac gtagcacagt ccgcacaaac    780
tagaacatgg atggttttttc ttcacaagca tggctagaag tagaacacgg tagtgacatg    840
tttgaaatag tcagtaacat gttcaatcta gccaaaagaa caatgttcaa tatcatacac    900
cttcattgtc atatgaatgg aagtattgac aattgagaaa tcagaaatgc attattgaag    960
tataagtgct ttccttcaaa aaaaaaagta taagtgctaa agacccatat gcaagtgggt    1020 cctcagtaa tcttaaacag attctgttag aaattgtatg gtaaacgcaa tgatattaat    1080
tacatgcgaa atgggaaatg cagataagtg tctctgagac acttttttaag aattataagt    1140 tgtaagtatt tttgaaaatg tgtacattca atgtatttga tcgaaatgtt tgattttttt     1200
agaaaataat tatttagttt agaatgctta aagagtgtcg gtatcgttat atatatatat    1260
```

| | |
|---|---|
| atatatatat atatatatat atatatgggt ttgctaggat acacccacta attttatgt | 1320 |
| gggagtgttt tagcaaaaat ataactaaaa agttgttaaa tactccctcc gtttctaaat | 1380 |
| ataagcaaat tttacttttt caattaatga tgtatctggt tcataatatg gaccacatag | 1440 |
| atcattatta attcaattaa cctaaaaaat aagtggatgt atgttagcaa ctcctacagg | 1500 |
| catttgctat aatacaccca cttaattttt agaaagtgtg ttttagcaag ttataactaa | 1560 |
| aaagtagtta aatgcacctt aaggtatagc ttgttaaaac actcccacat aaaaactagt | 1620 |
| ggatgtgttc tagcaaatcc catataaaaa cttcttggca atgaaagatg caatttgcca | 1680 |
| ttcatttatg ttgatattcc accacttatt actttgaaat gtatcatgta tgccttcct | 1740 |
| tgcaactact gaccattcta taaccaatc agacagaaaa tggttttttc ctagtagttt | 1800 |
| acaaaattac attagtgtgg aaatactctc ttatataagt tcctcccatt tatatgcata | 1860 |
| gacactaaga taataaagaa aattgtgtgt tggttaaagg actaattcca ccaataacat | 1920 |
| tatgcagtat ccttccgtaa atgaaacaga tcatagtcat aactacccc ctcaaagcta | 1980 |
| tgtcatacaa atgccaagtt atg | 2003 |

```
<210> SEQ ID NO 11
<211> LENGTH: 2003
<212> TYPE: DNA
<213> ORGANISM: Medicago truncatula

<400> SEQUENCE: 11
```

| | |
|---|---|
| tataacacat tcaacataaa cttttcaaa ctcaaactaa atacatttta aatgttatcc | 60 |
| ctgatttgtg aattgagaaa tcattgggga atagaagaga gagaatttga cataaaaaaa | 120 |
| tgaagttaac taccgttaga gttttttgt tgtcatttca tatattttta agcaacttct | 180 |
| tacatggaaa aaacaaagta tattatggat tgttttatct ccgtcttaac atgggctaat | 240 |
| taaatttta ttaagattag ggataataat tagactcata tccaatgaat attatctagt | 300 |
| aaaataaata aaacttcttt tcttttttc catcctattg atttctcgcg cgctatatac | 360 |
| aatacatatt atataatctg aatgacataa acatctcgta agaacctta aaacatgtta | 420 |
| aaacatttcg aattttaaaa tcaaaataaa gcgcgcgaga acctcataag gtgacaaaag | 480 |
| taatgccaaa aataaccat aacggatgga gtaaaaccct acattataca tatgaacatg | 540 |
| gatagctatc cacaaaaata agcgggtagg ggtaccttag tacccaccgt gcctcgtacc | 600 |
| cgcaaaatat atatttatac tttgtattca tattattata taaaatatt ggcaaaatta | 660 |
| cagtcgtggt catttaattt aattttgta acgatttgat cttttatctt ttcttcattg | 720 |
| tagttttacc cttttagtct atttacatat agattttaaa gtttcaaatt taagattcat | 780 |
| attcaagata ggtgaaagac catcatatat ttaaagatgg agatgccata agaatataaa | 840 |
| accgtggata taaattcact tttaatatc ttttaacact caatctttca ccggatgacg | 900 |
| gatgaaatca atgtggatta cacatcactt taagcgagat tcatttccaa agttatgat | 960 |
| ccacattaat ttcattcagt aaaaaataa gtgttagaaa gagagtgttg ctagaataaa | 1020 |
| taataacagt ttcgtctcca tttttatatt gttgctgttt tttctatata agataagatt | 1080 |
| tcttcttgac agcatgaaaa tactttaata ttctggcacc atggattagt tgcatacatg | 1140 |
| aattaggtgt gcaccattag ggaactaaaa aagcctcaaa gtgattgacc tgcacatctc | 1200 |
| ccatatattt aacaaatcat cattcataag aattttttat tgccacccat attgtgctgc | 1260 |
| cagattttga ttaattaaat tgtttggtct aatgatgttc gtgcaatgca acaagtaaac | 1320 |
| aatgccacaa atttcttat agtgaaactt ataaattacc ttctttgtac tattttaagt | 1380 |

```
gttattaaca aatcataatt cattatcaga aaattaaaat aagcaataac caaattaagt    1440 ttatatttt  aaggtttagt tagaccaaac caaaattcta agatgatatc aaaatctatt    1500
taggaattgt tggatcacct attatcaaaa ttttactatc gagtcactgt tcagatctaa    1560
acaagagaag gacttgtata ttatgagtca tagagattaa cattcaaatt ataaaatgtg    1620
gaataggcca aacttgagtt gttgtgaatc caacaactat cacctgaaaa atctatacat    1680
gtgaatcagc caaagtatga accaccccaa atgcctctca ccctttctct ttgcacataa    1740
aattaagtaa acataaagaa tcagttacaa gagtcaagac agacaggaat agtgcatgca    1800
tttcaactta gataatcctt cttatttct  taactatacc aactccaaca ttgcatgatt    1860
aaaccactgc caaatcatta ttccacattc ctttgtgctt atatatagtc ctctaactca    1920
agtcaattct caaatcaatc atatctgtct tattaacttt gatcatcttt agcattccat    1980
tttcatcata tttagaaaac atg                                           2003

<210> SEQ ID NO 12
<211> LENGTH: 2003
<212> TYPE: DNA
<213> ORGANISM: Medicago truncatula

<400> SEQUENCE: 12 ttttttgaa  taaaatgagt ttttatgctt tgttttagc  aatgttttta aacgcggacc      60
ggtgatcgac ccgttcaagg cactggtcgg accgcatgac tattaacccg gtctatataa     120
aaatatttat gaccaaaaat tacattatga atgaaatttt gttaaaaaaa aaaatcatgt     180 cattttttt  ctatttaaag ttcgtacatt aaaaaaaagt atatttacag ctgcaagttt     240
gtaagttaat ttcttaattg catcacaatt caagctaatt ccaatccaaa ttcaaattag     300
ttcatacatt aaacaatagt actgcatcaa aaaacttcac aaataagttc taattcatat     360
tccatcttta aaacatagca tgttctaaac attgttggaa atcaaaatat aacagactta     420
caaacccaag taagttacat ggtcaacaaa aaacagaaac tcaaataagt tataacaatt     480
cactaatcaa taaactattt atgtccatgg agtcaaattg tcatagtctt aaaatccata     540
ttcatcatct tcatcggttg agatgggaga ggagaacggc ggtcgaacca ctgacccggc     600
cgggtcacat cgggttaatt gcatatccga tcctgtagcc tgtccgaaca gctgcatctt     660
ccagtttgcg agccgagcgg tccgaccaac caggtcggtc cgggttttaa acattggtt     720 tttagattct tggtttgatg cgtagtggag tcttttttta ttttacacac attgcttata     780
ctttactcaa tgcttccaca tgttgaagtc ttgaaaatat aataattttt tgtcgttgaa     840
cataaaatat tattgtaaat aaattacagc ctatgtttgt ccaaagttta agtataagat     900 ttcacttct  taaattaaa  ataatgataa cgtgtttcag tttgttataa gttaatgact     960
acttgtaatt aattaagaag gtaccttact aatatgcatt gacttgtaat tcaagaagac    1020
tgtatatcct cgccagctta acggttgcca agtaatcatt gaaaatttga atgagttca     1080 cattacatca ttgcaaacga caaattattc tgtattcaac ttgtaatctc gaacagatac    1140
tcttagaaat tgcgaggtca ttgcaatata gtcttctctt cctatctttt gcagtcggat    1200
taagatgacc tgtaacttga ttatatggtc ctaaggagct aattgataga aaaattatat    1260
gcttaagtca tgagaatgat ttttctggtg aagtcaacat tgtagcatca aaagtgtagt    1320
gagtagcacc tcactatta  tacggtggca tcaaaagttc agtctccata gtatcatcaa    1380
tttatcagat taacaagatt gcacttaatc taattttatc ctaccttgtt ttaagtgtaa    1440 cacccccagaa agtgtaacac ttaagactat cgcataatat catcaactat gtttgcatgt    1500
```

-continued

| | |
|---|---:|
| taaagatgtc aacgataaaa tagttcatgt aagtccaaga tgttgcaaac attactagat | 1560 |
| gaattactat tgatcattaa tcagcaatca acaatttaaa aatgaatcga acattaagat | 1620 |
| caaaattaac ttttcaaaa aagtcagttt cctgactgca tcgtagaagc tcccttgatg | 1680 |
| atattagtta tataaatata taacttcctt gtatcagtga tcatgacaat gaaagatgca | 1740 |
| tttaccattt atttatgcta atatattcaa acacttatta ctactttgat atatatatat | 1800 |
| atatgaatat atactttacc ttgcaactac tgattattat ataaattaat aaggtcaaca | 1860 |
| agatttatat aaactaatga gacagaaaat ggttttcct agtagttaca aatcatatta | 1920 |
| atgtggaaca ctcttatata agttcctcca atttatatgt atacattgta agataataaa | 1980 |
| gaaaagtttg tgttggttaa atg | 2003 |

<210> SEQ ID NO 13
<211> LENGTH: 2003
<212> TYPE: DNA
<213> ORGANISM: Medicago truncatula

<400> SEQUENCE: 13

| | |
|---|---:|
| gtgatgaaag taatattaat taaagttata aagagaaaaa aaagtaatta atattgtatt | 60 |
| taaaagtgaa atgactcagt tattttggga cttttttttt ttgaaaatga ctcagttatt | 120 |
| atgggacgga gggagtagtt gttaaactat atatgaagtt ggtcaaatta accttaaac | 180 |
| tatatgtaaa aagggaagaa aaaaagtta atttattgtt attattatta ttgaaaacat | 240 |
| tggttaatgt ttattgttgt gtgtgtgcat aagtgatttg gatttgtatg tgtagggttt | 300 |
| cacaaagttt aaggattaca tattattttc ttatagctta gagactaaac aggaataata | 360 |
| gtcatagttc acgacttttg aaagttgaaa cacaacatat tcggttaagt agaagtaaaa | 420 |
| catagtgtat aaaatgcagg tttagtaagt gttatacaaa tcttagctta gaactaaaaa | 480 |
| aatcatacaa taccactaaa gccccttcac acaacggtgg aagataaag gaaaatacca | 540 |
| atcatagaat ccaaacaatg aaatatcatc aagattaaag aaaattctta actgccacac | 600 |
| aaaatcataa aaccaaacta tgcactatac tgttttttaat attctcatat actgcatcat | 660 |
| cttgccactt agagcaattg tttaacttca cgaggtggga ctatagcaga aattttggac | 720 |
| ttttacaaag gacaattata gtggctctgc cactctcaat aaaaactatt gtaacaacta | 780 |
| acaagtgttt ttttttttctt tctataaatt atttcagctt acagcttatt gtcacacaca | 840 |
| attctaatta tgtttgttaa actcaacaaa ttttaacttc cctttgttgt catcatagtt | 900 |
| tcaactcatg gagtgtgtct ctaacaaaca tgttttttgtt ttcatgtttt gtcttgtgtt | 960 |
| tcttactcca aatgtgtgct ctcaactcta ttacaacttc tacattagaa cttgtccaaa | 1020 |
| cctgaacaga attgttaaaa ataatatctt gtcagctata gctaatgact caaggattgc | 1080 |
| tgcttctctc ttgcgccttc atttccatga ttgttttgtc aatgtaatta agtctcttca | 1140 |
| tttccattat ttttacact gtcaattaat ataccgttgg atcgttaaaa ttattcttta | 1200 |
| ataatattat gtgttgattt gttatttcat ttttgtgtta catagggatg tgaaggatct | 1260 |
| gtgctactgg atgatacaga cacactaaaa ggggagaaaa atgcacttcc taataaaaat | 1320 |
| tcattaagag gatttgatat aattgacaaa ataaagtctg atttagagta tgcttgtccc | 1380 |
| aacacagtgt catgtgctga tatacttact ctagcagcca gagatgctgt atatcaagta | 1440 |
| agaactcact actttataac tatttgaata agtttgaaga agctgattca atatatcatg | 1500 |
| catgagcaat acattttaa ttactgcatg tttccaacat attgttactt aaaattttg | 1560 |
| tattttttct tttccagagt agaggtccat tttgggctgt gcctcttggt cgtagagatg | 1620 |

-continued

```
gcacaaccgc gagtgagagt gaggcaaata acttgccatc acccttTgaa cctcttgaaa    1680
atattactgc taagttcatt tccaaaggtc ttgaaaagaa ggatgtagca gtgctctcag    1740
gtttacttcc ttcacaatta tttgtatgaa aatgtttgta acataacatg aacaacatat    1800
aaaacccatt agagttggcc tagtaaaaga aaacaatgaa tagcaaatat atgtctcata    1860
taattttatc tgataaggtc atcaaaacat ttctctatta atgtttaaat ccttaactcc    1920
aaaagtttgg gctagtagta aaaagacata ccttaaatcc ttaaaatttc attgaatctg    1980
aaaaaaaaga atttttacat atg                                           2003

<210> SEQ ID NO 14
<211> LENGTH: 2003
<212> TYPE: DNA
<213> ORGANISM: Medicago truncatula

<400> SEQUENCE: 14
ttttatgaaa ttttaattac aattgattcg attttaatta aaattttagg tataaataat      60
atataattta tatcttcata ttataacaaa ctatacttat cttttcaat tatacgagca     120 atataacaaa tataatatct ttcaaaaata taaacataa agatcatatt accaatcaaa     180
actagagata gaaaatagta ttggacatat ttttgatgtt agagacatgt ggtcagaatt     240
aacataaaga caagaattag ggcatatttta aagcacgttt gttttagatt ttaaaaaaaa     300
aaaaatttgt atttttaaaa atggattttt ttagaaattt acttaaaaat agtggaagtt     360
atttcaaact catttagcat aagttaaaaa tgagattttg gcatttacta acttaaatat     420
tcattgttag atattttaca tagtaaaaat cacatatttt acaaatttct tgttaaaaa     480 aattgtaaca aaaactatt acactgtaaa aatctattttt aataaaagat aaaacaaaca     540
ggcccttatt cggtctaaat tctcaaacca atttcgtcac caaactttca atgttttaag     600
agacagaatt tctctatatg taaacgtgac tttagggcgg acagttttgg gaagagaatt     660
ccaatctcct taaacttaga gtttgtgaaa caggaaagtg gaaagtgggt agcatgtatt     720
tcctaaatcg gaaagtgggt ccccgactct cctttcacag ttctcatatc tgtgcatatc     780
ttggttgttt tttcaggagg actcatgttc ttttctctgt ctatactttc tcacctccac     840
atcactaagc ttctcattgt atctaatata agttttggct ttatttaaga aatcgttgag     900
atatattgat tcctctactt atttggccat agcaaagtcg cttcctctta ggagaccttt     960
ttacagtaaa tatatattca gttttcatca attccttgga cttgaacgac ttttttgtta    1020
aagcttacgt tgtatttctt gagtggttca ttattggatt gaatgtaagt tttagttttt    1080
ctgtactggt gaggtgaccc gaccgtgcaa cttgtgactc gtttctctct tccatgcgga    1140
taatttgagt gtaagttttt tgtatgattg aattgtgacc cttttttttcc tagggaaaac    1200 tactattat acaaatagat aaagcttcct agatttgaat ttgaaattat aactgtagaa    1260
aactaactat acttatccat tcgatttgaa tttcgaatgt gtcttgaaaa tatctgttta    1320
tttgacctta tccgaaaaaa ctgccctccg agagattatt cgtgtcgaac cgagacacat    1380
gccttccaat atctctagca aatccaactt ttgataagga taaagaaca atttcttcga    1440 ttacaaggtc aacctatttt aaccgtattt aatgatagcc tttaaaaata ttggctaaca    1500
ctccgccact gcccttatc ctaaatattt atcataaaaa acaaaagaa aaataaaatg    1560 aaaaagacta tgcaattgct cacaccttat catttccttt tgcatttgtc atgatatata    1620 ttgtttttt taaggggggg tacatattgc tgtggttttt tttttttttt ggagtatttt    1680 tgttttgaa agaaataggg agcatacact gttatacagc gactttgacc gccattattt    1740
```

| | |
|---|---:|
| ttataggggg ctatcttata tcttgttatt tgaaaaattc aacggtcctt tcacactgaa | 1800 |
| tttctgtgtt tctttatttt ttatttttt taatatcgt gaagggcgag tgcgtatgac | 1860 |
| ggataataat gtgaaggtgt agtgtggaaa aagttataa ggattatata tataatttca | 1920 |
| attattgtct ctacccaaaa gtgggtggac caaagtagat aaatagctgc aaatttcttt | 1980 |
| gtttgttcat acagcaaaaa atg | 2003 |

<210> SEQ ID NO 15
<211> LENGTH: 2003
<212> TYPE: DNA
<213> ORGANISM: Medicago truncatula

<400> SEQUENCE: 15

| | |
|---|---:|
| aaataatgta tgtggtctat aataaagacc atatacatca ttaattgaat gaacttaaat | 60 |
| tgtatatttt ttcttataat agtgaccgga gggtgtattt tttgaataga gaaatatgaa | 120 |
| aataaagagc tcaaccaaca caatattgat ctaataaata ttaatactaa tggttatgtt | 180 |
| aaatcattta aattaatata attaattgaa taactaaaat aataactatg taattaaata | 240 |
| aaataaaatt aatggagtgc aaaaaaaaaa ttgcaagaga tttgataaat ttaggatcat | 300 |
| atcttacttt taaatataat caactatttt ctcttctcaa tttctcttat aacgaacgat | 360 |
| tattaaatat aatattttt tagagaatat attaaatata ttttcgctga atagtgatat | 420 |
| tgttgagtc atttatgata tcttttgtga caacatattt ttttctctat tattgataaa | 480 |
| aaaaaaaaaa aaaaaagag aaaaagtatt atttatactc aagtcataag ggatgcaaaa | 540 |
| tgaggtttgt taaaaacaga actcaatggt atcattcctg attggtgggg aaacattttt | 600 |
| tgcttactca tccttgaacc ctccctcatg ctggctggac cttccccctt tcctattctc | 660 |
| aaatccacat cataattaat cgtgttaatt aaaatcagac taaaaaagca ttgaataccg | 720 |
| gttcaaggtt taatgttctg atcgggttga accagagtga tcagaccggt aggtggtaac | 780 |
| cactagttca aattcaattc aatgtttctt taccttttgc tgcaagtcac gtgctaagaa | 840 |
| agaatcatat ttatttattt attcttttc tttatctaca gtttttaatc atttatctca | 900 |
| aattgtccat atggtgaaag aaaatactaa gtcaatgttg tcgttaagct tagaaagaaa | 960 |
| gaaaaatagc ccactagtca tccatatata atatactata cgttgttgtt atttcttaac | 1020 |
| tttataatta gaagaaaata caacttagac taaaatattca cccaaaaaaa acttggaata | 1080 |
| aatacccaaa ttagcagaac ttttaatatg gatcatcttc ataagtggtg catcatggaa | 1140 |
| tcgtacttaa aaaatgttta aaattaaaac aacagctgac gtcgtctctc ggttggagat | 1200 |
| gttaataatc ctcctcattt ttacaattga aatagtgact taaccgatag tggtgtgatt | 1260 |
| aaaaaaaagt agaaaataaa tatgccgctc atattgaacc aacatagata atgagttttt | 1320 |
| atgtgggact atcgttgaaa tttctaaaat agtaacaact aacaaggtgc cactgtgatt | 1380 |
| ttgtcaaatt agaacatgt acattttcac tctaaaacat aagcaaaggg caggtcaact | 1440 |
| atgaaactta tgtttgctag aaaatgacaa ataaggttgt ctgcatgtgt aagctagtta | 1500 |
| tgtcaattgt caacgcagaa acattcaaaa cctgataaac tcaagtgacc aagttacatg | 1560 |
| tcgtgatgca ccattaacta tattttctta ttgccatgat ttattaaaaa aaaaaaaaaa | 1620 |
| actttcatac tttgtaacac ttcctatttt tcatataata taatctcaat agtatcacat | 1680 |
| tgctagccag tttcaactct tgttaacatt tgtttaattt ttatattaat gtgattgttg | 1740 |
| acttatatg ttcttaatcc tactggttca ttattttata cttatgttca aatgaaggaa | 1800 |
| tcatcatcgt tgtttgctag ttgtaattct ccattactat gtaattgttt atttatttga | 1860 |

-continued

```
tcttatacta aatgaaatgg tcactggata aattaaagaa ttcttaacta tgttgacttt      1920
ttctccattg atgtaatgga ataaaatgag gattgtaatc ttttttattca gcatttgaaa      1980 gtgtcatttt taggttgatc atg                                              2003
```

<210> SEQ ID NO 16
<211> LENGTH: 2003
<212> TYPE: DNA
<213> ORGANISM: Medicago truncatula

<400> SEQUENCE: 16

```
ctcccaaaaa tcaaatctta ctatgttgta tcattttca actaaagttg gttaaatcca       60
tcgcatttca gacgtttgtg actactacac aagaggttag tgaacattta cctaaatctt      120
tgatgtttga tttatttgtt ttattcttca tcatttcggt atctaaatcc aaaatgtgta      180
tgcaaagtta aagtttgat ataattttat cattgtttca tatatatgtg ccttcaagct       240
atatgatagg tgaaggatgc cccctttatg atgaggagaa atttaccact tatcatcttc      300
cactccctca tgtgaaggtg agttgtttgc tctattttga gaacgtaaaa ctaattctct      360
tcggtcactg tcttttcctt aggttaagaa tctcatatta cgatgtatag agaacttaga      420
tcaagaaaag aagaagaaaa taagacccaa gttttgaggg atcttgtcca gtcgactcct      480
tcacacaaag gtgtttctcc ctttgggacc accccctaca atgccatccc tcctttgacg      540
gtactttcat cgcctcatat agatgcaaat gaagatgcag ggctgctcaa agtcaaagac      600 ataccttga gtggatttc tccgtcatgg aaaaagactt ggacataatt tgttcttcgt        660
tctgctcttc gttctccgtc atggaaaaag aactctcttt tacttgattt tcaatatttt      720
ccatttatac ttgtgctatt tcacacctttt acttccat ttatacttct tcttagtcgt      780
ttaccttcca tattttttt gtaagtattt tttctacgaa attcttaatc ttaactcatt       840
tgcttaatct ttctttgttt cgtcccgatc aaattccaaa aattgaagcg tgttttctg      900 atggattgct acaatctcaa tagagataaa agggaaattc taagggccta agagatatgg      960
aagaggaaaa tttcacaatt tcttaatcat ttctcattat cccggccacc tcagaatgtg      1020
ccagtccatt ttgttggaga gtccattgga tgcaattatc tgacttcata tattcagttt      1080
gactgtataa attaaattaa atcatgtatc caaacggacg ttgaagcttc taagagaggc      1140
ctttttttga ataaacacat aaattggagc ataaacacgg tgaatataag ataaaataaa      1200
taggttgatg ttggtccaaa catgtatttt tttatcaata caattggtca ataaacttct     1260
caaagaaggt tccatctaga cggatgtctt tgttgaacat ggtggcgtcc gtaacattaa      1320
taattattcg ctctccatgc aatatagtat tattattagg ctttttttaaa aggactcatc     1380 agatgtccca acgagtttag ttcacttgag aattgataat gcataatata tgcagaggtt      1440
agggtttgaa ccccggacac cccatttatt atcattaaag tgaattggtt gcttgacaaa      1500
aaaaaaactc aattgataaa aattgttgat taaaaaatgt atattcgggc accaaaaata      1560
ttaatatctt catttgttaa caaaaaatga taatcttcaa tatttggcct ttttttagta     1620
aaagatttta attctttgat tagtattgtt aaatagtgat tatcatttgt ctaataaaaa     1680
attataataa ataatgtaag tgcagacagt tcttcttcac gtgctaaatt tcacacgcct     1740
aaacagctca tgcatttgga tataattgat ttttgtaatc aatgacgact agctagtttg     1800
ttcaaaattg acgactagct agtttgttca aaataaaata tatgaacgac tactagtata     1860
aataaatatg cctatcattc atcattatat acacactgca taattaattg gtaatccttc     1920
aattgaattt caactttcac atacaaagca attttttggt ggaacacaga agaacaaaga    1980
```

```
aagaactaga tcaagaagct atg                                             2003

<210> SEQ ID NO 17
<211> LENGTH: 2003
<212> TYPE: DNA
<213> ORGANISM: Medicago truncatula

<400> SEQUENCE: 17
ataaatgaaa gattgatata aattatttag atgaaaaaac gattagttaa aaaaaatgac       60
agaggcaaat gtatcaaagt cccgaaaggt atcaaagtca cttactcata aaatataaaa      120
aattgtatga tacccaagca agataatata aaagaatggt tttagtattt agtagaaata      180
attgtattga tccaataagg tttacatgaa aaaacaccaa agtgataatt tgattcttcg      240
tcgccgtagt aaatagtata gagtagagaa atagaattt gtttcttcgt ctttacaaaa       300
gaaaagagtg atttactatg atatgatttg attttgtttt tttagagatt atataatttt      360
attttttaaa atataagaga aaaaatacac ttttttagaa attataagag gaataattaa      420
ctatgacacg ttcacgaaaa aaaaatcctt ttgtagcaaa tcatttatta aaaaaaaaa       480 aaaaaaagc ttaacacaaa aggagaaaaa gaaataataa taacttggtc cagaacatct       540
actattatac ctacaatgat tgggcattat attacaatag tttcacttat atcttaataa      600
tattttaatt ctatattgtc aacctttata tactaaatta atgttttat tttttgcgta       660 aactttgcat tattatttat ttatttgagt attctaatta agtatatatt attttgaaat      720
tcaagaaatg accttatcat ttttatactt catgtcaatc ggttcaaaac ttacatgtgc      780
aatttgtgta tataatccat atcttttta acgtaagaga agttggtatc tttatgaata       840
gaacagtgtt tgacacattt gaggtttacc aaaaattgtc ttttacgaca tacatatttc      900
ctccaaactt caaagcattt agaatcttat tgtttaagaa tgattaattc aagtgtcaac      960
cttacaattc attagcagtt cttgttctct catgccttca aaatttgata gcatctattg     1020
ttgcatttgt atcaattcta attttaagca tacatgatga tctattagac atcaaaagaa     1080
ggtgtaagaa gacactcatt tttctagcca agatattcaa acacatgatg attagaggat     1140
cttcacttgt ttttaaatta ataaaccaac ttggtttcaa atctcaagta cataataatc     1200
caccttatca gacagtgata taataaattt tttacagaaa agcaatacac aattcataga     1260
ctaaagaata aagaactttc cattaaattt aacagatccc aaaaaaaaaa atcactattt     1320
attaattcac taaatacatg ttcacactat ttgtattgga aaaagtttg gccagcaggg      1380 atggttatga agtcattaat tcttttatat tcagtaatca aactttcaaa cacaacataa     1440
atttattaat ttggaataga catctaaata aaaaaacaaa aaatcaatgt ggatgataac     1500
atggtaaact tgcagctcaa gaaatgtgta gacgtaattt acaattaatc tattaaaaat     1560
catttgacca atgcaacata aattgaacta tatcaactta gtacaatagc cagcaactct     1620
ctgtagcttc ccacggctag ttagttttcc atcttctatg caggtaagac ttgctccctc     1680
ttgactctga ttttccact gtttcatatg gttttgtt tatttgtttc catttatct         1740 tcaactgaaa ttttgacaaa gttgactcat ggttctttct gaagtactcc tactattttt     1800 attttattt ttatttcttt tacttctgaa ccacattgat gaaacaaga agctaacatc       1860 ttctttacaa actaaaggca aaacaaacaa ggaaaaggaa aatattaaag tttgacgaac     1920
actatcttgt tgtctggtaa taacttgaat ttgaaatgat ttttctgcag ctgttttgaa     1980
tttactgtca cagccagaaa atg                                             2003

<210> SEQ ID NO 18
```

<211> LENGTH: 2003
<212> TYPE: DNA
<213> ORGANISM: Medicago truncatula

<400> SEQUENCE: 18

```
ttttttttttg taagtcatag tcgcatcata caaaagtaga gattaatggc tcgagataac      60
taagatatat ttaaagagtt tagtgctcga gttatgtgtg tatataaata tgtgtatata     120
tacataggca ttaggcacta atttggtatc atgttatact attttttgtca tgtcatattg    180
gtattgagtt gtacactatt tggtcatgca tataattaaa tgtaaaaaca gttacaaagt     240
aattaacaaa caatcattcg accattcact agcttggata tgcatgtcat attttcatga    300
atatttccca tgcattcacc gtagggatgt caatgggtac ctaataggca gggaactata    360
gtacccttcc ccatacccgt gtttgtaaaa aatgctcgta cctgagcccg tacttttgtg    420
ggtaataatt ttagtgcctt tcatacccga actcattatg cgcactttaa ttataaaaag    480
acaataaaaa acatcaccat tgaaataaaa ctatgatcca attttttta aatcaactca    540
taaatagca gaaatcgtag tatttagcca ataaaaaat attcctcgaa aattaaaata    600
aaaacataca aaatacatat aaaaaagtgc atgctaatat aaacatcaaa ttgatttaaa    660
tcataaattt gtagctcgtg agcttatgaa ggtaaggatg aaacaattac cgtattagtt    720
tttaggttta ggtttatgct tataaatagc taaataaatt aaatacttgt acatcaaaaa    780
taaataaaat atttattata ttatataaat atgtatatgc gggttgtggg gctgggtagt    840
atagtgctca tacacatcta aatttgcagg taattacctg gacccaagcc catatccata    900
aaagcggggg ttttactcta cccattacgg atatttttg cgggtgtcca ttgggtttgg    960
atccaattgt catccctaat tcaccataac acaattcttc tagtcattcc actctttctt    1020
gttttttttt ttacaaaagt caggtcatac atactacact tttggtaatg cactatagat    1080
aaattaggcc tcgtttgttt cagattttttt atagtaaaaa aaatcacttt tctcgtttttt   1140
aagtgtttgt ttaggatttt tagaaaaatc attttatcaa aaaaaaatta ttttggctct    1200
aaaataaaaa gctattaaga ttatcttttc tcaaagtcta ttttttacaa acataactag    1260
gtaggtcatg aactagttaa acatcatttt tttcaaaaaa aaatgatttt tttgatagta    1320
aacaaacata taaaccttta gatttttttt caaaatctct agattttttct aacataaaat   1380
ctattttctt taaagctaaa ataagaaata gtctaatgtg cctttaaatt aatctttat    1440
actatatttta tttaaattaa ttcctctcat ttctccatca gtttaccata aattaattcc    1500
tcgattaagg tgttagcaat agttaccata tatactttgt cacaatcccc tacaatattc    1560
aaccttttct aattattaag gctatccctc ttgagtttat gatgaaaatg gattcacatt    1620
ggtcatttga taatgtaata ttttttttg gttacatttg atgtaatatc taggtagggc    1680
caaaaaaat taattaattt aacaaattgt tggctccata tgtctatgta tcttagtctc    1740
tatctagctt tccattatat gatctatttc cttatatttg gatggaacca cctagtacca    1800
atttgcccga atgttccaaa ccattaatta ttgtctcagt atgtcttcaa gtaggcatgt    1860
agattcaacc taaaattaag gaatttatgg aaaattaact taaagtttat atgaagggac    1920
aaatatggtt gtttgcttct atttattatt taatgtgtat tgtgcttaat tatgcaggga    1980
actaggtaac aaattcagtc atg                                             2003
```

<210> SEQ ID NO 19
<211> LENGTH: 2003
<212> TYPE: DNA
<213> ORGANISM: Medicago truncatula

<400> SEQUENCE: 19

```
tatgcaaaat tgctttgata gactcataaa cagattatct acctaacttt ttcggagctt      60
tttttaatct tttttcatta aatgtcacaa acaccattga tgatgagctt ttcgaaaaac     120
atcctcaatt gcatttttta tgtttttatc ttgatcaata attatggcac ttgaggtacg     180
tccatgcatg cattataatt gattagggat ggacgtgagt tttaaaattc cagaaccaag     240
tggagtcaaa ctcaaaccaa taggccatag cagtagccac acgtttaagg atgggacttg     300
aacaaattcc ggtaatgatt tattggccaa gttgtgtgag ctactctatc cgtctttaat     360
tacaagaaca tttataaaaa agtttgtttt aaaatattag attctttaca aattttttaga    420
tgaatttatt agtcttttt caaatatacc aattttatta atactattat caatttgtct      480
tggaatataa aaatgtaaca ataaatgtat ttatacacaa agggtaatta agtaatagat     540
tatatacatt ttagacaaat atattactac aacaactttt ctcaatacca gtaattttg     600
ttataagggc ctatgaaaaa ggacgaaggg agtactaatt aatcaacata atcgctacat     660
tgttcatgag ttatgatgct ctccattttc tttctacgtt gtcctctcaa ttactatagt     720
tttaaagagt tttaaagtgt aaattaaata attgaaccta ccaaatgtca cattgttgta     780
tttattatat tctcaaagct ttgataatag aaaaataaag aaagtaaaaa atcaagagga    840
tcttcactcg ttgttcattg ttctgattct cctgagaatt aataatgtag tcgatgcaac    900
aagagtccat ttcgaaaaat ttagagtaat gtttgcgagt taagtttgaa gagttaagtc   960
tattttgttg tgcatattta atattatttt tttaaataaa tgacataata gacaatcata   1020
caatattcaa attatctttt taatcaattt agatactata tttagaaatg attaatacaa   1080
aaagtggaaa taacaagaaa atttaaagac tgaaaaaaga aaatatatca ccaatgttag   1140
catctctaat atttagtgac caatttcgca attttttcat ctctaatttg ttgtcgttat   1200
tccaactttt ttctagtaat taaagtatca actcttttcc tccgaaacgc aactccggtt    1260
aacatagttt cttctataat tctattcttt tcatatattt ttcaaacaat ataagaagaa   1320
gacttgatca tattaacttt gttagaaaag gaacaaccat atttttttaa gaagtttaac   1380
taacccatcg aaattggtac gagagaatcg aaactgaaat tttaagagga actcattcag   1440
acaaggaaca accatgttaa tctgtctttt tgaataataa ctccaaatac attgaatctt   1500
ggttcatagt ccggctcaga tatattaata aatccgttct tctataatat tattatttgt    1560
tcaatggaaa ttggataaat aagtattact aaaaaaataa aagcgtttgt aataaaaaaa   1620
tcaaaatgga atacgtgata taaaagaat gatatttccc ttcaagataa taatattcat   1680
agccgccttt ataatggggt tgaaaattat tagacgtggt aaatttgaaa actattagca    1740
tgaatctatg agagaacttt aataaaaaaa atatttgcat agatgtgttg tcaatactga   1800
atagtatcgt ccacataaag tgcgtatttg cttttgtcat atggtgaaaa ccattcaaag   1860
catgcatgca tgtatgctat tcttctttca tataaataca catgggaatc attctctcaa   1920
gcaacagata catccaagta ttagcatcac aaatcttaat agcattacac caagcatata   1980
tagtatatag tgaaaataaa atg                                            2003
```

<210> SEQ ID NO 20
<211> LENGTH: 2003
<212> TYPE: DNA
<213> ORGANISM: Medicago truncatula

<400> SEQUENCE: 20

```
ttatgaacga acatcaggat tattttaaga aaccgagctc gcaagtttgg aatcacaaat      60
```

```
tcattatccg aaccaaacca ttctgaaatc gaacggatta gtttgtgtta gatccaaact    120
tgaatgttgg attgatttaa gtcattggtt tgaacgagtc atctaaaccg tgaacaaccc    180
ttccaagtaa catggctaat tgatatttat gaattcaaaa ttcattaata agattggata    240
gacaatataa aagcgtacaa gattgtactc caaggtgatt aagattcata taataattg     300 atctacgtca acatagtttt ttttttttcta tagacatcag ttatggatcg aaattttgg    360 ccaaatgata agtgatttga gcatctatca ctttggcgca caccatgtta gtggagtaaa    420
tcatattata gtcttgaaat tttatggat acactacatt atgttgtgtg atcttgttta     480
atcaagtttc catttctgtg ttctcttctc tgctgtgttc tggagatgag ttcgaattct    540
tatcatgtct ttctcttata tcactcattt gtctactctt ctcttttata tcagcgccta    600
acagctgaaa gtatgacaag caatctttca gtactatttt tgtcaaacaa taaatcttgt    660
ttgcttccat tgacggttaa tatgcgtcgt ctacactctc ttattagtgt caacttcctt    720
gtcaaataag ttcaaacttt gttcaatgcg gtgcttaatg taccgacttt tctttcatat    780
gtcgaccaat tgttgaatta ttttcttatt ttcttcacca tggtgcagta tagcaattac    840
ttgtcgacca agattttaga ttttttaatt aacactccga ctgaatttca aattatcata    900
acctaatttt cctaaaaact gaagggttaa gacaaaataa aggtagttgt cgatcttgtt    960
ggtccctctg tttgcttgcg tacagatcca agtcattttt catgacctcc atgttgagtg   1020
tattttttct gcggtcagtt tctccccttt aaagaacaag aagaaaagca acatagtaac   1080
ctcaaactta aatgtgcatg ttaatttatc aaaaaaaaat aaaaacgtgc atgttaattt   1140
ctgtgtcgcg tacactttc ttttattata aatataatca taatttttgt tatggatgtg    1200 gttcttttt tttttgtgtg ataaagtaga tgtggttctt atttgttctg ataataaagt    1260
ggatgtcatc ctttttgagc cggtccaaag gtaagggtgg acaattggat cggggtaagg   1320
gacccttaaa ctgaatagta atagtaaaat aatactctct tcggtccaat atataagaga    1380
aatttaggtc aataaaagtt gatgtatttg gttaaaaaat tggatcactg catcaatttt    1440
tgttgacaca aatgtctctt ataaatagga tcggagtgag tattaacgta gcaaacgagg    1500
atatcatggg cttatgggct tatggcactc acacaaatga tatatgatta gattaaattt    1560
ccttttcttc ggtatctttg aaagaaaaa atgaactggt ggttagctaa agcaactggc     1620
actggcaaag caagttctat gcttttcatt ttccttgccc ttttatattt ttcttttcaa   1680
ctaatgagat tttactcact ctcttgtgcc tgtgcagatt acagaattca aggaatcacc   1740
acgaagcttc caaaatgtag cattaattat aggcgtgacg ggaattgtgg gaaatagcct   1800
agcagagatt ttacctctcg acgacacacc aggtggtcca tggaaggttt atggcgtggc   1860
tcgccgtcca caaccaaacg tggaacactg ataattatgt tgactacatt caatgcgatg   1920
tctctgatca aaaagacgtt gaattgaagc tctctccctt aactgatgtg acacatattt   1980
tctatgtctc gtggaccagc atg                                            2003
```

<210> SEQ ID NO 21
<211> LENGTH: 2003
<212> TYPE: DNA
<213> ORGANISM: Medicago truncatula

<400> SEQUENCE: 21

```
atatatatat atatatatat attgtttttt accaaataag aagagagaaa aacataattg     60
tcatcaaagt tatcattaaa tagatgtgca aatgtcattg ctcaatttat atatgtttga    120
tccatagtcc aaaatgacat agaagtagaa tatgtaaaca atcagtttca agatgggtgt    180
```

-continued

```
cttaaatgga tgaaggtgtc atgtgtttta tgaaatacaa agtacctttt catgataaag      240
gaaattgtta attgtacaac aataaggcaa aagatgtagt atgcaataga gtgttagata      300
gtaaagaacc aacaccggaa taaaataggt gtagcagaga tgaaaatgtt gagttaaaag      360
tgttgtaaga ctattaagac tattataaga atatggtga aaactcggct ctggtggttt       420
gggcatgtgg aaagaaaacc ttcagatttt tctagtaagg aaggacactc aaatcactag      480
aggtaaatga atgtttagaa aaactatatc aaaaattatt aaaaaagatc tagaaaattt      540
gatagattga tatgcatgat tttgtctaat gtacaaaagc aaattagaat tgtaccatac      600
acaaacttat ttttcaccat tagatcatta aatttcatca tatttcatca tatttcattt      660
aattaaatag tgagatttat tgatcaaacg atataaacta ctttgtgatg gtgcaagtca      720
tatgttcttt atacatcata tacttaacac tatgatgtta tatgatcact gacactgctt      780
agtcgaatgt tttggttcca tccaaaagca tgttttatat tatcgtaatt tactactgat      840
cacggggcaa aatgtttcga caagaaagga aaaataagaa gaataaacca agaagatcct      900
ttgtaaagca taataatttt agttctttga ataatattaa aataatcaat gggtacccat      960
tgtttaagac attcaacaaa ccaccacgtc aataaaatta tttcatacct actttactcg     1020
tttgacattt gacatgcata catacactaa aacgagggaa ttagttttcc aacgctgact     1080
tcacgacgtg aagtttcatt attatgcaaa taatatattt taatagaaga aaatatttta     1140
ttaattatag taacgctaat tatcatttta caataatcct ccagtgaatt tgaactaaat     1200
accttaaagt tactagatta atcttttcacc aattagatag aatgtaaaaa aaaaaaattc     1260
atcaattaat ctagtgacta aaaatttacc tatttgagat taataaatga agtattggtt     1320
gtttgaacta cagtatatat atatatatta tacattgtcc tacctatgaa gcacaaatac     1380
ttatcggaga ttaataaatg aagtattggt tgtttgaact acagtctata tatatttaac     1440
attgtcccta cctatgaaac acaaattgga ttaggcgtgt ctcggtgtcg gacatgtgtc     1500
gtgtccgaca ccggcacttg taactacact gaattatgtt attttttcaa attattagtt     1560
gtgtcggtgt gtctgtgtcg ggtccgatgt tcgtgtccat attcgtactt cataggtccc     1620
taccaactga gctaagctca acgtgacatg cagaatgtaa gtgctatata taatatattc     1680
atataatcat atctttggta tatccgtgga ttactgacaa ggaacaattt caacaatcaa     1740
gagccaacag ttgaagaaag catccaattt taacggttgg acaataaaat aaactaatag     1800
atgcaaggta cacaaaaagc acatggtttc tataccatgt tagtagttaa agaatatatt     1860
cttctggaaa caattgttaa tggttatata tacatggaag gatccaactc ttctcatcaa     1920
atcacaagca tttgcaaaca caaaactata tttgtcaata caaactacct tccattttt      1980 acatcaagta gaaaagaaag atg                                             2003
```

<210> SEQ ID NO 22
<211> LENGTH: 2003
<212> TYPE: DNA
<213> ORGANISM: Medicago truncatula

<400> SEQUENCE: 22

```
cgtgtttcat agataataag tcgtatttaa gtggagaata aaaaagggtc ataaactcat       60 aatttaaccct ctccattttt gactgattga aactttagca cacaccaaaa aaacaattct     120
gctcaagtta tttaattttg ggttaattaa gttttttagtc cctataaata ttcatggttt     180
tttttttagt ccctacaaaa taaaatcaca cttttttagtc cctttgacat tttccttaag     240
cattttaggg accaaaactg ctgatgaaat ttttttacaa ggactaaaag tgctgatgga     300
```

```
aaatttttata gggactaaaa atgttgatgg aaaattttat agggactaaa aagtgtgatt    360 ttatttttata aggacgaaaa acaaaattgt gaatatttat agagactaaa aacttaatta    420
accctttaat tttaacccat ttttgtactc taacttttaa aagggatttt tgaactttct    480
ttctaatttt catcccattc ggattaaaaa gcaatatat ataaaaatat tcaatagatt    540
aatttttcac acatacaagc acataaaata cacagcgagt gcgatacaaa tattttttcgg    600 tgttttacat atcaaataga caaatatcta atcagaacac tattaatgtt catattttaa    660
aaggaaaatg ttacatagac gccttttaat tgcatacacc cttgtacacc ccatgtatta    720
ggaagagaga agagaagaag aaagagaaag tgtacttgtg cggggtccat atgactacat    780
gtcagatttt tgtgtgggtg tcaaagggtg tattgccacc tacagggtgt ttatgtatca    840
taactcattt taaaaatagt tgcgactgtt caaatatta ttatgtgggt acataaaaaa    900
ttgcatcccc gtatttaaac acatcaaatc cgtaacgagt atggtgcaaa tatttaacgg    960
tgcgatacga atatttaact agtgcctccg gggcattagt taaggacctt aaatggtaac   1020 ttttatgaa gtttgtgta atcagtgcat tgaaaaatga aaactttgac atttttaaag   1080
aataattact taatttagta tacttaaata atgtcctgag gcactcgtta ataagatcct   1140
aaataaaaat atttaaga gaaacattat attaatgttg atattttgaa aatagtcatg   1200
agttttcaaa attttatcca atcgactttc tcatatcaat actaataatt tttatttaat   1260 attttttaaac atttcacaat attatatatg taattatttt ttataaaatt atcccaatgt   1320
tatgcgaccc atatgaatac acaaatcttt tactagttgt cctcgtgagc ttagttctgt   1380
tggtaaggac aatgcataat atatacaaag tccgaggttc aaaccccggc caccaacaaa   1440
aaaaatcttt tacttgttttt ctaataaaat ttaaattata atgggattat ttgaaaagca   1500
tgctttatat tatgtaactt cctactaaac atgggacaaa atgttgtaaa acaagaacaa   1560
aaaaggaata acaaagaaa atctttgtaa agcataataa tcttgttctt tgaataataa   1620
ctaaaataat caatgggtac cctacccttt gtttaagaca ttcaacaaaa caccacgtcc   1680
aataaattaa tcctaaccta ctttactcgt ttgacatgca tatactaaaa cgggggcatt   1740
aggcgtccaa taataattt aacacatttc tctcaaaaaa aaaaaaatta acacatttaa   1800
actactagat gcaagagaca caaaaagcac atggtttcta taccatgcta gtagttaaag   1860
aatatattct tctggaagca attgttaatg tctatatata catggaagga tccaactctt   1920
cttatcaaat cacaacattt gcaaacacaa aactatattt gtctatacaa actattttt   1980 acatcaagtt gaagagaaaa atg                                           2003
```

<210> SEQ ID NO 23
<211> LENGTH: 2003
<212> TYPE: DNA
<213> ORGANISM: Medicago truncatula

<400> SEQUENCE: 23

```
gttggaaagt acttttcttc attgccttct caacaagaaa atgttcaact tttcatgctt     60
gaaggggttg gacattgtcc tcatgatgac aggcctgaat tagtccatga aaaattgctt    120
ccatggttgg ccactcttta aaattcatag gaaacacatg cagtactata caaacctttt    180
atagtttata attggtgact caaacctcat aaattgtcac atatattcca tatgtataga    240
ttatgttgtt tataaattgt ttgtattcat ttacaacccc aagtctcttg gaggaagat    300 aggctatgat caagcatggt gagagaactt acatttaaaa catttttatat taaatcccaa    360 aatacgttgt atcaagaagc ctaacaatga ttatcaaagg ataagagcc tataaacaaa    420
```

```
aatgtttaaa aaatggtcta taaagaatga tcatttgatt gattgtccac aatagaacaa      480
catttaaaaa ctacttgata ctacattagt tcattcattt ctctttgctt tggtgttttt      540
caccccaatc atgtcaccat ttcacttata aaacaagaa tgactattag cttaaatttc       600
taaagagtga cgttgatttt ttattttttt tttccttctc ttttctggtg atatatcaac      660
atcgctcttt ataagcttac ggtcattctt atatttcatg tgattttcaa atgttttga       720 atggttctct aaaaaaaaaa tgttttgca tggttgtttt attaattttt ttaaatataa       780
agttgagttt ttcttattgt tatttcactg aactagtcgg ctttgaaaac agagaaataa      840
atttatcgaa atgaaaatca gagactaatg aaatccataa tttcatttta atgtgtatga     900
taatgtcaac aataaattgc ttgtagattt actcatccgg aacttatttt ttaacatcaa      960
tcataatcat ttttttagtt tatttgatag ataaaaattt aggtgagtgg gactttggag     1020
gcttaccaaa gtcagccctc aaagctcaaa gagtgtttac gaaattattt acatatcaac     1080
caccaaagag atcctcacac ctatattata atcttgtgaa tgagtcaact ttgtaccaac     1140
taagccaact tttattagct taagttttta tgtttaatca attgaattta atcaaatcaa     1200
cattaacttg ttcatgaccc tttaaaaata aaactagttc atggcttcat gcacattag       1260 cttataagac aagttaagct aagttgagtg agctgtgtgc ttgtgaactt tataaagcaa     1320
tttcattttt aagttatctt taaccggata cattagtcga aaaatgaatt agactttaaa     1380
taaattcaag taaaatttag ataagataag agtgtatttg tatgaaagaa tttgtaagtt     1440
aatttatgtt tagagggtat ttctatgtat attttattgt ttgaatgata aattttttgaa     1500 agttgatata taaatttagt cccacaaaat tttaagaatg aacaattta ttaacctatt      1560 taaacataaa ttttgaaaca aaagaaattc atattatacg tttaaacttc ttaaaacttc     1620 aattttttcaa ttattttaaa aaggttaatg tctatatatg gcacttggca gaaccacgtt    1680
tgttataaca cacgaagtct ctggaagagc ttggagaatt cttgcactta gaaccaacca    1740
cctttccttt ctccaaaaca ctataataat ccagaacatt ctaatctatc gacaattatg    1800
tcacttccat ttcactctct accatccata tgtcatttat agaatcttca agaattatgc    1860
atgcaacatt ttaaacctat aaatacaaca catcagcatt tctacttcca ccaaattgaa    1920
gaaaaaaata tatattttac aacttttctt cctcaagttt caaatcataa actacacaca    1980
tattttcaat tcaaagtgta atg                                             2003

<210> SEQ ID NO 24
<211> LENGTH: 2003
<212> TYPE: DNA
<213> ORGANISM: Medicago truncatula

<400> SEQUENCE: 24
gaataacatg acgacgcacc aaatttgatc tcgttggaat tctatcttga agagtgtgtt       60
tggatgaggt aattgggaaa tttttaaagaa tttagaattc taagcaattt aaattactttt   120 catttctcaa tacttttgtt tggatggagt actaaaaaat ttcattgtca tcatttttgg     180
gcaactttta taaattttaa ttttttgggg ccaaatttta attgttgttc gattatattg     240 ctgaagccctt taaataaaat atattttagg gttgatttag taaataattc ttacaaacat   300
ctataatatc tttcctacaa aataaaatca cattttttag tccctataaa attttctgtc    360
aatattttta gtccttgtaa agaaaaatca ttaccagttt tagtcattgt aaaaaaaatt     420
gatcaacttt ttttgtccct aaaaaatatg attttatttt gtaagcttaa gcacaaaata     480
cttggcgtaa tatttggatt gagagtgatt cttcaagcgt tgtccaaccc ttgagggatc    540
```

```
tcttgacatt attccatttt catcactaaa ctgttagtga cggaaatttg ttaattcagt      600
gatgaacttg aacttgtacc ctctggtcac tattataagt aaaagtcaac ttttttagatt    660 cattcaataa atgatgtatt tggtcaataa tatagactaa atacataatt tattgaatga     720
acctaaaaag ttgattttg cttataacag tgacaggagg gagtatgtaa ctagctttgt      780
gtgtattgta caaactatgc tattaataat attttgcaaa gtgtttgctc accgagcgac     840
ggaaggatcg ccatgacgag cgagggttta ttcaccagtg ggtttctgcc acatcagcaa     900
agtggcccag aaaccgcctt tgcgcgccat ggcgaagagt aggcttgctt agccacaccc     960
tgttttgatt ataaaaaata aaaaacttta tctctgccta tattcgcctt gacttcgctt    1020
caagcttgct gtggcgagcc ttcttgccat ggcctcgctt caagttcact tggccacacc    1080
ctggaaatcc atattttggt gctttatgcc tatgttcgtt ttgtggtcct caagggctcg    1140
ccatggcagc ttagcttaaa ttttcttctt ctttctttgc tctttaaatg ccttggcaag    1200
caatttccta cacaaaaggt tggtataaga tataaaaagc ataaaattga aattattcaa    1260
tattttgagc ttttcatgag atatcttgtg aaacaagtaa ctaaagccta aataatata    1320 atatttaaat gattttgat acttatcacc ttatctcgct tggcgtggat ttagctcact     1380
tagcctactt tctcgcttag caaggctcta actttcttat ttcaataaaa gaaaagaga     1440 aaaaataagg gatatcatgc catttgaatt atataattcg aacaaataag acacaagaaa    1500
ttaataaggt gggaaaagaa gagttttttt gttatgaaga gacaattatg gtttttgtt    1560 tgtgcttttt acaacccgat tcatgctatg aatgatgaaa agagaaagga gaaatatatt    1620
ctagtacaag acacgtatta ttaaatatat gatggactta catgaatgag tggtactaaa    1680
caaaatagca aagtagtctt ttgtgtggac catctaatgt gttagttcac actagtaata    1740
aagtgactta ttttaaatgt gaactatttt gaagacttgt ttaaggggaa gcaaaaacgt    1800
cactggatat gtcaaaagta tgtataacgt caccaaatat gtcaatagaa gaacaactct    1860
cacacgtcac aacacattca tggtcactat aaatactcct tatagctccc acatgtttgt    1920
aatatcgaca ataacatata ctttcattac tactcaaaga gacacaattc attcgcttac    1980 ttaattttg tcacgttgaa atg                                              2003

<210> SEQ ID NO 25
<211> LENGTH: 2003
<212> TYPE: DNA
<213> ORGANISM: Medicago truncatula

<400> SEQUENCE: 25
ttcaaatttt accccctact cacaaattct gtaaactata aattttctgt taattttttt     60
taagaaacaa aactctccca tgattgaata tatcttatta tccccaaaaa tccaaaattc    120
aactttgcat ttttttaga caatttcaaa acttgagttt tccataacac ataaaaaaac    180
taactgtaac ttatttattt atttttttc tttagtaaga tgactactta tataaagagt    240
actattgagt atgttggggt gcgcttatct tattgtagat gtacatttac ctatataaac    300
attgtatgac cttgtaatga atcaataaag aatttcatta ttatctttag tttcttagat    360
aagagtactt agagtaattt agcacctggt ggtgatattc atcacctatc gatggatgat    420
actttaggta ctacgagaaa tatgttatat gtgaaaggtg tataaatttga gatggtagga   480 gataagttat aatgttttaa ctaaaatatt ctaccattca gcacccttag aaaaatacca    540
ctatatagag accacaatct ctagattttt atatatcaaa gactgtaact aacaatatt     600 gatagttttc ttttttaata acttcatttt caaataaaaa ccacgatctt tatattctta    660
```

```
ctatacgggt gaattaaaat taaaattttg attgagagtg gtattcatat ttagtattta      720
acatgattca aatacaatta cctccgtcgg gtggagaaaa ttcataaaaa atctacaaaa      780
agtttttatt tttattttt tatctcttgg tgtttaatag gggtgtttgt ggtaccattt      840
gattcaattt tgaggttaac agtaatccga actataagat aaaaaacatg cggtttggtt      900
aagttgaatt aaaaaacaaa atgaatcaga cctaaccaat gttgtttgag ttgattcgat      960
tttttgtga gttaatctct cgagcctcgt gatacccaaa tagacggcaa actcttccag     1020
agttttaaca ctgctgcatg acaaagtttg gattcgaact aggaccttag ttaagctaaa     1080
agagatccgc gtcatctcat ctaaacacta tttgataata tgctaatatg tttgattaca     1140
ttgacctcaa caattaacta gtttgcaatg attagcaatt aacttcaaat agggttaaag     1200
tgcacaaatc aaagttacaa caattaataa ttaactccat ccgtgataga caaggaatat     1260
aaaattaatt aaactatttc gttgtttcat tttcctaacc ttcactacca attccaacaa     1320
cagaaaaatc ctcaaggata cgaaaatata aacttaagtg agtctactct ttggtttggt     1380
ttgggtggca aaacaaaaat ttcaaatcaa agcgtcagtt tgagtaaaaa attggtcatt     1440
tttagattgg gttgattttg tttgcaattt ttttcttgtgt tgatttggtt ttgaacactc     1500
atagtgttcg atcactatct taagtttggt acaaacaatt gattgattca agtggtaaaa     1560
tacttgagtt ctttaaccac gtggccatgg ttcgatttt agctcatgca tatcgagaaa     1620
aattaggttg gagcgaagat gtgcctcacg agtttctcta caaagattat taaacgatgc     1680
aatgatgaaa attttataac aagggtaatt aaaaaaggg tcttgttaag gtttcataaa     1740
tagaaacaat tgataaattt cacgtagaat attttttct ttctttctat gtttcaatgt     1800
attaaattt aagataagat gatacttacc tgttaacatt aagaagttgt ctataacaag     1860
tggccatta tatcatgtaa cccaataatt aatgtttata accatttgtg tattgaatat     1920
tacttgactt ttgatatcat aacaacaaca ttttcttag ttggtgtgaa tgatactcca     1980
accaaacaag accactgtct atg                                             2003
```

<210> SEQ ID NO 26
<211> LENGTH: 2003
<212> TYPE: DNA
<213> ORGANISM: Medicago truncatula

<400> SEQUENCE: 26

```
gattccactt acatcaacaa gtgcattatt tatactcaag gatgaaaata tcgaagtagc       60
ttcaaagtac taccacattt gtatatcaca agcttcgtga agatattgaa agactattgt      120
tttaatcaat agaggtttgg tcgaaggttc aagcaaaaag atgaacttca taattaatgg      180
agtcttcac attatcataa ggttagcgac aagtatttaa agattgtttg atcaacaaag      240
aaaatagtgc atacaccatg atgagaatat tcattgcact caaaagtata ttcatatata      300
tatatatata tatatatata tatatatata tatatatata tatattcacc aaagtgagaa      360
gaatcaactt taaagaataa atcttttgat gatttattta ctggtggcaa aatgtttgga      420
caatgatcaa agaatatttc atatcatgat ccaaggagtt gcaacacatt tcaatattag      480
ttttggatca aaaggaatca agcaactcac ttttaattaa agaaaaacga tatacattca      540
gttagacaat gatcaaagaa tatttcatat catgatccaa ggagttgcaa cacatttcaa      600
tattaatttt ggatcaaaag gaatcaagca actcactttt aattaaagaa aaacgatata      660
catttagtta gagaatgatc tcaaaattaa gagattgact tcctacaata aaacaaaggc      720
ttggcataat ctagctatgt gccaatagtt ttctacataa gttttgaacc aataggaaga      780
```

```
taacaacaca tgagaagaag gatggaaatg gtccacgttt ttggaaatgt ttttttaga      840 tatattttac ttttgtcat  atcactacaa gacaaaaagt acttacaatt ttgccaaaat    900
ggtttacttt gtgtgcaagc ttctaatggc agcaaaagtc tttctacaca tgagaagaaa    960
gctgcccacg gttttggcaa agctttagga acaaatcca  ctcttagtcc catcactaaa   1020
atacgaaagt acaacaaaaa cgggattact ttgtgtacaa gcttcaatat tacagcaaga   1080
atatatcttt atgggttgtc tataaccaat accacacgtg acatttacaa aggcaaaagg   1140
aaaaggcatc agcttcaagt agagattgat ctcatcaaac agaaaccaac ttgaacttga   1200
tttctacata atgtcttgca ctccaagttt aacagagaag ataatattat ttttatgcaa   1260
ttatgaagac atttgcttct ataaatacaa ggctccaaca acaagaaga  cacaagagtt   1320 caagctaaaa aatcaacaat cacttgtttt tctctacaag tctcaaaact cttctttcat   1380
cactcacact caagctctta taaatctcat aactgaatta ctacattctt gagtaagttg   1440
agttgatttt actttgcttc tcaaactaga tttgagtttc tgcaagcaaa gatctcaaga   1500
gactattttt caacataacc cacttttttt gtggaagcat atttgtctct tcatatcaag   1560
cacacttcaa cccatcacca cattttagaa caagcaaagc atacaatatc aaatactcca   1620
aaagctctct ttttgttctt cattttagaa tactaaaatt gctcttttgt tttgagctct   1680
tttagtaaaa cacaattatt ttattttgat ccaagtaaaa agttattcct tattgggttg   1740
taaagcttgt tgataacaag tgtataaaag caaaggtaga tttactcatt tgcaggaaaa   1800
atcaggatga tctagcaagg gtaaaagttg ctcatttgtg aaataatat  aagaaagata   1860 aattaaagga ttgaaagaag ataaagtaat aaatagttat gagtataata gaaaacaac   1920 attaattatt tcaatttatt attttttcaat tatatgattt taggtaacat gaattcaaag   1980
attcatgatt ttttgttgat atg                                            2003
```

<210> SEQ ID NO 27
<211> LENGTH: 2003
<212> TYPE: DNA
<213> ORGANISM: Medicago truncatula

<400> SEQUENCE: 27

```
tatttatgtg taattatggg tatggtaaac ttcatggaat tgatatgttt atgtgcttaa     60
attcatagtt gttggtgata agttgtttgg tgattttttgc ttaattaatt aagtgtaaac   120
catcaattga tgagtgatta ttgttggaac atgtttaaat tcacttcata aatgattaca    180
taagcttgta tgttgttggg gtttgaattt gtgtggttgt ttgtgaagtt tgaatgtaaa    240
tgagaaaata tgaacttttg gtgaaaaatg aactagatga tgattttaat gtaaattgag   300
gttatgattc ccatttttt ttttttgtgag ggaagaggtt atgatttcat gttaactaat    360
aaaaagtttt ttggattata gaccaattat tcttttttttt ttacaatttt cttattgata   420 attttttta cataaaattc ttattgataa ttaaaatgct tattacacat ggagggtatt     480
aatggtataa atttagagtc tgttttgcaa ggtcacactt gtactttagt gtagggtgag    540
aaaatggatg gattaaattg atttggatgt taatagataa ataaatcaaa ataattcatt   600
agttcattaa caatttacta aaaattctct caaaaaatct aatttaattt atctattaag    660
agtaaagttg atttaatcgg tctatttttt gttggctaaa ggaaactgat attgtacatc    720
aggttcaaat acaaattcaa cattgataaa aatgaagttg ataaatctac gaatgaggaa    780
tgctagcagc actttctttt gagcactctc tattactcac tcttttatcg gatgaaatca   840
atgtatttcc caccatttta tgtgggttcc attttcaaag tgtaggacct acattgattt    900
```

```
cacctaataa aagagtgagt gctagagagt actcaaaaga gagtgttgct aacactcctt    960
gctacgaatg agctcacatt aaccaaataa atagcgaata tggtcaaagg tacattcttc   1020
aaaaaaaaat ggttaaaggt acattaaatc acttaatcaa tatacttaat gaaatatgtt   1080
ttgtttccta ttagagataa ctccgtataa tttatgaaac atattttgtt ttggcaaaat   1140 tacatttta gtcccttaac ttaattttag gtaacagttt gatcctttat tttttttatt    1200
tcaatttggt cctttttatc cattttcata tgaattttta agcttaaaat tcatgatttt   1260
attttcttat ggtccttcag tcttcaaatc tatgatcctc gtctatgttt gcattagaat   1320
attagatttg aagcttaaaa atgtatataa aaatggacaa aatggaccaa attgaaatga   1380
aaaaaagata aagaatcaaa ttgttactta aaattaagtt aaggaaagtt tatcattttg   1440 cctttttgttt tctatcatag tttgaacctt ttaactcctt cggctccttt catccttaat  1500
tcaaacgagt tgaattacca aactcgatca ttctaattat tgtgggcagt gtaagctata   1560
cacattaata agaattcaag ataactaatt tttctgaaga agttagcata ctttaaaaga   1620
catttatata atggagtgtt ttttttttt tttttttttt tttacagttt ataatggtag    1680
gagttaggaa tatttattac gcaaggacta attaggtgta ttattttaga ctcgaaatag   1740
aaaattactt aattttgaaa tacattggaa aaagtagcaa aagataaggt agtttgttta   1800
tagttgagca aggtaagtca aaaatgtcgt cggttaaaat atatgaagaa cgtaaccata   1860
tacgtcattg cagccaccaa taagcatata tataagtagc ccttcactct aattaagctc   1920
accgatcata gtattgtttc tataacataa aacataacat ttctagcatc tacaagaaag   1980
ttgaacaaga actaaaaata atg                                           2003
```

DISEASE RESISTANT PLANTS

This application claims the priority of U.S. Provisional Appl. Ser. No. 61/080,633, filed Jul. 14, 2008, the entire disclosure of which is incorporated herein by reference.

BACKGROUND OF THE INVENTION

1. Field of the Invention

This invention relates to plant disease resistance. More specifically, the invention relates to transgenic plants having increased resistance to plant disease.

2. Description of the Related Art

Lignin is the major structural component of secondarily thickened plant cell walls. It is a complex polymer of hydroxylated and methoxylated phenylpropane units, linked via oxidative coupling that is probably catalyzed by both peroxidases and laccases (Boudet et al., 1995). Lignin imparts mechanical strength to stems and trunks, and hydrophobicity to water-conducting vascular elements.

There is considerable interest in the potential for genetic manipulation of lignin levels and/or composition to help improve digestibility of forages and pulping properties of trees. Key enzymes in lignin biosynthesis, including caffeic acid 3-O-methyltransferase (also known as caffeic acid/5-hydroxyferulic acid O-methyltransferase) (COMT) and caffeoyl CoA 3-O-methyltransferase (CCoAMT), have been targets of these efforts (Meyermans et al., 2000; Zhong et al., 2000; Guo et al., 2001a; Ye et al., 1994, 2001; Do et al., 2007). COMT and CCoAMT suppressed alfalfa lines have increased digestibility (Guo et al., 2001a,b). See also PCT Publication WO 01/73090, which discloses methods of modifying plant lignin content and composition by transformation with DNA constructs that affect expression of COMT or CCoAMT.

*Phymatotrichopsis* Root Rot (PRR), also called Cotton Root Rot, is one of most destructive diseases of cotton (*Gossypium* spp.), alfalfa (*Medicago* sp.), and many other dicotyledonous plants. PRR is caused by a soil-borne fungus, *Phymatotrichopsis omnivora* (Duggar) Hennebert (1973), (formerly termed *Phymatotrichum omnivorum*) and causes significant economic losses every year in the United States. Hennebert (1973) named the fungus as *P. omnivora* (Duggar) Hennebert to emphasize its morphological affinity to *Botrytis*-like Ascomycetes. *P. omnivora* has a very broad host range and attacks almost 2,000 dicotyledonous species, but interestingly it does not cause disease on monocotyledonous plant species, including maize and sorghum. The disease is economically important in cotton, alfalfa, beans, peanut, sweet potatoes, ornamental shrubs, and fruit, nut, and shade trees (Lyda, 1978; Lyda and Kenerly, 1993; Streets and Bloss, 1973). Other important fungal diseases of, for instance, *Medicago*, include Anthracnose (caused by *Colletotrichum trifolii*), Phoma Black Stem (caused by *Phoma medicaginis*), Phytophthora Root Rot (caused by *Phytophthora medicaginis*, also known as *Phytophthora megasperma* f sp. *medicaginis* or *Phytophthora sojae* f sp. *medicaginis*), Sclerotinia Crown and Stem Rot (caused by *Sclerotinia sclerotiorum*), and *Aphanomyces* Root Rot (caused by *Aphanomyces euteiches* Drechs.) (Graham et al., 1979; Tivoli et al., 2006), among others.

SUMMARY OF THE INVENTION

In one aspect, the invention provides a transgenic dicotyledonous plant comprising a first selected DNA that down-regulates the activity of caffeic acid 3-O-methyltransferase (COMT) or caffeoyl CoA 3-O-methyltransferase (CCoAOMT) in the plant, wherein COMT or CCoAOMT activity is down-regulated (a) in the roots of the plant; (b) in response to infection by a root-infecting fungal plant pathogen; or (c) during infection by *Phymatotrichopsis omnivora*, or *Colletotrichum* spp. such a *C. trifolii*. In some embodiments, the plant is a legume. In one embodiment, COMT is down-regulated. In another embodiment, CCoAOMT is down-regulated. Where CCoAOMT is down-regulated, the plant can further comprise a second selected DNA that down-regulates activity of COMT. In some embodiments, the plant exhibits increased resistance to *P. omnivora* (e.g. reduced *Phymatotrichopsis* Root Rot disease severity), or to one or more other fungal diseases of plants including those caused by *Colletotrichum* spp. such as *C. trifolii*, relative to the corresponding plant not comprising the first selected DNA. In some embodiments, the plant is of a species susceptible to *Phymatotrichopsis* Root Rot disease, or to a disease caused by *Colletotrichum* spp. such as *C. trifolii*, and in specific embodiments, the plant is a leguminous plant such as alfalfa, bean, soybean, or peanut; cotton, sweet potato, or a woody plant. In certain of these embodiments, the plant is cotton or alfalfa.

In various embodiments, the first selected DNA encodes an antisense or an RNAi molecule. In some of these plants, the first selected DNA may be expressed primarily in the roots of the plant. In some embodiments, the first selected DNA is not expressed in the stem of the plant. In additional embodiments, the first selected DNA is operably linked to a root-preferred promoter. In particular embodiments, the root-preferred promoter is an RB7, RPE15, RPE14, RPE19, RPE29, RPE60, RPE2, RPE39, RPE61, SHR, ELG3, EXP7, EXP18 or Atlg73160 promoter. In other embodiments, the first selected DNA may be expressed primarily in response to infection by a root-infecting fungal plant pathogen. In some of those plants, the first selected DNA is operably linked to a fungal pathogen-inducible promoter. In particular embodiments, the fungal pathogen-inducible promoter is an hsr203J, PVS3, NI16, or STS8 stilbene synthase promoter. In additional embodiments, the plant accumulates 7,4-dihydroxyflavone when contacted with *Phymatotrichopsis omnivora*.

In another aspect, the invention is directed to a method of rendering a dicotyledonous plant variety such as a leguminous plant or a cotton plant, that is otherwise susceptible to *Phymatotrichopsis* Root Rot or to a disease caused by *Phytophthora* spp. or by *Colletotrichum* spp., more resistant to the plant disease, the method comprising expressing in a plant of the variety a first selected DNA that down-regulates the activity of caffeic acid 3-O-methyltransferase (COMT) or caffeoyl CoA 3-O-methyltransferase (CCoAOMT) in the modified plant variety, wherein COMT or CCoAOMT activity is down-regulated (a) primarily in the roots of the modified plant variety, (b) primarily in response to infection by a root-infecting fungal plant pathogen, or (c) during infection by *Phymatotrichopsis omnivora*, or *Colletotrichum* spp. In one embodiment, the first selected DNA is transformed into a plant of the variety, and progeny of the plant are grown such that a modified variety of the plant is produced that is homozygous for the first selected DNA. In some embodiments, the first selected DNA is in a nucleic acid vector that is suitable for use in *Agrobacterium* transformation of the plant. In other embodiments, the first selected DNA is in a nucleic acid vector that is suitable for use in transformation of the plant by microparticle bombardment. In some of these methods, the plant is cotton, a legume such as alfalfa, bean, or peanut; sweet potato, or a woody plant. In particular embodiments, the plant is cotton or alfalfa.

In a further aspect, the invention is directed to a nucleic acid vector comprising a first selected DNA that down-regulates activity of caffeic acid 3-O-methyltransferase (COMT) or caffeoyl CoA 3-O-methyltransferase (CCoAOMT) in the plant, such that, when the vector is transformed into a dicotyledonous plant, the first selected DNA is expressed (a) primarily in the roots of the resulting transgenic plant; (b) primarily in response to infection of the resulting transgenic plant by a root-infecting fungal plant pathogen; or (c) during infection by *Phymatotrichopsis omnivora*, or *Colletotrichum* spp. In some embodiments, the vector is suitable for use in *Agrobacterium* transformation of the plant. In other embodiments, the vector is suitable for use in transformation of the plant by microparticle bombardment.

In an additional aspect, the invention is directed to a method of growing a dicotyledonous plant variety such as a leguminous plant or a cotton plant, that is otherwise susceptible to *Phymatotrichopsis* Root Rot or to a disease caused by *Colletotrichum* spp., in soil or in a field or crop that comprises *Phymatotrichopsis omnivora*, or *Colletotrichum* spp., the method comprising: expressing a first selected DNA in the plant variety that down-regulates the activity of caffeic acid 3-O-methyltransferase (COMT) or caffeoyl CoA 3-O-methyltransferase (CCoAOMT) in the plant variety, and growing the plant variety expressing the first selected DNA in the soil. In some embodiments, before expressing the first selected DNA, the first selected DNA is transformed into a plant of the variety and progeny of the plant are grown such that a modified variety of the plant is produced that is homozygous for the first selected DNA. In additional embodiments, the first selected DNA may be constitutively expressed in the modified variety. Alternatively, the first selected DNA may be expressed primarily in the roots of the plant, or in the stem or foliage of a plant. In other embodiments, the first selected DNA is expressed primarily in response to infection by a fungal plant pathogen, such as a root-infecting fungal plant pathogen or a foliar-infecting plant pathogen. In some of these methods, the plant is cotton, a legume such as alfalfa, bean, or peanut; sweet potato, or a woody plant. In particular embodiments, the plant is cotton or alfalfa.

The invention is also directed to a method of treating a plant that is susceptible to a root-infecting fungal plant pathogen, the method comprising providing 7,4-dihydroxyflavone to the plant. In some embodiments, the root-infecting fungal plant pathogen is *Phymatotrichopsis omnivora*. In some of these methods, the plant is cotton, alfalfa, bean, peanut, sweet potato, or a woody plant. In particular embodiments, the plant is cotton or alfalfa.

Additionally, the invention provides an isolated nucleic acid comprising the sequence of any one of SEQ ID NO:1-27, a fragment thereof with promoter activity, or a sequence comprising at least 70, 80, 85, 90, 95, 98 or 99% sequence identity to any of SEQ ID NO:1-27 with promoter activity. In further embodiments, the invention is directed to any of those promoters linked to a heterologous transcribable nucleotide sequence. Transgenic plants and cells transformed with any such sequences are also provided.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

DETAILED DESCRIPTION OF THE INVENTION

The invention relates, in one aspect, to the surprising discovery that plants expressing downregulated CCoAMT or COMT, resulting in reduced lignin, are highly resistant to *Phymatotrichopsis* Root Rot (PRR), and some other plant diseases, such as those caused by *Phytophthora* sp. (e.g. by *Phytophthora medicaginis*) or those caused by *Colletotrichum* sp. (e.g. *C. trifolii*), while a corresponding unaltered plant is susceptible. This discovery is unexpected because lignin appears to play a role in resistance to some plant diseases (Nicholson and Hammerschmidt, 1992; Pakusch et al., 1989; Carver et al., 1994; Weobel-Kwiatkowska et al., 2007) and it would thus be expected that reducing lignin content in a plant would make the plant more susceptible to plant disease.

Figure 9:
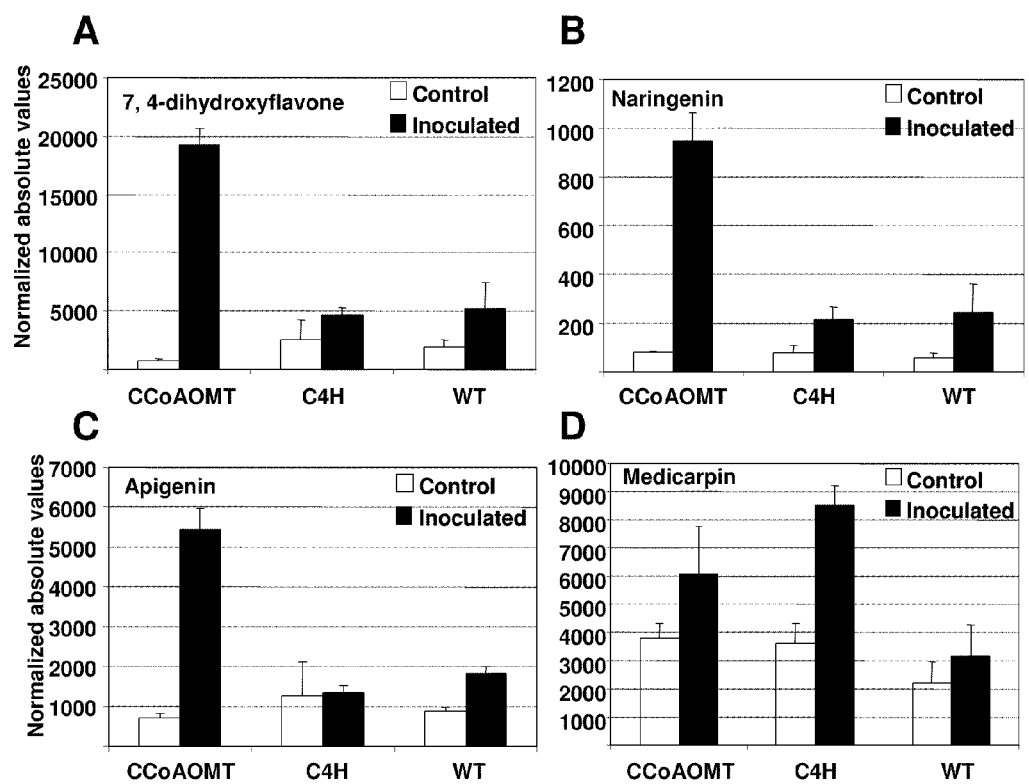
FIG. 9. Flavonoid (A-C) and isoflavonoid (D) contents in roots of *P. omnivora* inoculated wild-type and lignin down-regulated alfalfa (*M. sativa*) transgenic lines. The absolute mean values represent the average of 5 independent samples normalized to internal standard. Pathogen assays were conducted in black soil as described in Materials and Methods using six-week old wild-type (WT, cv. RSY4D vector control) and transgenic lines down-regulated in cinnamate 4-hydroxylase (C4H) or caffeoyl CoA O-methyl transferase (CCoAOMT).
Figure 10:
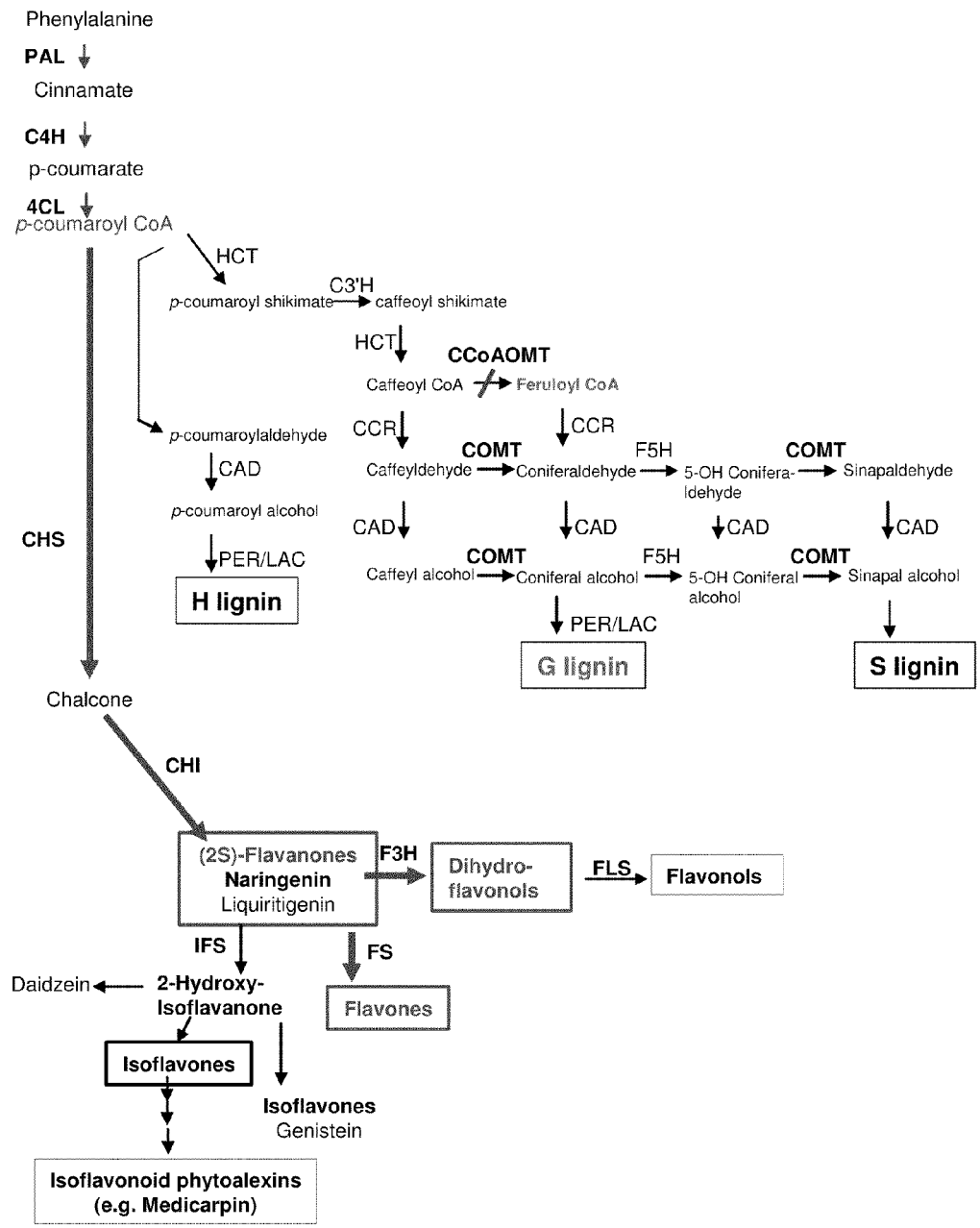
FIG. 10. A model showing the relationship between the lignin and flavonoid pathways and proposed rerouting leading to the accumulation of flavonoids in *P. omnivora* inoculated CCoAMT suppressed roots. Arrows and compounds indicated in green show increased metabolic flux entering the flavonoid pathway. Down regulated compounds and biosynthetic pathways are shown in red. The selected intermediates, end products and enzymes shown in the pathway include: PAL, L-phenylalanine ammonia-lyase; C4H, cinnamate acid 4-hydrolase; 4CL, 4-coumarate CoA ligase; CHI, chalcone isomerase; CHS, chalcone synthase; DFR, dihydroflavonol 4-reductase; F3H, Flavanone 3-hydroxylase; FS, flavone synthase; FLS, flavonol synthase; IFS, isoflavone synthase and IFR, isoflavone reductase; hydroxycinnamoyl CoA shikimate:quinate hydroxycinnamoyl transferase (HCT); p-coumaroylshikimate 3'-hydroxylase (C3'H); caffeoyl CoA 3-O-methyl transferase (CCoAOMT); (hydroxy)cinnamoyl CoA reductase (CCR); ferulic acid/coniferaldehyde/coniferyl alcohol 5-hydroxylase (F5H); caffeic acid/5-hydroxyferulic acid O-methyltransferase (COMT); (hydroxy)cinnamyl alcohol dehydrogenase (CAD); peroxidase (PER); laccase (LAC).

The invention thus overcomes limitations in the prior art by providing plants engineered to be resistant to plant disease, and methods for making those plants. Plants provided include transgenic dicotyledonous plants comprising a first selected DNA that down-regulates activity of caffeic acid 3-O-methyltransferase (COMT) or caffeoyl CoA 3-O-methyltransferase (CCoAOMT) in the plant, wherein COMT or CCoAOMT activity is down-regulated (a) in the roots of the plant or (b) in response to infection by a root-infecting fungal plant pathogen. In certain embodiments, the down-regulation is (a) primarily in the roots of the plant; (b) primarily in response to infection by a root-infecting fungal plant pathogen; or (c) during infection by *Phymatotrichopsis omnivora* or *Colletotrichum* spp. As shown in Example 1, plants that are down-regulated in COMT or CCoAOMT expression, but not cinnamate 4-hydroxylase (C4H) expression (FIGS. 3,10), show increased resistance to PRR. Likewise, as shown in Example 4, such plants also show increased resistance to *Colletotrichum trifolii*, (e.g. reduced severity of Anthracnose, or reduced fungal growth), and to *Phytophthora medicaginis* (e.g. reduced disease severity, such as delayed symptoms). It is further noted that the CCoAOMT-suppressed plants, but not C4H-suppressed plants, produce increased amounts of the flavonoids 7,4-dihydroxyflavone, naringenin and apigenin (FIG. 9). Blocking the lignin biosynthetic pathway at CCoAOMT thus appears to cause increased flux toward flavonoid biosynthesis (FIG. 10).

In one embodiment, a plant provided by the invention is more resistant to a fungal plant pathogen, such as a soil-borne pathogen, a root-infecting pathogen, or a foliar-infecting pathogen, than a corresponding plant, otherwise essentially identical but not comprising the first selected DNA. In certain embodiments, a plant provided by the invention is more resistant to *P. omnivora*, i.e. shows reduced *Phymatotrichopsis* Root Rot disease severity, than the corresponding plant not comprising the first selected DNA. A first plant can be considered to display reduced disease severity than a second plant when the first plant exhibits less disease, or the disease progresses more slowly, than in the second plant. The amount of disease infecting a plant can be measured by any means known in the art. As in Example 1, roots of inoculated rooted cuttings or seedlings can be observed after a particular time interval or intervals, and percentage of roots that are discolored can be estimated. Loss of foliage can also be measured. See Example 1. In other embodiments, a plant provided by the invention exhibits reduced disease severity when infected by another fungal plant pathogen, such as *Colletotrichum* spp. including *C. trifolii*, or *Phytophthora medicaginis*.

Such embodiments are not limited to a particular plant; any dicotyledonous plant could be made more resistant to a plant disease, such as *Phymatotrichopsis* Root Rot, using these methods. Included are plants grown for food, feed, fuel or fiber, ornamental plants, and wild plants. In some embodiments, the plant is cotton, alfalfa, bean, peanut, sweet potato, or a woody plant. In certain embodiments, the plant is a legume. In specific embodiments, the plant is cotton or alfalfa, and the disease is a fungal disease. In some embodiments, the disease is caused by *P. omnivora*, a *Colletotrichum* sp., or a *Phytophthora* sp. In particular embodiments, the disease is caused by *C. trifolii, P. omnivora,* or *Phytophthora medicaginis*.

As discussed above, plants of these embodiments produce increased amounts of the flavonoids 7,4-dihydroxyflavone, naringenin, and apigenin. The metabolite 7,4-dihydroxyflavone is inhibitory to *P. omnivora* (Example 1). Thus, in one aspect of the invention, lignin metabolism may be downregulated to result in increased production of flavonoids, including 7,4-dihydroxyflavone, naringenin and apigenin, which induce plant defense responses to the pathogen. It is further believed that 7,4-dihydroxyflavone can be used as a chemical treatment against fungal infection, such as *P. omnivora* infection. The invention therefore provides a method of treating a plant that is susceptible to a fungal plant pathogen, the method comprising providing 7,4-dihydroxyflavone to the plant. In some embodiments, the fungal plant pathogen is a root-infecting pathogen such as *Phymatotrichopsis omnivora*. In other embodiments, the fungal plant pathogen is a foliar pathogen, such as *C. trifolii.*

I. PLANT TRANSFORMATION CONSTRUCTS

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes.

The invention provides a nucleic acid vector comprising a first selected DNA that down-regulates activity of caffeic acid 3-O-methyltransferase (COMT) or caffeoyl CoA 3-O-methyltransferase (CCoAOMT) in the plant, such that, when the vector is transformed into a dicotyledonous plant, the first selected DNA is expressed (a) primarily in the roots of the resulting transgenic plant or (b) primarily in response to infection of the resulting transgenic plant by a root-infecting fungal plant pathogen.

A. Regulatory Elements

The plants and methods of the present invention can utilize a vector comprising a first selected DNA that, when the vector is transfected into a plant, the first selected DNA is expressed (a) primarily in the roots of the resulting transgenic plant or (b) primarily in response to infection of the resulting transgenic plant by a root-infecting fungal plant pathogen. The site and conditions under which the first selected DNA is expressed can be controlled to a great extent by selecting a promoter element in the vector that causes expression under the desired conditions.

In some embodiments, the first selected DNA is expressed primarily in the roots of the plant. Limiting expression of the first selected DNA primarily to the roots rather than the whole plant would tend to reduce any effect of reduced lignin on fitness, since the reduction in lignin is primarily limited to the roots. As used herein, "expressed primarily in the roots" means the first selected DNA is expressed in a greater quantity in roots than in vegetative tissues of the plant. In one embodiment, the expression in the roots is at least twice as much (i.e., at least twice the amount of transcript present per gm tissue) as in any other individual plant tissue (e.g., stem, leaves, flowers, etc). In further embodiments, the first selected DNA is expressed in the roots at least three, or four, or five times as much as in any other individual tissue. In still further embodiments, the first selected DNA is expressed in the roots at least ten, or fifty, or one hundred times as much as in any other individual tissue. In yet another embodiment, there is no detectable expression of the first selected DNA above baseline in any tissue other than root tissue.

Limiting expression of the first selected DNA primarily to the roots of a plant can be accomplished by operably linking the first selected DNA to a root-preferred promoter. As used herein, a first selected DNA operably linked to a "root-preferred promoter" is expressed in a greater quantity in the roots than in vegetative tissues of the plant. In one embodiment, the expression in the roots of a first selected DNA operably linked to a root-preferred promoter is at least twice as much as in any other individual plant tissue. In further embodiments, the first selected DNA is expressed in the roots at least three, or four, or five times as much as in any other individual tissue. In still further embodiments, the first selected DNA is expressed in the roots at least ten, or fifty, or one hundred times as much as in any other individual tissue where a first selected DNA operably linked to a "root-preferred promoter". In yet another embodiment, there is no detectable expression of the first selected DNA above baseline in any tissue other than root tissue.

Any root-preferred promoter can potentially be utilized to direct expression of the first selected DNA to the roots. Examples include an RB7, RPE15, RPE14, RPE19, RPE29, RPE60, RPE2, RPE39, RPE61, SHR, ELG3, EXP7, EXP18 or Atlg73160 promoter (Vijaybhaskar et al., 2008; Kurata et al., 2005; PCT Publication WO 01/53502; U.S. Pat. No. 5,459,252; Cho and Cosgrove, 2002). The root-preferred promoters disclosed in Examples 2 and 3 and having SEQ ID NO:1-27, i.e., the promoters of Mtr.40382.1.S1_s_at, Mtr.7443.1.S1_at, Mtr.50434.1.S1_at, Mtr.37396.1.S1_at, Mtr.26185.1.S1_at, Mtr.19575.1.S1_at, Mtr.15436.1.S1_at, Mtr.7298.1.S1_at, Mtr.42850.1.S1_at, Mtr.20215.1.S1_at, Mtr.2376.1.S1_at, Mtr.49557.1.S1_at, Mtr.42063.1.S1_at, Mtr.40059.1.S1_at, Mtr.28443.1.S1_s_at, Mtr.51826.1.S1_at, Mtr.43342.1.S1_at, Mtr.15323.1.S1_s_at, Mtr.43627.1.S1_at, Mtr.43627.1.S1_at, Mtr.37966.1.S1_at, Mtr.37966.1.S1_at, Mtr.41871.1.S1_at, Mtr.8517.1.S1_at, Mtr.18796.1.S1_s_at, Mtr.2114.1.S1_at and Mtr.318.1.S1_at, are also envisioned as being useful in the instant methods and compositions. It is noted that promoters were identified that are also strongly induced upon infection with *Phymatotrichopsis omnivora*, (Example 3) and may be used in accordance with the invention.

In other embodiments, the first selected DNA can be expressed primarily in response to infection by a root-infecting fungal plant pathogen. As used herein, "expressed primarily in response to infection by a root-infecting fungal plant pathogen" means the first selected DNA is expressed in a greater quantity in a plant that is infected than in an uninfected plant. In one embodiment, the first selected DNA is expressed at least twice as much (i.e., at least twice the amount of transcript present per gm tissue) in a plant that is infected as from an uninfected plant of the same genotype. In further embodiments, the first selected DNA is expressed in an infected plant at least three, or four, or five times as much as in an uninfected plant. In still further embodiments, the first selected DNA is expressed during infection at least ten, or fifty, or one hundred times as much as in an uninfected plant. In yet another embodiment, there is no detectable expression of the first selected DNA above baseline in an uninfected plant.

Limiting expression of the first selected DNA primarily to response to infection can be accomplished by operably linking the first selected DNA to a fungal pathogen-inducible promoter. As used herein, a first selected DNA operably linked to a "fungal pathogen-inducible promoter" is expressed in a greater quantity in a plant that is infected by a fungal pathogen than in an uninfected plant. In one embodiment, the first selected DNA operably linked to a fungal pathogen-inducible promoter is expressed at least twice as much (i.e., at least twice the amount of transcript present per gm tissue) in a plant that is infected as from an uninfected plant of the same genotype. In further embodiments, the first selected DNA is expressed in an infected plant at least three, or four, or five times as much as in an uninfected plant. In still further embodiments, the first selected DNA is expressed during infection at least ten, or fifty, or one hundred times as much as in an uninfected plant. In yet another embodiment, there is no detectable expression of the first selected DNA above baseline in an uninfected plant when the first selected DNA is operably linked to a fungal pathogen-inducible promoter.

Any pathogen-inducible promoter can potentially be utilized to direct expression of the first selected DNA to be expressed primarily in response to infection by a root-infecting fungal plant pathogen. Examples include an hsr203J, PVS3, NI16, or STS8 stilbene synthase promoter (Keller et al., 1999; Yamamizo et al., 2006; U.S. Pat. No. 7,005,562; U.S. Pat. No. 6,072,103). Other examples include the pathogen-inducible promoters disclosed in Example 3 and provided herein as SEQ ID NO:19-27, i.e., the promoters of Mtr.43627.1.S1_at, Mtr.43627.1.S1_at, Mtr.37966.1.S1_at, Mtr.37966.1.S1_at, Mtr.41871.1.S1_at, Mtr.8517.1.S1_at, Mtr.18796.1.S1_s_at, Mtr.2114.1.S1_at and Mtr.318.1.S1_at.

The DNA sequence between the transcription initiation site and the start of the coding sequence, i.e., the untranslated leader sequence, can also influence gene expression. One may thus wish to employ a particular leader sequence with a transformation construct of the invention. Useful leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure.

It is contemplated that vectors for use in accordance with the present invention may be constructed to include an ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, may act to increase the level of transcription from adjacent promoters when applied in the context of plant transformation.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. In one embodiment of the invention, the native terminator of a lignin biosynthesis coding sequence (e.g., of COMT or CCoAOMT) is used. Alternatively, a heterologous 3' end may enhance the expression of sense or antisense COMT or CCoAOMT coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Many examples of suitable marker proteins are known to the art and can be employed in the practice of the invention. Examples include, but not limited to, neo (Potrykus et al., 1985), bar (Hinchee et al., 1988), bxn (Stalker et al., 1988); a mutant acetolactate synthase (ALS) (European Patent Application 154, 204, 1985) a methotrexate resistant DHFR (Thillet et al., 1988), β-glucuronidase (GUS); R-locus (Dellaporta et al., 1988), β-lactamase (Sutcliffe, 1978), xylE (Zukowsky et al., 1983), α-amylase (Ikuta et al., 1990), tyrosinase (Katz et al., 1983), β-galactosidase, luciferase (lux) (Ow et al., 1986), aequorin (Prasher et al., 1985), and green fluorescent protein (Sheen et al., 1995; Haseloff et al., 1997; Reichel et al., 1996; Tian et al., 1997; WO 97/41228).

Included within the terms "selectable" or "screenable" markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

II. ANTISENSE AND RNAi CONSTRUCTS

In the methods and compositions of the present invention, COMT or CCoAOMT activity can be down-regulated by any means known in the art, including through the use of ribozymes or aptamers. COMT or CCoAOMT activity can also be down-regulated with an antisense or RNAi molecule.

In particular, constructs comprising a COMT or CCoAOMT coding sequence, including fragments thereof, in antisense orientation, or combinations of sense and antisense orientation, may be used to decrease or effectively eliminate the expression of the gene in a plant. Accordingly, this may be used to "knock-out" the function of the coding sequence or homologous sequences thereof.

Techniques for RNAi are well known in the art and are described in, for example, Lehner et al., (2004) and Downward (2004). The technique is based on the ability of double stranded RNA to direct the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense, and in some aspects RNAi, methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation or both within a host cell, either in vitro or in vivo, such as within a host plant cell. In certain embodiments of the invention, such an oligonucleotide may comprise any unique portion of a nucleic acid sequence provided herein. In certain embodiments of the invention, such a sequence comprises at least 18, 30, 50, 75 or 100 or more contiguous nucleic acids of the nucleic acid sequence of a lignin biosynthesis gene, and/or complements thereof, which may be in sense and/or antisense orientation. By including sequences in both sense and antisense orientation, increased suppression of the corresponding coding sequence may be achieved.

Constructs may be designed that are complementary to all or part of the promoter and other control regions, exons, introns or even exon-intron boundaries of a gene. It is contemplated that the most effective constructs may include regions complementary to intron/exon splice junctions. Thus, it is proposed that an embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., as in a ribozyme) could be designed. Methods for selection and design of sequences that generate RNAi are well known in the art (e.g. Reynolds, 2004). These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence. Constructs useful for generating RNAi may also comprise concatemers of sub-sequences that display gene regulating activity.

III. METHODS FOR GENETIC TRANSFORMATION

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384, 253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464, 765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is a preferred method for transformation of dicots, including *Arabidopsis*, tobacco, tomato, alfalfa, potato, cotton, bean, peanut, sweet potato and woody plants.

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force.

IV. PRODUCTION AND CHARACTERIZATION OF STABLY TRANSFORMED PLANTS

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce, into the host cell, a marker gene which confers resistance to some normally inhibitory agent, such as an antibiotic or herbicide. Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

Cells that survive the exposure to the selective agent, or cells that have been scored positive in a screening assay, may be cultured in media that supports regeneration of plants. The transformed cells, identified by selection or screening and cultured in an appropriate medium that supports regeneration, will then be allowed to mature into plants. Developing plantlets are transferred to soiless plant growth mix, and hardened, e.g., in an environmentally controlled chamber, for example, at about 85% relative humidity, 600 ppm $CO_2$, and 25-250 microeinsteins $m^{-2} s^{-1}$ of light. Plants may be matured in a growth chamber or greenhouse. Plants can be regenerated from about 6 wk to 10 months after a transformant is identified, depending on the initial tissue.

To confirm the presence of the exogenous DNA in the regenerating plants, a variety of assays may be performed. Such assays include, for example, "molecular biological" assays, such as Southern and northern blotting and polymerase chain reaction (PCR); "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant. DNA integration into the host genome and the independent identities of transformants may be determined using, e.g., Southern hybridization or PCR. Expression may then be evaluated by specifically identifying the protein products of the introduced genes or evaluating the phenotypic changes brought about by their expression.

V. BREEDING PLANTS OF THE INVENTION

In addition to direct transformation of a particular plant genotype with a construct prepared according to the current invention, transgenic plants may be made by crossing a plant having a selected DNA of the invention to a second plant lacking the construct. For example, a selected lignin biosynthesis coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants.

As used herein the term "progeny" denotes the offspring of any generation of a parent plant prepared in accordance with the instant invention, wherein the progeny comprises a selected DNA construct. "Crossing" a plant to provide a plant line having one or more added transgenes relative to a starting plant line, as disclosed herein, is defined as the techniques that result in a first selected DNA of the invention being introduced into a plant line by crossing a starting line with a donor plant line that comprises a first selected DNA of the invention. To achieve this one could, for example, perform the following steps:

(a) plant seeds of the first (starting line) and second (donor plant line that comprises a first selected DNA of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VI. DEFINITIONS

Expression: The combination of intracellular processes, including transcription and translation undergone by a coding DNA molecule such as a structural gene to produce a polypeptide or functional nucleic acid (e.g., an RNAi, antisense molecule, ribozyme, aptamer, etc.).

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VII. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Down-Regulation of the Lignin Pathway Enzymes Caffeoyl CoA 3-O-Methyl-Transferase and Caffeic Acid 3-O-Methyltransferase Results in Increased Resistance of Alfalfa to *Phymatotrichopsis omnivora*

A. Example Summary

*Phymatotrichopsis omnivora* (Duggar) Hennebert, causes a destructive root rot in cotton, alfalfa (*Medicago sativa*), and many other dicot species. No consistently effective control measures or resistant host germplasm for *Phymatotrichopsis*

Root Rot (PRR) are known. The relative genetic intractability of cotton and alfalfa precludes their use as pathosystem hosts for *P. omnivora* and thus most genomic approaches to study PRR. Therefore, the model legume *M. truncatula* was used, taking advantage of its available genetic and genomic resources to investigate PRR. Expression profiling of PRR-infected *M. truncatula* roots using Affymetrix chips identified several up-regulated genes involved in the phenylpropanoid pathway, cell wall modification and lignin biosynthesis. Cinnamyl alcohol dehydrogenase, hydroxycinnamoyltransferase, caffeic acid 3-O-methyltransferase (COMT) and caffeoyl CoA 3-O-methyl-transferase (CCoAOMT) were all up-regulated in roots during pathogenesis. The role of lignin pathway genes identified in the *M. truncatula-P. omnivora* model pathosystem was analyzed using transgenic alfalfa plants down-regulated in cinnamate 4-hydroxylase (C4H), CCoAOMT and COMT. As expected, C4H-suppressed lines showed slightly increased susceptibility. However, surprisingly, CCoAOMT and COMT suppressed lines showed increased resistance to PRR than the vector-control lines. Metabolic profiling further revealed that CCoAOMT lines, but not susceptible wild-type or C4H lines, accumulate increased amounts of flavonoids (7,4-dihydroxyflavone, naringenin and apigenin) upon pathogen inoculation. Taken together, this study identified an important PRR resistance trait associated with CCoAOMT lines, and a pathogen-induced metabolic flux mechanism in these lines.

B. Introduction

Figure 1:
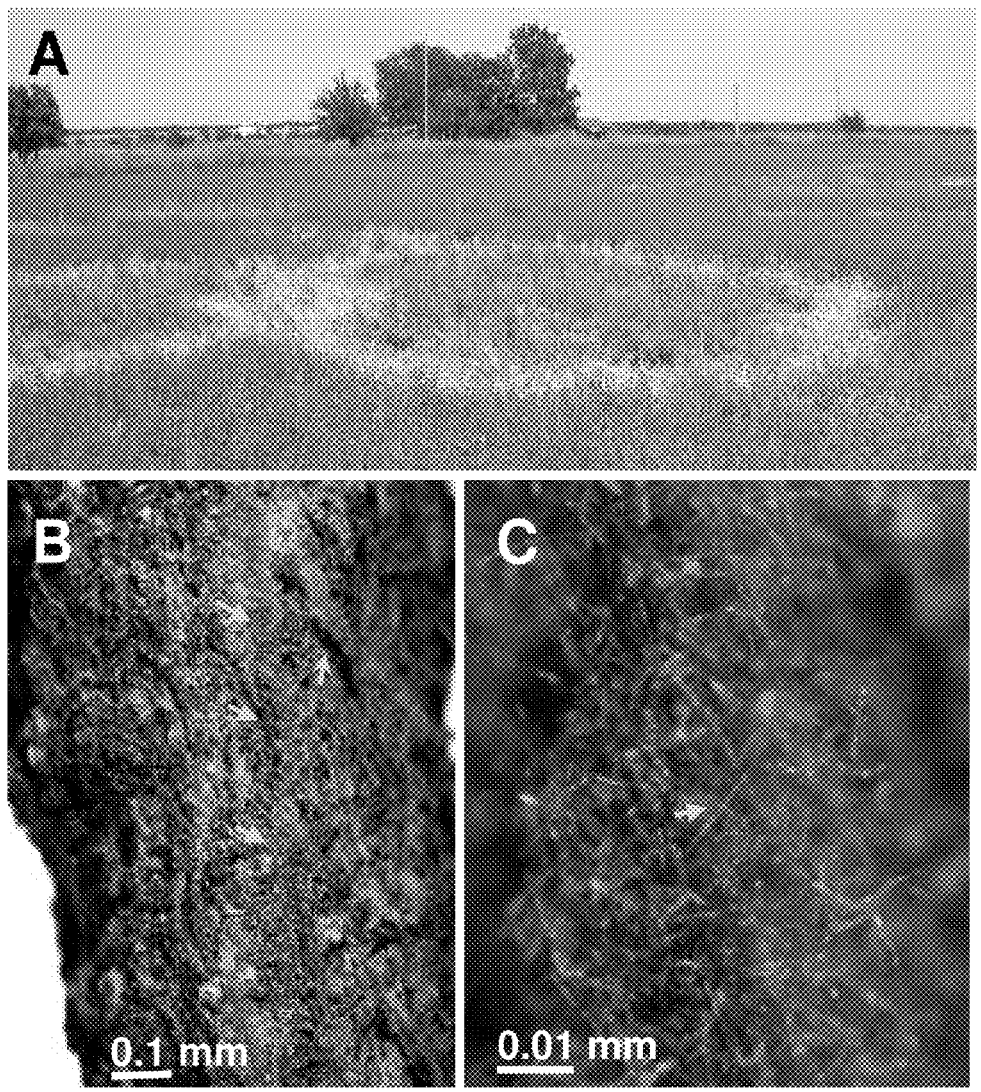
FIG. 1. Circular disease foci in defoliated alfalfa field showing the yield loss (A), mature mycelial strands (arrows) of *P. omnivora* on the root of wilted alfalfa plant (B) and acicular and cruciform hyphae (arrows) on mycelial strand (C).
Figure 2:
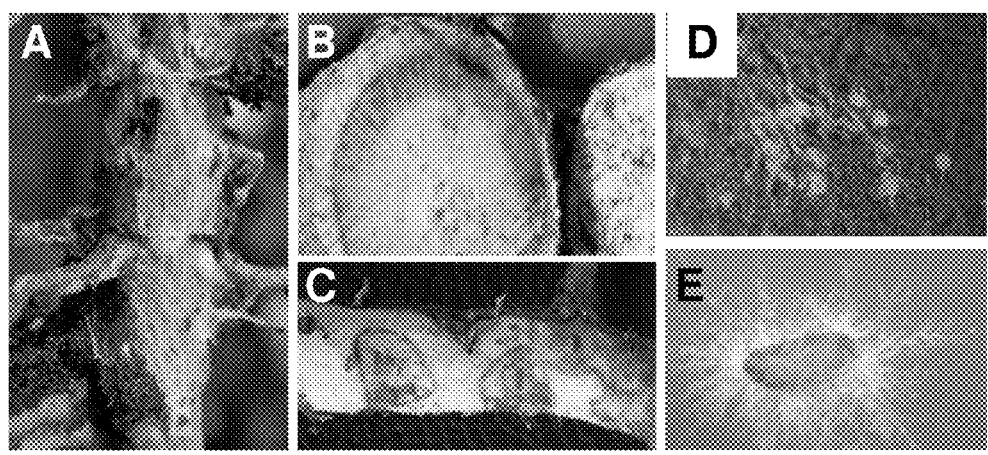
FIG. 2. *Phymatotrichopsis* Root Rot symptoms on cotton roots. (A)-(C) Colonization and symptom development in cotton. (D) Sclerotia formed on the mycelial strands in soil. (E) Germinating sclerotia on water agar.
Figure 3:
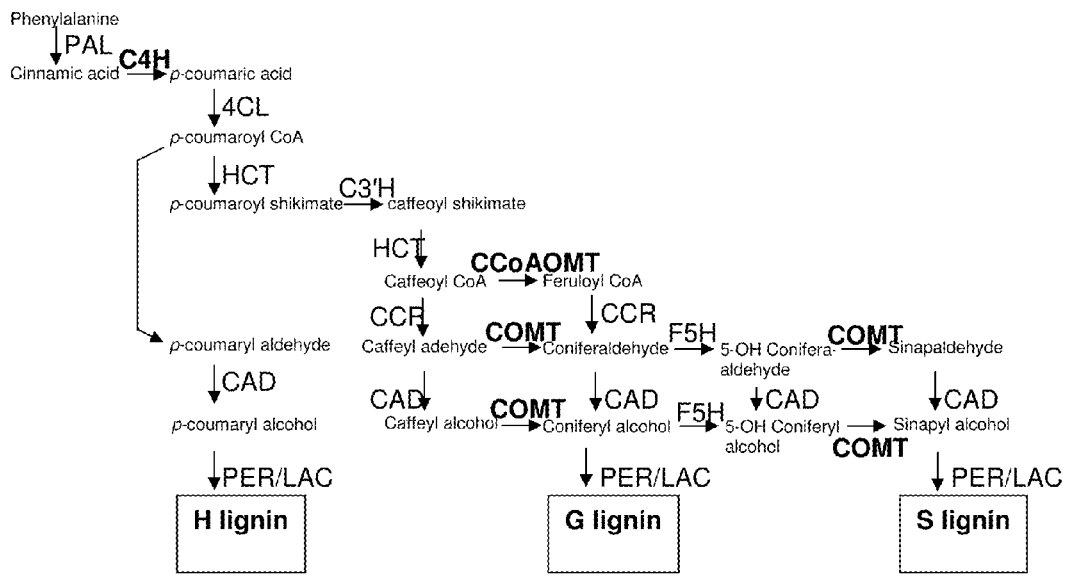
FIG. 3. The lignin biosynthetic pathway and lignin accumulation upon *P. omnivora* inoculation in *Medicago truncatula* roots. (A) Lignin pathway in plants (adapted from Li et al., 2008 and Reddy et al., 2005). Different enzymes abbreviated in the pathway include, L-phenylalanine ammonialyase (PAL); 4-(hydroxy)cinnamate: CoA ligase (4CL); cinnamate 4-hydroxylase (C4H); hydroxycinnamoyl CoA shikimate:quinate hydroxycinnamoyl transferase (HCT); p-coumaroylshikimate 3'-hydroxylase (C3'H); caffeoyl CoA O-methyl transferase (CCoAOMT); (hydroxy)cinnamoyl CoA reductase (CCR); ferulic acid/coniferaldehyde/coniferyl alcohol 5-hydroxylase (F5H); caffeic acid/5-hydroxyferulic acid-methyltransferase (COMT); (hydroxy)cinnamyl alcohol dehydrogenase (CAD); peroxidase (PER); laccase (LAC). (B-C) Mock (B) and *P. omnivora* inoculated (C) *M. truncatula* roots (5 dpi) under UV light. Blue autofluorescence represents lignin deposition.
Figure 3:
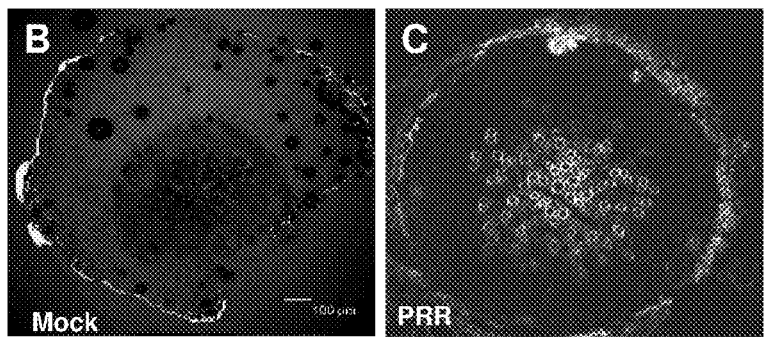

PRR disease symptoms in alfalfa fields are most conspicuous during summer when the infected plants suddenly wilt (FIG. 1). As the diseases progresses, the dead roots are extensively colonized by mycelial strands which is one of the typical characteristic symptoms of PRR (FIG. 1). The roots at later stages of infection showed extensive vascular discoloration in alfalfa and cotton (FIG. 1). The mycelial strands and symptom development in field infected roots are more conspicuous in the natural host cotton (FIG. 2). The strands formed on the root surfaces or in the soil form sclerotia, thus completing the life cycle (FIG. 3 and FIG. 2).

An *M. truncatula-P. omnivora* pathosystem was established to investigate PRR disease development. Expression profiling of PRR-infected *M. truncatula* roots using an Affymetrix chip identified several differentially expressed genes belonging to different metabolic pathways including genes involved in the lignin pathway. Alfalfa transgenic lines down-regulated in C4H showed increased susceptibility to *P. omnivora*. However, surprisingly, CCoAOMT and COMT down-regulated lines showed increased resistance to *P. omnivora*. Furthermore, the resistant CCoAOMT lines but not susceptible wild-type or C4H lines accumulated significantly increased amounts of flavones (7,4-dihydroxyflavone and apigenin) and flavanone (naringenin) upon pathogen inoculation. These results identify a PRR resistance trait associated with COMT and CCoAOMT suppressed lines, and pathogen-induced metabolic spillover as a mechanism of resistance.

C. Results

1. Lignin Accumulation in *P. omnivora* Infected *M. truncatula* Roots

Figure 4:
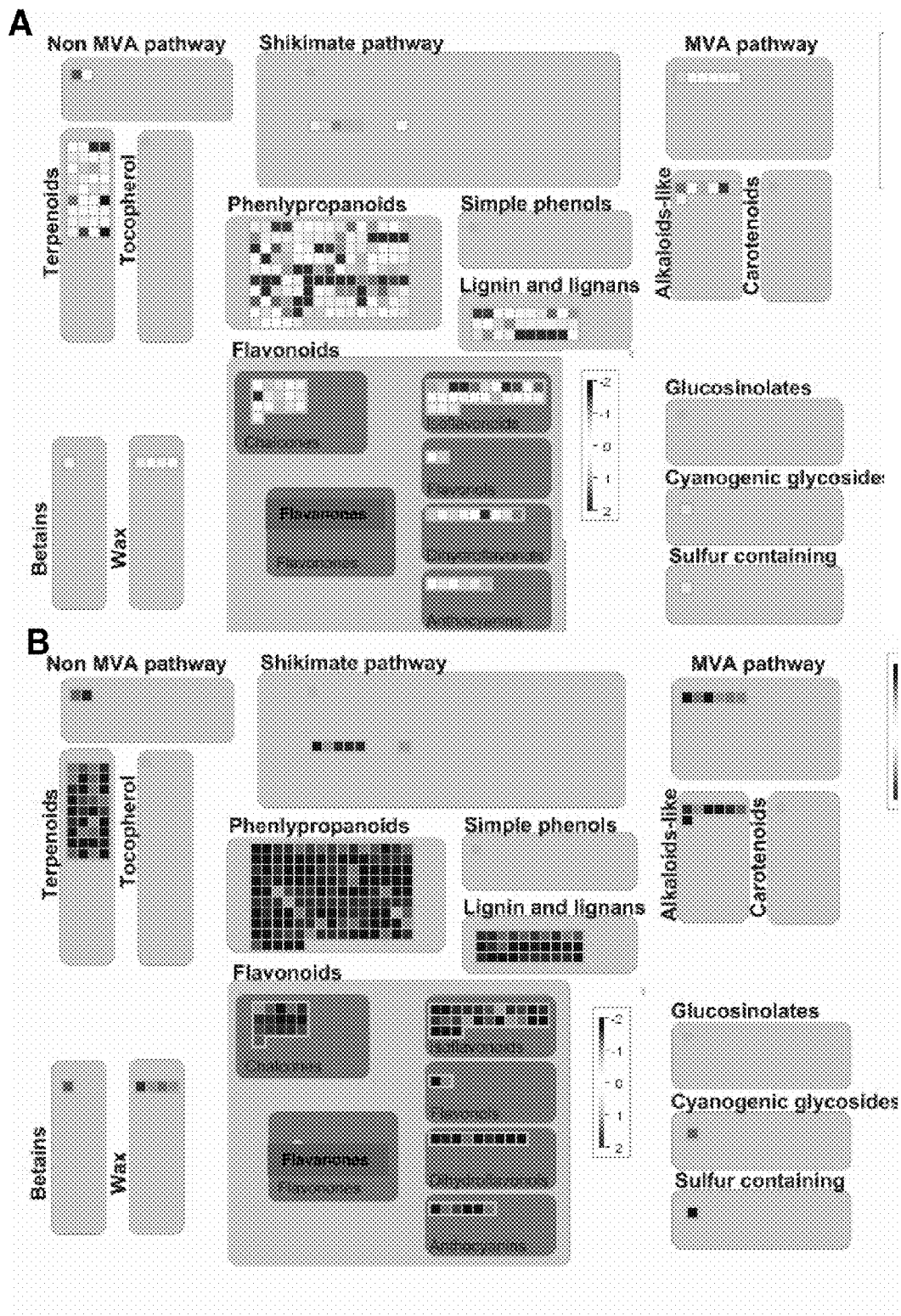
FIG. 4. MAPMAN illustration of *M. truncatula* Affymetrix data showing changes in genes involved in secondary metabolism during *P. omnivora-M. truncatula* interactions at 3 (A) and 5 (B) days post inoculation.

Global expression profiling of *M. truncatula* roots infected with *P. omnivora*, using the Affymetrix GeneChip® *Medicago* Genome Array, showed several genes encoding proteins associated with secondary metabolism and cell-wall modification that were differentially expressed during infection (FIG. 4). Interestingly, genes involved in early steps of phenylpropanoid metabolism were induced both during early and later stages of infection. Furthermore, genes involved in lignin biosynthesis including cinnamyl alcohol dehydrogenase (CAD), hydroxycinnamoyl transferase (HCT), COMT and CCoAMT were up-regulated in roots during pathogenesis (FIG. 4; FIG. 3). Consistent with these results, pathogen inoculated *M. truncatula* roots accumulated increased amounts of (presumably) lignin as visualized by the increased autofluorescence of cell walls (FIG. 3).

Figure 5:
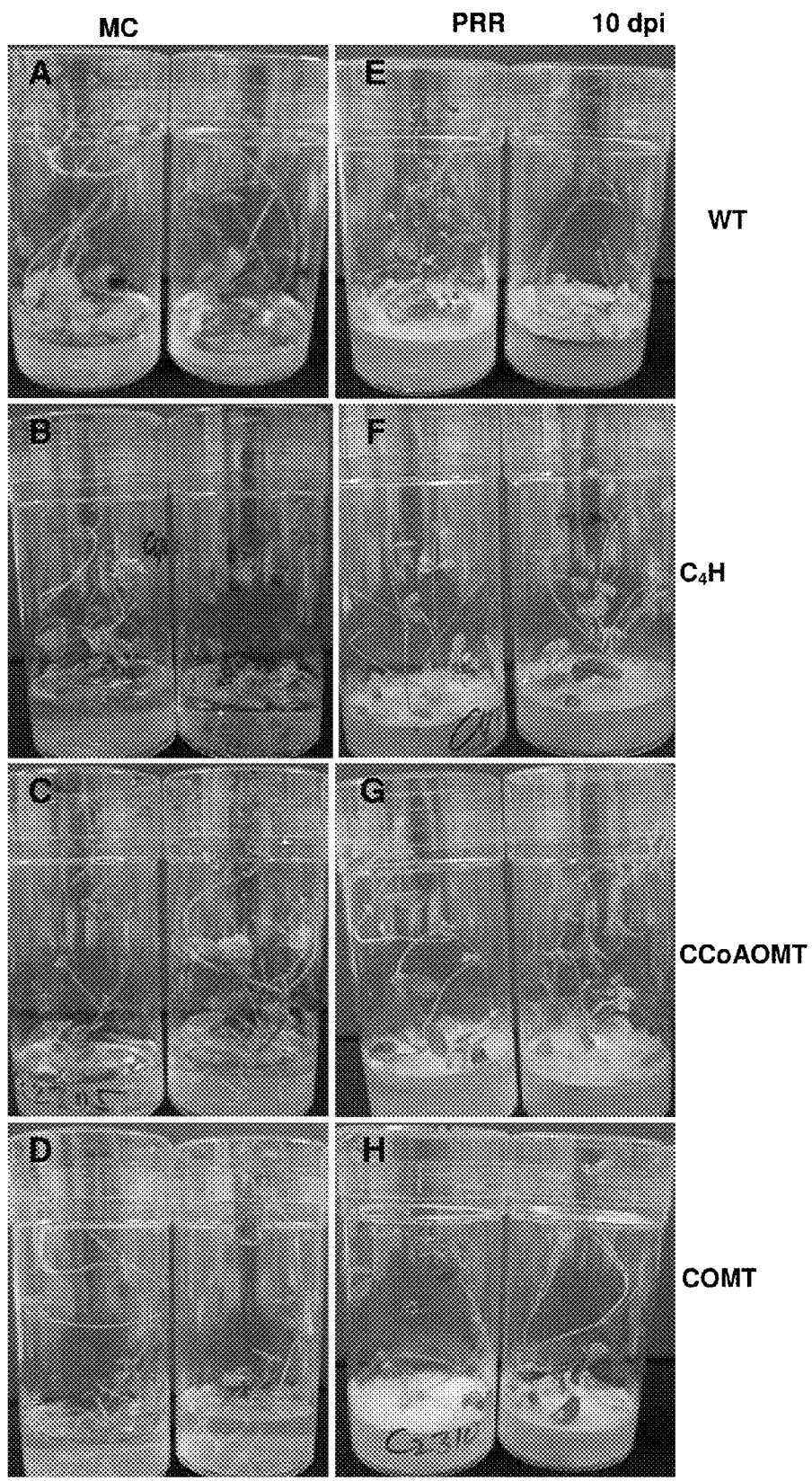
FIG. 5. Disease phenotype of mock (MC) and *P. omnivora* (PR'R) inoculated wild-type and lignin down-regulated alfalfa (*M. sativa*) transgenic lines in agar assays. Pathogen assays were conducted in agar as described in Materials and Methods using four-week old wild-type (WT, cv. RSY4D) and transgenic lines down-regulated in cinnamate 4-hydroxylase (C4H), caffeoyl CoA O-methyl transferase (CCoAOMT), or caffeic acid/5-hydroxyferulic acid O-methyltransferase (COMT). Photos were taken 10 days post inoculation (dpi).
Figure 6:
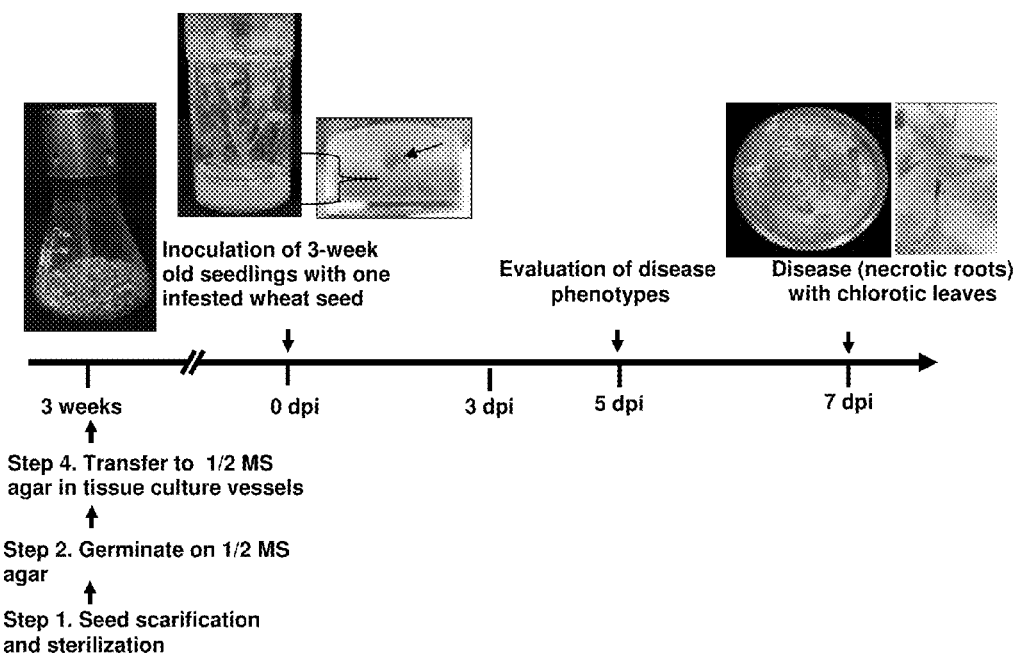
FIG. 6. Schematic showing the sequence of events for conducting the infection assay. *M. truncatula* seeds were surface-sterilized, rinsed in sterile distilled water, and then germinated on MS medium in the dark. Four-weeks after germination, seedlings were inoculated with a wheat seed infested with *P. omnivora*. Disease phenotypes were reproducibly evaluated at 3 and 5 dpi, and roots generally showed symptoms at 7-8 dpi.

2. Effect of Downregulation of C4H, CCoAMT and COMT on Disease Susceptibility in Alfalfa To further investigate the role of lignin up-regulation, alfalfa transgenic lines down-regulated in genes encoding different steps of the monolignol pathway were analyzed. It is important to note that down-regulation of C4H resulted in reduced plant growth when compared to the wild-type; however, CCoAMT and COMT suppressed lines did not show any abnormal growth phenotypes (FIG. 5). Initially, pathogen assays were conducted on axenic seedlings grown in agar to rule out the possibility of any soil-borne microbes influencing the disease phenotype. In agar assays, wild-type plants showed typical PRR symptoms within 10 days post-inoculation (dpi), and, with the progress of the disease, aerial parts including leaves showed characteristic chlorotic streaks and defoliation (FIG. 5). The infected roots showed browning due to necrosis (FIG. 5, FIG. 6).

Consistent with a hypothesis that lignin is a component of plant defense response to pathogens, C4H suppressed lines were highly susceptible to *P. omnivora* (FIG. 5). Disease progress was faster in C4H suppressed lines than in wild-type plants, and the fungus even colonized the dead parts of the shoot (FIG. 5). However, surprisingly, alfalfa transgenic lines down-regulated in COMT and CCoAMT demonstrated resistance to PRR and showed no significant loss of foliage (FIG. 5).

Figure 7:
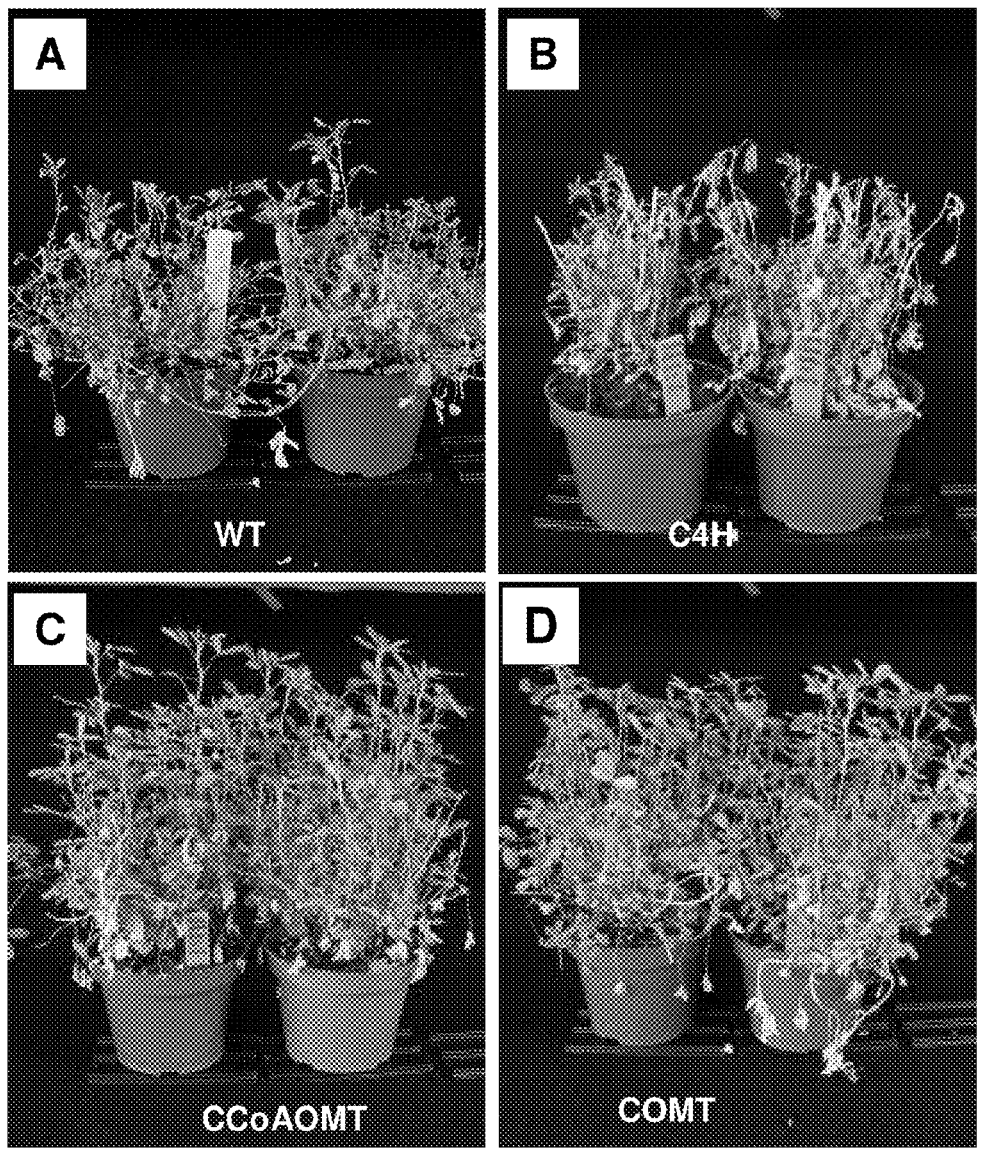
FIG. 7. Disease phenotype of *P. omnivora* inoculated wild-type and lignin down-regulated alfalfa (*M. sativa*) transgenic lines in soil assays. Pathogen assays were conducted in black soil as described in Materials and Methods using six-week old wild-type (WT, cv. RSY4D vector control) and transgenic lines down-regulated in cinnamate 4-hydroxylase (C4H), caffeoyl CoA O-methyl transferase (CCoAOMT), or caffeic acid/5-hydroxyferulic acid O-methyltransferase (COMT) were inoculated with infested wheat seeds and photos taken 15 days post inoculation (dpi).
Figure 8:
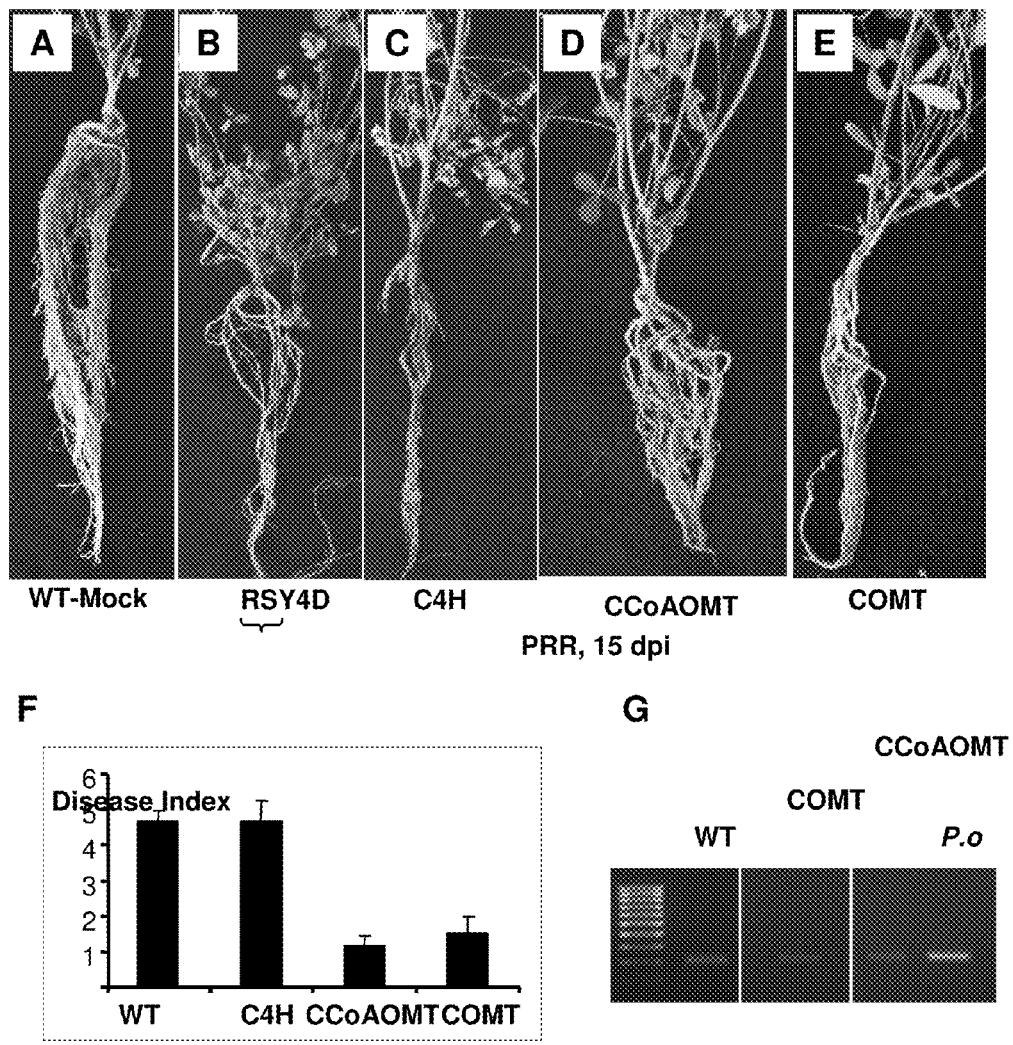
FIG. 8. Disease severity (A-E) and disease index (F) of *P. omnivora* inoculated wild-type and lignin down-regulated alfalfa (*M. sativa*) transgenic lines. Pathogen assays were conducted in black soil as described in Materials and Methods using six-week old wild-type (WT, cv. RSY4D vector control) and transgenic lines down-regulated in cinnamate 4-hydroxylase (C4H), caffeoyl CoA O-methyl transferase (CCoAOMT), or caffeic acid/5-hydroxyferulic acid O-methyltransferase (COMT). Photos were taken 15 days post inoculation (dpi). (G) Colonization of *P. omnivora* in the wild-type, COMT and CCoAOMT lines was confirmed using PCR amplification of a pathogen-specific amplicon (arrow) using ITS primers. DNA isolated from *P. omnivora* (P.o) was used as positive control.

To further confirm these results, disease assays were conducted in black soil (the natural soil type for *P. omnivora*) using transgenic alfalfa seedlings propagated through cuttings. Vegetatively propagated seedlings were used for these experiments to avoid genetic variation and transgene expression reduction through inbreeding depression. Consistent with the agar assays results, wild-type (vector control) and C4H suppressed lines showed typical disease symptoms associated with leaf chlorosis (death) and reduced growth (FIG. 7), whereas CCoAMT and COMT suppressed alfalfa lines showed resistance and higher biomass when compared to the wild-type plants (FIG. 8). The PRR disease and resistance phenotypes were more conspicuous in roots (FIG. 8). Severe root necrosis was visible in C4H suppressed lines when compared to the wild-type plants (FIG. 8). However, the roots of CCoAMT and COMT suppressed lines showed few necrotic lesions at the site of inoculation and remained healthy (FIG. 8). Synchronizing infection in soil assays was found to be less reproducible than in agar assays. Therefore, to rule out the possibility that CCoAMT and COMT lines escaped infection in soil assays, the presence of the pathogen was confirmed using *P. omnivora*-specific ITS sequences. The PCR results from the genomic DNA extracted from roots of *P. omnivora* inoculated wild-type and C4H, CCoAMT, and COMT suppressed lines confirmed the presence of an amplicon specific for *P. omnivora* (FIG. 8). Taken together, the agar and soil assays identified a PRR resistance trait associated with CCoAOMT and COMT lines.

3. Determination of Flavonoid and Isoflavonoid Content

To further investigate the mechanisms of induced resistance in CCoAMT suppressed lines, flavonoid contents were analyzed upon pathogen inoculation. Interestingly, the results clearly showed that upon pathogen colonization, flavonoid biosynthesis and significant accumulation of 7,4-dihydroxyflavone occurred in PRR resistant CCoAMT lines, but not in C4H or wild-type plants (FIG. 9). Furthermore, significant amounts of naringenin, the flavanone intermediate of the flavonoid pathway and apigenin (another flavone) also accumulated in CCoAMT lines, but not in C4H or wild-type plants (FIG. 9). However, resistance was not associated with any significant changes in isoflavonoid (medicarpin) contents (FIG. 9). Interestingly, in in vitro assays, 7,4-dihydroxyflavone inhibited fungal growth at 0.1 mM, suggesting that 7,4-dihydroxyflavone is a novel phytoalexin and plays a significant role in disease resistance to P. omnivora in CCoAMT suppressed alfalfa lines.

D. Discussion and Conclusions

Lignin is an abundant biopolymer and is a major component of plant cell walls. However, from a prospective of forage and biofuel applications of alfalfa, lignin concentrations negatively correlate with digestibility and ethanol conversion from cellulosic biomass (Guo et al., 2001a,b; Reddy et al., 2005; Chen and Dixon, 2007; Li et al., 2008). Lignin precursors and the process of lignification play a role in plant defense responses to pathogens (reviewed by Vance et al., 1980; Bennett and Wallsgrove, 1994; Dixon et al., 1996). Up-regulation of CCoAMT in parsley cell suspensions upon elicitation with fungal elicitors is reported (Pakusch et al., 1989). Furthermore, it was also shown that suppression or down-regulation of cinnamyl alcohol dehydrogenase (CAD; FIG. 3) increases susceptibility of barley to *Erysiphe graminis* (Carver et al., 1994) and flax to *Fusarium oxysporum* (Wrobel-Kwiatkowska et al., 2007). Consistent with these results, down-regulation of C4H, a key enzyme in the phenylpropanoid and lignin pathways (FIG. 3 slightly increased susceptibility of alfalfa to P. omnivora (FIGS. 5,8).

However, down-regulation of CCoAMT and COMT increased resistance to P. omnivora (FIGS. 5,8). COMT was first identified as an enzyme that methylates both the 3-hydroxyl group of caffeic acid and the 5-hydroxyl group of 5-hydroxyferulic acid in the monolignol pathway, and it is specifically required for syringyl lignin (S lignin) biosynthesis (FIG. 3; Dwivedi et al., 1994; Zhong et al., 2000). In alfalfa it was shown that strong downregulation of COMT results in reduction of total lignin and S lignin contents (Guo et al., 2001a). CCoAMT is involved in methylation of caffeoyl CoA to feruloyl CoA in guaiacyl lignin (G lignin) biosynthesis (Meyermans et al., 2000; Zhong et al., 2000; Parvathi et al., 2001; Guo et al., 2001a; Ye et al., 1994, 2001; Do et al., 2007).

Interestingly, the pathogen-inoculated CCoAMT suppressed lines accumulated increased amounts of flavonoids including 7,4-dihydroxyflavone, naringenin and apigenin (FIGS. 9,10). These results suggest a spillover in flux toward the flavonoid pathway in transgenic lines altered in the monlignol pathway, leading to resistance (FIG. 10). Previous studies have shown that downregulation of CCoAMT had no significant effects on accumulation of free and cell wall bound phenolics in the leaves (Guo et al., 2001a). However, recently using a comprehensive molecular phenotyping, Dauwe et al. (2007) have shown that downregulation of other monolignol pathway enzymes, namely CAD and CCR, alters cell-wall and stress metabolism in tobacco. Furthermore, Besseau et al. (2007) demonstrated a strong increase in various flavonoids in hydroxycinnamoyl-CoA shikimate/quinate hydroxycinnamoyl transferase (HCT)-suppressed *Arabidopsis* leaves. In addition, redundant functions of CCoAMT in flavonoid biosynthesis have been suggested (Do et al., 2007). It was thus determined whether the pathogen induced phenylpropanoid pathway is rerouted to the flavonoid pathway in CCoAMT suppressed lines leading to the accumulation of 7,4-dihydroxyflavone and other intermediates in roots (FIG. 10). Flavonoids and isoflavonoids can play a significant role in plant defense responses to fungal and bacterial pathogens (Blount et al. 1992; Dixon and Steele, 1999; Harborne, 1977; Tahara, 2007) and as inhibitors of fungal growth in vitro (Lozovaya et al. 2004; Bhattacharyya and Ward, 1985). Based on metabolomic analysis and in vitro inhibition assays, it appears that the flavonoids accumulated in CCoAOMT lines can play a role in resistance (FIG. 9). Interestingly, 7,4-dihydroxyflavone showed very high inhibitory activity towards P. omnivora in in vitro assays. The integration of recent "omic" approaches with traditional biochemistry should provide new insights into how CCoAOMT downregulation alters the metabolic flux towards the flavonoid pathway leading to the accumulation of dihydroxyflavone but not isoflavonoids in alfalfa roots.

In conclusion, these results indicate that COMT and CCoAMT lines offer great potential to integrate improved digestibility and biofuel production without compromising susceptibility to P. omnivora; rather, these particular lines have enhanced tolerance of the disease. Furthermore, no abnormal growth or biomass production was observed in CCoAMT suppressed alfalfa lines, unlike the C4H suppressed lines (FIG. 5; Guo et al., 2001a; Reddy et al., 2005). Therefore, CCoAMT and COMT lines may offer significant improvement in alfalfa production, considering the fact that PRR disease is a major problem, particularly in the southern United States.

E. Materials and Methods

1. Inoculum Preparation

Strains of P. omnivora isolated from alfalfa (Courtney, Okla.) in 2004 were obtained from Dr. Stephen Marek, Oklahoma State University, Stillwater, Okla. The isolated cultures were incubated at 28° C. One week old freshly grown cultures of P. omnivora on PDA were examined under the light microscope for contamination with other fungi and for observation of the characteristic septal constrictions on single hyphae, hyphal aggregation into strands, and cruciform hyphae and confirmed using PCR with specific ITS primers. Cultures of Oklaf-8 were maintained on modified 1078 medium (Bloss and Wheeler, 1975) at 28° C. in the dark and were periodically sub-cultured to fresh media by mycelial transfer (agar-plugs). Inoculum of P. omnivora Oklaf-8 for agar-based assays was developed in wheat (*Triticum aestivum*). Wheat seeds (Red river grain Co., Kingston, Okla., USA) soaked overnight were autoclaved (30 min at 121° C.) in a cotton-plugged widemouth glass conical flask. The autoclaved seeds were incubated for another 12 h at room temperature (RT), autoclaved for a second cycle (30 min at 121° C.) and allowed to cool at RT. Two agar-plugs (1 cm diameter) from actively growing regions of one week old cultures were used to inoculate 50 g wheat seeds. The flasks were then incubated for 10-12 days at 28° C. in the dark to allow the mycelia to infest the seeds.

2. Plant Material

Seeds of *Medicago truncatula* cv. Jemalong A17, tetraploid M. sativa cv. Regen SY (RSY4D), and transgenic antisense lines down-regulated in C4H (Reddy et al., 2005); CCoAOMT (transgenic lines ACC305 and ACC315; Guo et al., 2001a); COMT (transgenic line AC310; Guo et al., 2001a) were used in assays conducted on agar media. However, clonally propagated vector control and transgenic antisense lines were used for assays conducted in black soil. Seeds of *M. truncatula* cv. Jemalong A17 were scarified for 8 min using concentrated sulfuric acid, washed three times with distilled water, and surface sterilized for 15 min in 20% (v/v) commercial bleach containing 6% sodium hypochlorite (Clorax Co., Okland, Calif.). However, scarification step was omitted for alfalfa seeds. Surface sterilized seeds were washed three times with distilled water and germinated on half-strength Murashige and Skoog (MS) medium (0.2% phytagel; Signia).

3. Pathogen Infection Assays in Agar and Black Soil

Two days after germination in darkness at 24° C., seedlings with 2-3 cm long hypocotyls were transferred to plant tissue culture containers (58 dia×100 height; Greiner Bio-One North America Inc., Monroe, N.C., USA) containing half-strength MS medium (0.2% phytagel) with Gamborg vitamins (PhytoTechnologies Laboratories, Shawnee Mission, Kans., USA), 1% sucrose, pH 5.6-5.8, and were maintained in growth chambers (24° C., 40-70% RH, 12 h photoperiod, photon flux density 150-200 µmol m$^{-2}$ sec$^{-1}$). Inoculation assays were conducted on four-week old plants. A single wheat seed infested with *P. omnivora* (inoculum prepared as described above) was used to inoculate *M. truncatula/M. sativa* seedlings grown in tissue culture tubes. A single wheat seed infested with *P. omnivora* was placed very close to the main root, at the interface of the root and shoot (FIG. 6). The inoculated seedlings were transferred to growth chambers (26° C., 40% RH, 12 h photoperiod, photon flux density 150-200 µmol m$^{-2}$ sec$^{-1}$) and the symptoms were monitored at different time intervals post inoculation. Seedlings mock-inoculated with one autoclaved wheat seed served as mock-controls (MC).

Cuttings from *M. sativa* wild-type, vector control and lignin down-regulated transgenic lines were clonally propagated in 4" pots using autoclaved black soil collected from research fields at Texas Cooperative Extension, Texas A&M University, Dallas, Tex., USA. Wheat seed infested with *P. omnivora* (inoculum prepared as described above) was used to inoculate six-week old *M. sativa* cuttings grown in black soil. Prior to inoculation, soil (3 cm deep) was removed and 5 g of wheat inoculum was evenly spread around the root and the inoculum was covered with 2-3 cm of autoclaved black soil. Autoclaved wheat seeds were used as mock inoculation controls. Inoculated plants were incubated in growth chambers (26° C./22° C., 30-50% RH, 16-h photoperiod, photon flux density 150-200 µmol m$^{-1}$ sec$^{-1}$). Fifteen days after inoculation, plants were rated for PRR and the experiments were repeated on four separate dates. Disease rating was based on a 1-5 scale: 1-2 light disease (10-15% of root affected), 3 moderate disease (20-30% of root affected), 4-5-full disease (more than 60% of root affected).

4. UV Fluorescence Microscopy

For microscopic observations of lignin deposition in root cortical or vascular tissues, 4-5 mm sections of infected roots were flash frozen in liquid nitrogen and 20 µm transverse sections were cut using a Leica CM 1850 cryomicrotome (Leica Microsystems Nussloch GmbH, Nussloch, Germany). Root sections were transferred onto a slide glass and were mounted using a cover glass with Dow Corning® high vacuum grease for microscopy. Fluorescence microscopy to document blue autofluorescence was done using a Leica TCS SP2 AOBS Confocal Laser Scanning Microscope (Leica Microsystems Heidelberg GmbH, Mannheim, Germany) equipped with 20× (numerical aperture, 0.70) and 63× (numerical aperture, 1.2) objectives using appropriate laser settings (UV, blue diode laser).

5. Extraction and Quantification of Flavonoid Compounds Using Liquid Chromatography-Mass Spectroscopy Root samples from mock and pathogen inoculated alfalfa plants were quickly rinsed with water to remove black soil and were flash frozen in liquid nitrogen. The frozen samples were ground using a Waring™ two-speed blender and were lyophilized for 48 h. The dried samples (10±0.05 mg) were then extracted with 0.5 mL 80% v/v $CH_3OH$ in water at room temperature for 2 h. After centrifugation to remove the tissue residues, the extract was loaded on a UPLC/MS for analyzing secondary metabolites.

Example 2

Exploiting the *Medicago truncatula* Genome for Root-Specific Genes

This Example provides expression data containing three independent root samples (without nodules). Each root sample was tested with three biological replicates. Among the 50,900 *M. truncatula* probesets on the Affymetrix Gene-Chip® *Medicago* Genome Array:

23,224 probesets were found expressed in roots (P=3 for all three root samples)
   619 probesets were expressed only in roots within the organ series
   639 were expressed (P=3) in all three root samples
      400 were expressed in all root samples and were specific to roots
      273 were root-specific with expression≧100 (mean of the three root samples)
         189 showed minimal expression=100 in all three root samples
         21 showed minimal expression=1000 in all three root samples Table 1 lists 18 DNA sequences that comprise root-specific promoters (−2 kb, for the purpose of this study) corresponding to probesets mapped on the *Medicago* genome sequence. The promoters are provided as SEQ ID NO:1-18, as indicated in Table 1. In those sequences, the last three nucleotides correspond to the predicted start codon of the coded protein. Expression details for each probeset can be visualized/extract through the *Medicago* Gene Atlas (Benedito et al., 2008).

Promoters are ordered according to minimal values and include from strong to moderate expression. Expression in nodules was not considered in this study.

TABLE 1

Transcription of root-specific genes in *Medicago truncatula*.

| SEQ ID NO:[1] | Affymetrix probeset | IMGAG locus | MTGI 8.0 chrom | proposed transcript | function | expression in roots | | |
|---|---|---|---|---|---|---|---|---|
| | | | | | | mean | max | min |
| 1 | Mtr.40382.1.S1_s_at | CU024875_36.4 | MtChr3 | TC107169 | SAM-dep carboxyl methyltransferase | 4891.7 | 7111.8 | 3726.6 |
| 2 | Mtr.7443.1.S1_at | CT971488_5.4 | MtChr3 | TC112185 | unknown function | 4887.9 | 6901.2 | 2860.5 |
| 3 | Mtr.50434.1.S1_at | AC140030_24.5 | MtChr4 | | Integral membrane protein of unknown function DUF588 | 2669.9 | 3237.5 | 2368.4 |

TABLE 1-continued

Transcription of root-specific genes in *Medicago truncatula*.

| SEQ ID NO:[1] | Affymetrix probeset | IMGAG locus | chrom | MTGI 8.0 transcript | proposed function | expression in roots mean | max | min |
|---|---|---|---|---|---|---|---|---|
| 4 | Mtr.37396.1.S1_at | AC161864_16.5 | MtChr1 | TC100572 | GST; Intracellular chloride channel; | 2480.3 | 2704.2 | 2206.5 |
| 5 | Mtr.26185.1.S1_at | AC151709_33.5 | MtChr1 | | lipoxygenase endonuclease/ exonuclease/ phosphatase family similar to inositol | 2206.4 | 2603.1 | 1839.8 |
| 6 | Mtr.19575.1.S1_at | AC145767_51.4 | MtChr1 | | Glutelin | 4899.0 | 10289.5 | 1826.5 |
| 7 | Mtr.15436.1.S1_at | AC125478_19.4 | MtChr7 | | 2OG-Fe(II) oxygenase; Immunoglobulin/ major histocompatibility complex | 2889.8 | 4507.9 | 1750.6 |
| 8 | Mtr.7298.1.S1_at | CT009540_27.5 | MtChr3 | TC105991 | Glycine-rich protein | 3312.6 | 5530.2 | 1689.0 |
| 9 | Mtr.42850.1.S1_at | AC162161_3.5 | MtChr8 | TC93947 | Acid phosphatase | 2725.4 | 4824.5 | 1476.3 |
| 10 | Mtr.20215.1.S1_s_at | AC148348_5.4 | MtChr4 | | Uncharacterized Cys-rich domain | 3018.9 | 4363.5 | 1407.4 |
| 11 | Mtr.2376.1.S1_at | AC169174_8.4 | MtChr2 | BG588282 | uclacyanin-like protein OR Blue (type 1) copper domain | 1897.8 | 2522.4 | 1394.2 |
| 12 | Mtr.49557.1.S1_at | AC148348_5.4 | MtChr4 | | Uncharacterized Cys-rich domain | 1926.8 | 2940.9 | 1005.9 |
| 13 | Mtr.42063.1.S1_at | CT573051_35.4 | MtChr5 | TC110672 | Haem peroxidase | 1109.7 | 1260.8 | 815.2 |
| 14 | Mtr.40059.1.S1_at | CU062421_13.3 | MtChr3 | TC106417 | hypothetical protein; DNA Polymerase | 1196.3 | 1661.0 | 807.9 |
| 15 | Mtr.28443.1.S1_s_at | AC135102_10.4 | MtChr2 | BG645819, TC96786 | similar to At5g49760; kinase | 819.7 | 967.3 | 745.7 |
| 16 | Mtr.51826.1.S1_at | AC136839_11.4 | MtChr8 | TC102531 | hypothetical protein, UVI1 | 1757.7 | 3682.1 | 720.3 |
| 17 | Mtr.43342.1.S1_at | AC146862_10.4 | MtChr8 | TC95110 | MDR, cyclic peptide transporter | 862.6 | 966.1 | 658.7 |
| 18 | Mtr.15323.1.S1_s_at | AC122161 | MtChr1 | TC94963, TC95097 | phosphate permease (MFS) | 1819.4 | 3668.4 | 647.2 |

[1]SEQ ID NO: of promoter sequence

Example 3

Exploiting the *Medicago truncatula* Genome for Genes Induced Upon Root Infection with Fungi The Affymetrix GeneChip® *Medicago* Genome Array was used to identify *Medicago truncatula* genes that are strongly induced by *P. omnivora* during infection (3 and 5 days post inoculation [dpi]). Table 2 provides a summary of the genes identified in that assay.

TABLE 2

A list of *Medicago truncatula* genes strongly induced by *P. omnivora* during infection (3 and 5 days post inoculation [dpi]).

| Affy ID | Description | Target Description | Ratio (3 dpi/ MC) | Ratio (5 dpi/ MC) |
|---|---|---|---|---|
| Mtr.43627.1.S1_at | Wound-inducible genes | TC95736/FEA = mRNA/DEF = similar to GB\|AAM64873.1\|21592923\|AY087323 induced upon wounding stress {*Arabidopsis thaliana*;}, partial (83%) | 264.87 | 563.48 |
| Mtr.2534.1.S1_at | Mannitol dehydrogenase | BG648660/FEA = mRNA/DEF = similar to UP\|MTD_FRAAN (Q9ZRF1) Probable mannitol dehydrogenase (NAD-dependent mannitol dehydrogenase), partial (64%) | 126.17 | 67.14 |
| Mtr.5750.1.S1_at | EREBP-3-like protein (Ethylene-response gene) | BF647376/FEA = mRNA/DEF = similar to GB\|BAA95736.1\|7939533\|AB025608 *Nicotiana* EREBP-3-like protein {*Arabidopsis thaliana*;}, partial (53%) | 112.18 | 233.62 |
| Mtr.8884.1.S1_at | Pathogenesis-related protein 4A | TC101688/FEA = mRNA/DEF = homologue to UP\|Q9M7D9 (Q9M7D9) Pathogenesis-related protein 4A, partial (94%) | 99.82 | 278.57 |

TABLE 2-continued

A list of *Medicago truncatula* genes strongly induced by *P. omnivora* during infection (3 and 5 days post inoculation [dpi]).

| Affy ID | Description | Target Description | Ratio (3 dpi/ MC) | Ratio (5 dpi/ MC) |
|---|---|---|---|---|
| Mtr.318.1.S1_at | 12-oxophytodienoic acid 10,11-reductase | 1808.m00058/FEA = mRNA/DEF = CR933104.1 78065 76373 mth2-25b3 similar to UP\|Q76FS0 (Q76FS0) Hypothetical protein PsOPR3 (12-oxophytodienoic acid 10,11-reductase) | 88.26 | 134.93 |
| Mtr.9478.1.S1_at | Laccase-like protein | TC103474/FEA = mRNA/DEF = weakly similar to UP\|Q9LFD2 (Q9LFD2) Laccase-like protein, partial (49%) | 52.40 | 406.36 |
| Mtr.46031.1.S1_s_at | Zn-finger, CCHC type | IMGAG\|924.m00003/FEA = mRNA/DEF = Zn-finger, CCHC type AC137837.3.31 8610 10070 mth2-30e7 Jan. 13, 2005 | 50.35 | 104.57 |
| Mtr.8572.1.S1_at | Thaumatin-like protein precursor | TC100682/FEA = mRNA/DEF = similar to GB\|AAC36740.1\|3643249\|AF090143 thaumatin-like protein precursor MdtH {*Malus x domestica*;}, partial (89%) | 40.82 | 169.18 |
| Mtr.37966.1.S1_at | Sarcoplasmic calcium-binding protein (SCP) | TC101804/FEA = mRNA/DEF = homologue to UP\|SCP_NERDI (P04571) Sarcoplasmic calcium-binding protein (SCP), partial (7%) | 39.74 | 387.39 |
| Mtr.2284.1.S1_at | Regulator of gene silencing, partial (34%) | BG584659/FEA = mRNA/DEF = weakly similar to UP\|Q9AXG2 (Q9AXG2) Regulator of gene silencing, partial (34%) | 30.79 | 328.36 |
| Mtr.28811.1.S1_at | Disease resistance response protein | BM815583/FEA = mRNA/DEF = weakly similar to UP\|Q9FIG6 (Q9FIG6) Similarity to disease resistance response protein, partial (55%) | 22.07 | 238.25 |
| Mtr.42129.1.S1_at | AP2 domain transcription factor | TC110815/FEA = mRNA/DEF = similar to UP\|Q9FGA3 (Q9FGA3) Similarity to AP2 domain transcription factor, partial (20%) | 21.64 | 300.92 |
| Mtr.41777.1.S1_at | Expansin-related protein 1 precursor (AtEXPR1) | TC110080/FEA = mRNA/DEF = weakly similar to UP\|EXR1_ARATH (O23547) Expansin-related protein 1 precursor (AtEXPR1) (At-EXPR1) (Ath-ExpBeta-3.1), partial (35%) | 13.24 | 506.00 |
| Mtr.18805.1.S1_at | Proteinase inhibitor I3, Calcium-binding EF-hand | IMGAG\|964.m00017/FEA = mRNA/DEF = Proteinase inhibitor I3, Kunitz legume; Calcium-binding EF-hand; Kunitz inhibitor ST1-like AC140022.11.161 70058 70672 mth2-11g20 Jan. 13, 2005 | 11.49 | 966.98 |
| Mtr.34114.1.S1_s_at | Pathogenesis related protein, complete | BQ138448/FEA = mRNA/DEF = similar to UP\|Q39450 (Q39450) Pathogenesis related protein, complete | 11.41 | 272.48 |
| Mtr.14147.1.S1_s_at | Disease resistance protein; Leucine-rich repeat | IMGAG\|858.m00001/FEA = mRNA/DEF = Disease resistance protein; NB-ARC; Leucine-rich repeat; AAA ATPase AC135229.30.1 3856 462 mth2-7m14 Jan. 13, 2005 | 10.32 | 95.75 |
| Mtr.20185.1.S1_at | Naringenin-chalcone synthase | IMGAG\|1104.m00013/FEA = mRNA/DEF = Naringenin-chalcone synthase; Type III polyketide synthase AC146575.3.131 82667 81204 mth2-145m4 Jan. 13, 2005 | 9.14 | 83.08 |
| Mtr.45519.1.S1_at | Polygalacturonase inhibiting protein precursor | TC99831/FEA = mRNA/DEF = similar to UP\|Q6A170 (Q6A170) Polygalacturonase inhibiting protein precursor, partial (26%) | 9.00 | 819.21 |
| Mtr.29494.1.S1_at | Pectin methylesterase 9 [*Medicago truncatula*] | NP1130399/FEA = mRNA/DEF = GB\|AY587276.1\|AAT02350.1 pectin methylesterase 9 [*Medicago truncatula*] | 3.19 | 143.26 |
| Mtr.27695.1.S1_at | Auxin response factor 30 | BE942407/FEA = mRNA/DEF = weakly similar to GB\|CAD29618.1\|20145855\|ATH441119 auxin response factor 30 | 2.71 | 173.94 |
| Mtr.6341.1.S1_at | Beta-1,3-glucanase-like protein | BQ139930/FEA = mRNA/DEF = similar to UP\|O49737 (O49737) Beta-1, 3-glucanase-like protein, partial (15%) | 1.27 | 68.05 |
| Mtr.23266.1.S1_at | Protease inhibitor | 1663.m00030/FEA = mRNA/DEF = AC145202.17 44559 44888 mth2-15e9 weakly similar to UP\|Q6YEY6 (Q6YEY6) Protease inhibitor | 108.77 | 25.05 |
| Mtr.23272.1.S1_at | Protease inhibitor 2 | 1663.m00036/FEA = mRNA/DEF = AC145202.17 61879 62690 mth2-15e9 weakly similar to UP\|Q8LNY0 (Q8LNY0) Protease inhibitor 2 (Fragment) | 180.88 | 44.61 |
| Mtr.51826.1.S1_at | Conserved hypothetical protein | IMGAG\|895.m00011/FEA = mRNA/DEF = conserved hypothetical protein AC136839.18.111 51954 51706 mth2-13n2 Jan. 13, 2005 | 206.31 | 133.67 |
| Mtr.12511.1.S1_at | Heat shock factor RHSF2 | TC95045/FEA = mRNA/DEF = similar to UP\|Q6VBB5 (Q6VBB5) Heat shock factor RHSF2, partial (15%) | 58.29 | 46.84 |
| Mtr.37253.1.S1_at | Amino acid transporter-like protein 1 | TC100219/FEA = mRNA/DEF = similar to UP\|Q9SXF7 (Q9SXF7) Amino acid transporter-like protein 1, partial (15%) | 42.32 | 27.42 |
| Mtr.27728.1.S1_s_at | BE997593/FEA = mRNA/DEF= | BE997593/FEA = mRNA/DEF= | 106.01 | 5.36 |
| Mtr.22592.1.S1_at | Cytosolic fructose-1,6-bisphosphatase | 1616.m00031/FEA = mRNA/DEF = AC136472.27 56875 53420 mth2-24f21 similar to UP\|Q9FUA5 (Q9FUA5) Cytosolic fructose-1,6-bisphosphatase (EC 3.1.3.11) | 133.87 | 20.74 |
| Mtr.48955.1.S1_at | Nodulin-like; Major facilitator superfamily | IMGAG\|928.m00008/FEA = mRNA/DEF = Nodulin-like; Major facilitator superfamily MFS_1 AC138010.12.71 35426 38174 mth2-21i21 Jan. 13, 2005 | 141.83 | 25.23 |

Root specific probesets are highlighted in yellow.
MC = mock inoculated control

Table 3 provides data on *Medicago* root expression upon fungal infection (root rot) used together with the Gene Atlas data to select genes strongly induced by fungal infection in roots, but otherwise latent genes.

Among the 50,900 *M. truncatula* probesets on the Affymetrix GeneChip®, selection was made considering:

≧20 fold-change (FC) at 3 dpi and ≧50 FC expression at 5 dpi when compared to control (uninfected) roots;

control roots showed expression call≦100 (meaning basal to no expression);

at 3 dpi and at 5 dpi, expression call>500 (at least moderate expression);

maximum value elsewhere (Gene Atlas, not considering nodules, though)<200.

These thresholds were satisfied by 20 probesets, and sequenced genes were retrieved for further studies (note that some probesets were mapped onto two loci, so the promoter resulting in the induced transcript may be either one—both are provided here).

Table 3 lists 9 root-specific promoters strongly induced upon fungal infection (-2 kb) corresponding to probesets mapped onto the *Medicago* genome sequence. The sequences are provided herein as SEQ ID NO:19-27. In those sequences, the last three nucleotides correspond to the predicted start codon of the encoded protein. Expression details for each probeset can be visualized through the *Medicago* Gene Atlas (Benedito et al., 2008).

1=no symptom; 2=mild symptoms with very low fungal growth (<25%); 3=visible necrosis and moderate fungal growth (25 to 50%); 4=necrosis and fungal growth with conidial formation (50 to 70%); 5=Severe necrosis with leaf discoloration. The screening test was repeated twice. Three independent trifoliate leaves were used in each experiment.

2. Infection assays with *Sclerotinia sclerotiorum*

Agar plugs (5 mm, dia.) from growing regions of *Sclerotinia sclerotiorum* cultures grown on PDA media were used as inoculum. Trifoliate leaves from six week-old clonally propagated wild-type and transgenic antisense alfalfa lines were inoculated with one agar plug per leaf and fungal inoculated leaves were placed on moist filter papers, sealed and incubated at 22° C./19° C., 16-h photoperiod, photon flux density 150-200 μmol m$^{-2}$ sec$^{-1}$). The disease assays and disease scoring were conducted as described above for *Phoma medicaginis*. Disease assays and scoring on detached leaves of five week old wild-type and COMT down-regulated *N. tabacum* RNAi lines using the methods described for *M. sativa*. However, 1 cm PDA agar plug of *S. sclerotiorum* was used for inoculation assay on *N. tabacum*. Two days after inoculation with *S. sclerotiorum*, the size of the observed necrotic region was assessed based on a 0 to 5 scale; 0=no symptom, 1=small necrotic symptom (less than 5 mm, dia), 2=small necrotic symptom (around 1 cm, dia), 3=large necrotic symptom (2-3 cm, dia), 4=very large necrotic symptom (more than 3 cm, dia). The inoculation assay with *S. sclerotiorum* was repeated 6 times and (n=95).

TABLE 3

Root-specific promoters strongly induced upon fungal infection.

| SEQ ID NO:[1] | Probesets | imgag_gene | chrom | uni_gene | root | 3dpi | 5dpi | Ratio 3dpi/R | Ratio 5dpi/R | max elsewhere |
|---|---|---|---|---|---|---|---|---|---|---|
| 19 | Mtr.43627.1.S1_at | AC158501_37.4 | MtChr2 | TC95736 | 11.4 | 3018.5 | 6421.5 | 264.9 | 563.5 | 142.3 |
| 20 | Mtr.43627.1.S1_at | AC158501_34.4 | MtChr2 | | | | | | | |
| 21 | Mtr.37966.1.S1_at | AC198005_15.4 | MtChr7 | TC101804 | 23.4 | 929.5 | 9060.1 | 39.7 | 387.4 | 36.9 |
| 22 | Mtr.37966.1.S1_at | AC198005_14.4 | MtChr7 | | | | | | | |
| 23 | Mtr.41871.1.S1_at | AC139852_16.4 | MtChr7 | TC110284 | 6.1 | 1705.9 | 2082.6 | 279.9 | 341.7 | 177.3 |
| 24 | Mtr.8517.1.S1_at | CR931741_20.4 | MtChr5 | TC100462 | 15.4 | 4145.4 | 4210.0 | 269.6 | 273.8 | 64.4 |
| 25 | Mtr.18796.1.S1_s_at | AC148918_31.4 | MtChr2 | | 8.0 | 548.8 | 2069.8 | 68.7 | 259.1 | 88.8 |
| 26 | Mtr.2114.1.S1_at | AC149268_46.5 | MtChr4 | BF632370 | 11.1 | 664.3 | 1566.8 | 59.6 | 140.6 | 50.0 |
| 27 | Mtr.318.1.S1_at | CR933104_1.5 | MtChr5 | | 14.9 | 1311.6 | 2005.1 | 88.3 | 134.9 | 29.0 |

[1]SEQ ID NO: of promoter sequence

Example 4

Infection Assays and Responses of Lignin Down-Regulated Alfalfa to Fungal Pathogens Other than *P. omnivora*

1. Infection Assays with *Phoma medicaginis*

*Phoma medicaginis*_P3 inoculum was maintained on potato-dextrose agar (PDA; Becton, Dickinson & Co., Sparks, Md.). To promote conidial formation the cultures were grown on YPS agar (0.1% each, yeast extract, peptone, glucose and 1.5% agar) for 2 weeks and conidia were harvested with water. Trifoliate leaves from six week-old clonally propagated wild-type and transgenic antisense alfalfa lines were harvested and spot inoculated with 5 μl of suspension containing 1×10$^6$ spores/ml in 0.05% Tween 20. The mock (distilled water, 0.05% Tween 20) and fungal inoculated leaves were placed on moist filter papers, sealed and incubated at 22° C./19° C., 16-h photoperiod, photon flux density 150-200 μmol m$^{-2}$ sec$^{-1}$). Disease development was monitored every day until 10 days post inoculation. Leaves were assessed for disease severity based on a 0 to 5 scale:

3. Infection Assays with *Colletotrichum trifolii*.

*Colletotrichum trifolii* race 1 (ATCC66954) transformed with a GFP expression vector (pCT74 with constitutive ToxA promoter; Lorang et al., 2001) was maintained on PDA media supplemented with hygromycin (100 μg/ml). Conidia from 10-14 days old cultures were harvested in water washed and resuspended in sterile distilled water. Trifoliate leaves from six week-old clonally propagated wild-type and transgenic antisense alfalfa lines were harvested and spot inoculated with 5 μl of suspension or spray inoculated with a suspension containing 1×10$^6$ spores/ml in 0.05% Tween® 20. Disease assays were conducted as described above for *Phoma medicaginis*. GFP-tagged fungus and auto fluorescence of the chloroplast was visualized using a stereomicroscope (Olympus, SZX16) equipped with epifluorescence. The spot inoculation test was repeated three times and spray inoculation was done once.

4. Disease Assays with *Phytophthora medicaginis*.

*Phytophthora medicaginis* M2019 kindly provided by Deborah A Samac, USDA-ARS-Plant Science Research, St. Paul, Minn., was maintained on V8 agar (100 ml V8 juice, 2 g CaCO$_3$, 15 g agar per liter). For preparation of inoculum, the pathogen was sub-cultured by placing 1 cm² agar blocks on V8 medium, and grown at room temperature in the dark for 7-10 days. The cultures were then homogenized in sterile distilled water (10 ml/g) for 30 sec using a Waring™ two-speed blender. Six week-old clonally propagated wild-type and transgenic antisense alfalfa plants were inoculated with the homogenized mycelia (5 ml/pot) using a pipette. The pots were flooded to keep the soil completely saturated until 3 dpi. Typical symptoms on older plants consisting of wilting of the lower leaves were recorded 10 dpi. Severe disease was associated with blackening of the tap roots, and severe wilting and discoloration of the leaves. The photos shown in FIG. 13 were taken at 10 dpi, where 50% of the CCoAOMT plants still showed healthy leaves, whereas the C4H lines displayed severe necrosis with leaf discoloration (yellowing).

5. Disease Responses

Figure 11:
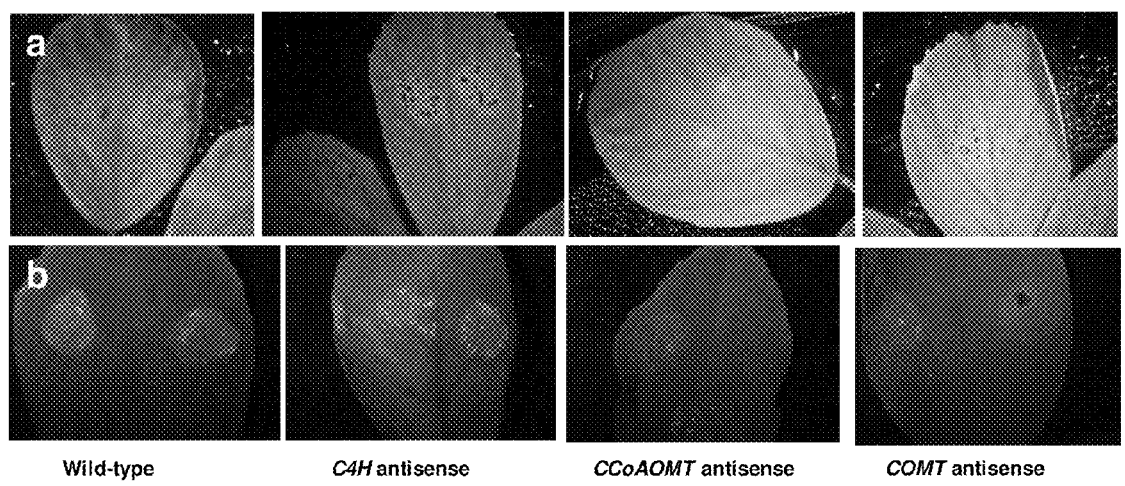
FIG. 11. Responses of wild-type and reduced lignin alfalfa lines to *Colletotrichum trifolii*. Pathogen assays were conducted as described in Example 4, using six-week old plants. Panels a and b are from two-independent experiments. GFP-tagged *C. trifolii* (panel b) and autofluorescence of the chloroplast were visualized using an epifluorescence-stereomicroscope.
Figure 12:
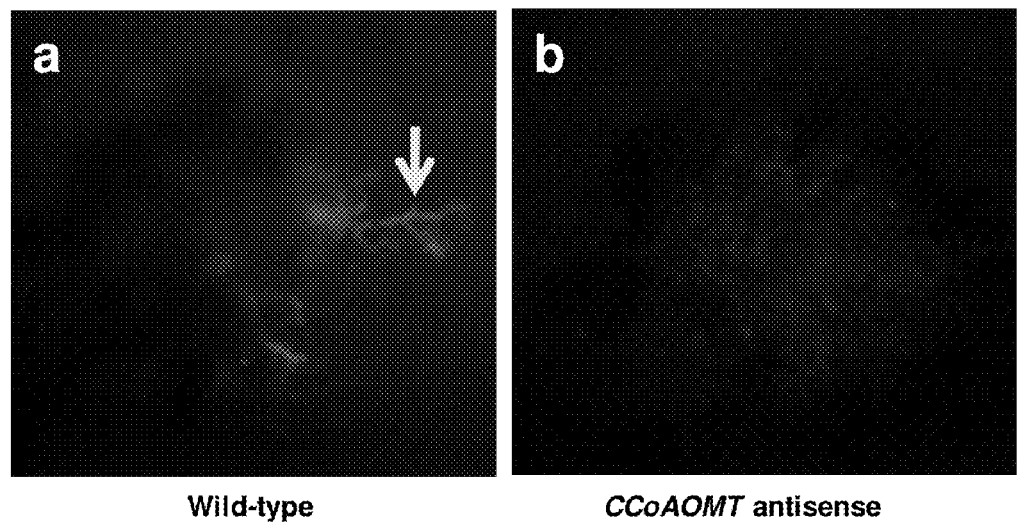
FIG. 12. Susceptibility of wild-type and reduced lignin alfalfa lines to *Colletotrichum trifolii*. The fungus proliferated to a greater extent, as visualized by the mycelial growth, on wild-type (a, arrow) compared to the lignin down-regulated CCoAOMT lines (b). Pathogen assays were conducted as described in Example 4 using six-week old plants. GFP-tagged *C. trifolii* was visualized using an epifluorescence-stereomicroscope.
Figure 13:
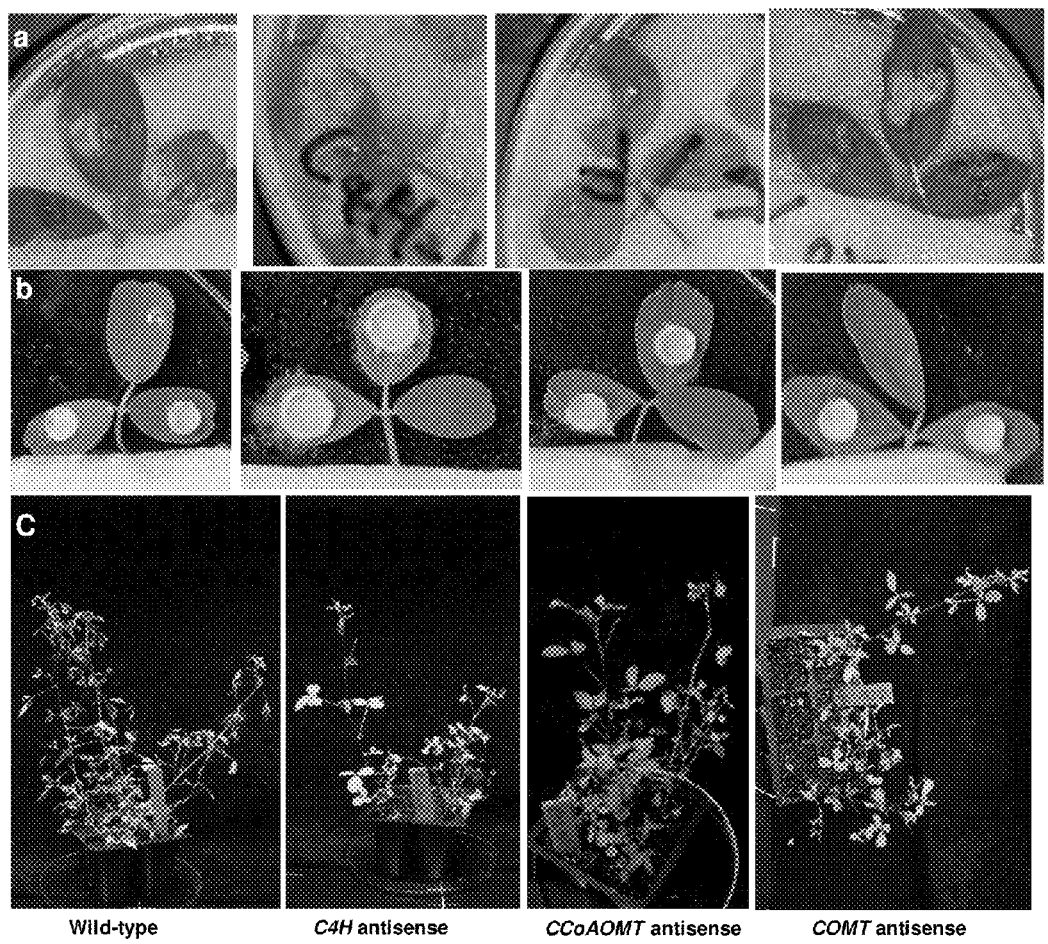
FIG. 13. Susceptibility of wild-type and lignin down-regulated alfalfa lines to various fungal pathogens. Disease phenotypes of wild-type (cv. Regen SY4D) and transgenic lines down-regulated for C4H, CCoAOMT or COMT challenged with *Phoma medicaginis* (panel a), *Sclerotinia sclerotiorum* (panel b), and *Phytophthora medicaginis* (panel c). Empty cells in panel c with no plants are the alfalfa cuttings that did not root. Pathogen assays were conducted as described in Example 4 using six-week old plants.

Several fungal pathogens including *Colletotrichum trifolii*, *Phoma medicaginis*, *Phytophthora medicaginis* and *Aphanomyces euteiches* cause devastating diseases on alfalfa and annual *Medicago* spp. worldwide, resulting in huge economic losses (e.g. Tivoli et al., 2006). To test if CCoAOMT down-regulated lines exhibit broad-spectrum tolerance/resistance, wild-type, C4H, CCoAOMT and COMT down-regulated lines were challenged in controlled experiments with several other fungal pathogens (Table 4; FIGS. 11-13). Ten days post-inoculation with *C. trifolii*, the leaves of wild-type and C4H down-regulated plants showed more severe disease symptoms when compared to the CCoAOMT and COMT down-regulated lines which showed lessened disease severity and supported less fungal growth when compared to the wild-type (Table 4; FIGS. 11-12), although CCoAOMT and COMT down-regulated lines did not show significant tolerance to all foliar and root pathogens tested (Table 4; FIG. 13). Of critical importance in view of previous theories relating to the role of lignin in plant disease, CCoAOMT and COMT down-regulated lines were not more susceptible than the wild-type plants to any of the pathogens tested (Table 4). Severity was scored 7-15 days post-inoculation; assessment of susceptibility was based on 1-5+ disease score scale, where 5+ was most susceptible. Thus, certain lignin down-regulated lines displayed reduced severity of disease (or delayed disease symptoms) caused by *P. omnivora*, a *Phytophthora* sp., and a *Colletotrichum* sp.

the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references cited in this application, including those listed below, are incorporated by reference to the extent that they supplement, explain, provide a background for, or teach methodology, techniques, and/or compositions employed herein. The discussion of the references herein is intended merely to summarize the assertions made by the authors and no admission is made that any reference constitutes prior art. Applicants reserve the right to challenge the accuracy and pertinence of the cited references.

U.S. Pat. No. 3,990,994; U.S. Pat. No. 4,461,648; U.S. Pat. No. 4,535,060; U.S. Pat. No. 4,600,590; U.S. Pat. No. 5,000,000; U.S. Pat. No. 5,037,663; U.S. Pat. No. 5,302,523; U.S. Pat. No. 5,322,783; U.S. Pat. No. 5,384,253; U.S. Pat. No. 5,451,514; U.S. Pat. No. 5,459,252; U.S. Pat. No. 5,464,765; U.S. Pat. No. 5,508,184; U.S. Pat. No. 5,538,877; U.S. Pat. No. 5,538,880; U.S. Pat. No. 5,545,818; U.S. Pat. No. 5,550,318; U.S. Pat. No. 5,563,055; U.S. Pat. No. 5,591,616; U.S. Pat. No. 5,610,042; U.S. Pat. No. 5,850,020; U.S. Pat. No. 5,922,928; U.S. Pat. No. 5,972,118; U.S. Pat. No. 6,072,103; U.S. Pat. No. 6,610,908; U.S. Pat. No. 6,841,721; U.S. Pat. No. 7,005,562.

U.S. Pat. Publ 20030005481; U.S. Pat. Publ 20040049802

Abdullah et al., *Biotechnology* 4:1087, 1986.
Bailey and Elkan, pp. 28-36 in: *Proceedings of the Second International Conference on Intelligent Systems for Molecular Biology*, AAAI Press, Menlo Park, Calif., 1994.
Bailey and Gribskov, *Bioinformatics* 14: 48-54, 1998.
Badger, pp. 17-21 in *Trends in new crops and new uses* J. Janick, A. Whipkey, Eds., ASHS Press, Alexandria, Va., 2002.
Bates, *Mol. Biotechnol.* 2(2):135-145, 1994.
Battraw and Hall, *Theor. App. Genet.* 82(2):161-168, 1991.

TABLE 4

Susceptibility of wild-type and lignin down-regulated alfalfa lines to various fungal pathogens.

| | Disease severity | | | |
|---|---|---|---|---|
| Pathogen | Wild-type | C4H down-regulated | CCoAOMT down-regulated | COMT down-regulated |
| *Phymatotrichopsis omnivora* | ++++ | +++++ | + | + |
| *Phoma medicaginis* | ++++ | ++++ | ++++ | ++++ |
| *Sclerotinia sclerotiorum* | ++++ | +++++ | ++++ | ++++ |
| *Phytophthora medicaginis* | +++ | ++++ | +++* | +++* |
| *Colletotrichum trifolii* | ++++ | +++++ | + | + |

*showed delayed disease symptoms

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from Baucher, et al., *Plant Mol. Biol.* 39:437-447, 1999.
Baucher et al., *Crit. Rev. Biochem Mol. Biol.*, 38:305-350, 2003.
Benedito et al., *Plant J* in press, 2008.
Bennett, and Wallsgrove, *New Phytol.* 127:617-633, 1994.
Bevan et al., *Nucleic Acids Research* 11 (2):369-385, 1983.
Bhattacharjee et al., *J. Plant Bioch. and Biotech.* 6, (2):69-73. 1997.

Bhattacharyya, and Ward., *Physiol. Mol. Plant. Pathol.* 27:2691-2694, 1985.
Bird, L. S. et al., *Phytopathology* 74:819, 1984.
Blancaflor et al., *Planta* 217(2):206-17, 2003.
Blount, J. et al., *Physiol. Mol. Plant. Pathol.* 41:333-349, 1992.
Bloss, H. E. and Wheeler, J. E. *Mycologia* 67:303-310, 1975.
Bouchez et al., *EMBO Journal* 8(13):4197-4204, 1989.
Boudet, et al., *New Phytol.* 129:203-236, 1995.
Bower et al., *Plant Journal* 2:409-416. 1992.
Buckley et al., *Eur. J. Pharmacol.* 396:141-149, 2000.
Buising and Benbow, *Mol. Gen. Genet.* 243(1):71-81. 1994.
Buxton and Russell, 1988. *Crop Sci* 28:553-558.
Callis et al., *Genes Dev.* 1:1183-1200, 1987.
Carver et al., *Physiol. Mol. Plant. Pathol.* 44:243-259, 1994.
Casa et al., *Proc. Natl. Acad. Sci. USA,* 90(23):11212-11216, 1993.
Casler, Crop Sci 27:931-934, 1987.
Chandler et al., *The Plant Cell* 1:1175-1183, 1989.
Chapman et al., *Plant Physiol.* 120:1157-1164, 1999.
Chapman et al., *Plant. Physiol* 116: 1163-1168, 1998.
Chapman, *Chem. Phys. Lipids,* 108:221-230, 2000.
Chen and Dixon, *Nat. Biotechnol.* 25:759-61, 2007.
Chen et al., *Plant J.* 48:113-124, 2006.
Cho and Cosgrove, *The Plant Cell* 14:3237-3253, 2002.
Christou et al., *Proc. Natl. Acad. Sci. USA,* 84:3962-3966, 1987.
Chu et al., *Scientia Sinica* 18:659-668, 1975.
Conkling et al., *Plant Physiol.* 93:1203-1211, 1990.
Dauwe, et al., *Plant J.* 52:263-285, 2007.
Davin and Lewis, *Rec Adv Phytochem.* 26:325-375, 1992.
Davison et al., *Appl. Biochem. Biotechnol.* 129-132: 427-435, 2006.
DE App. 3642, 829
De Block et al., *EMBO Journal* 6(9):2513-2518, 1987.
De Block et al., *Plant Physiol.,* 91:694-701, 1989.
De Petrocellis et al., *Chemistry and Physics of Lipids* 108: 191-209, 2000
Dellaporta et al., In: *Chromosome Structure and Function: Impact of New Concepts, 18th Stadler Genetics Symposium,* 11:263-282, 1988.
Devane et al., *Science* 258: 1946-1949, 1992
D'Halluin et al., *The Plant Cell* 4(12):1495-1505, 1992.
Dixon and Steele, *Trends Plant Sci.* 4:394-400, 1999.
Dixon, et al., *Rec Adv Phytochem.* 28:153-178, 1994.
Dixon, et al., *Gene* 179:61-71, 1996.
Di Marzo et al., *Nature* 372: 686-691, 1994
Do et al., *Planta* 226:1117-1129, 2007.
Downward, *BMJ,* 328(7450):1245-1248, 2004.
Dubois, et al., *Anal. Chem.* 28:250, 1956.
Duff and Murray, *Bioresource Tech.* 55:1-33, 1995.
Dwivedi, et al., *Plant Mol. Biol.* 26:61-71, 1994.
EP Patent Applic. 154,204
Ebert et al., *Proc. Natl. Acad. Sci. USA* 84:5745-5749, 1987
Ellis et al., *EMBO Journal* 6(11):3203-3208, 1987.
Fire et al., *Nature* 391: 806-11, 1998.
Fraley et al., *Bio/Technology* 3:629-635, 1985.
Franke et al., *Plant J.* 30:33-45 (2002).
Fromm et al., *Nature* 319:791-793, 1986.
Fukushima and Hatfield, *J. Agric. Food Chem.* 52:3713-3720, 2004.
Gallie et al., *The Plant Cell,* 1:301-311, 1989.
Gelvin et al., In: *Plant Molecular Biology Manual,* 1990.
Ghosh-Biswas et al., *J. Biotechnol.* 32(1):1-10, 1994.
Goering et al., *Forage Fiber Analysis,* Vol. 379. U.S. Government Printing Office, Washington, D.C. 1970.
Gong et al., *Adv. Biochem. Eng. Biotech.* 65: 207-241, 1999.
Grabber et al., *Crop Sci.* 32: 806-810, 1992.
Grabber, et al., *J. Agric. Food Chem.* 45:2530-2532, 1997.
Graham et al., *A Compendium of Alfalfa Diseases,* American Phytopathological Society, St. Paul, Minn., 1979.
Guo et al., *Plant Cell* 13:73-88, 2001a.
Guo et al., *Transgenic Res.* 10:457-464, 2001b.
Haemelinck et al., *Biomass and Bioenergy* 28:84, 2005.
Hagio et al., *Plant Cell Rep.* 10(5):260-264, 1991.
Hamilton et al., *Proc. Natl. Acad. Sci. USA* 93(18):9975-9979, 1996.
Hansen et al., *Chem. Phys. Lipids.* 108:135-150, 2000.
Harbome, J. B. *Pure Appl. Chem.* 49:1403-1421, 1977.
Haseloff et al., *Proc. Natl. Acad. Sci. USA* 94(6):2122-2127, 1997.
He et al., *Plant Cell Reports* 14 (2-3):192-196, 1994.
Hennebert, C. L. *Persoonia* 7:183-204, 1973.
Hensgens et al., *Plant Mol. Biol.* 22(6): 1101-1127, 1993.
Hiei et al., *Plant. Mol. Biol.* 35(1-2):205-218, 1997.
Hillard et al., *J. Neurochem.* 64:677-683, 1995.
Hinchee et al., *Bio/technol.* 6:915-922, 1988.
Hoffmann et al., *Plant Cell* 16:1446-1465, 2004.
Hou and Lin, *Plant Physiology* 111:166, 1996.
Hu et al., *Nat. Biotechnol.* 17:808-812, 1999.
Hudspeth and Grula, *Plant Mol. Biol.* 12:579-589, 1989.
Ikuta et al., *Bio/technol.* 8:241-242, 1990.
Ishida et al., *Nat. Biotechnol.* 14(6):745-750, 1996.
Jung and Vogel, *J. Anim. Sci.* 62:1703-1712, 1986
Kaeppler et al., *Plant Cell Reports* 9: 415-418, 1990.
Kaeppler et al., *Theor. Appl. Genet.* 84(5-6):560-566, 1992.
Katz et al., *J. Gen. Microbiol.* 129:2703-2714, 1983.
Keller et al., *The Plant Cell* 11:223-235, 1999.
Khanolkar et al., *Chemistry and Physics of Lipid* 108:37-52, 2000.
Klee et al., *Bio-Technology* 3(7):637-642, 1985.
Knittel et al., *Plant Cell Reports* 14(2-3):81-86, 1994.
Krogh et al., *J. Mol. Biol.* 305:567-580, 2001.
Kurata et al., *Development* 132:5387-5398, 2005.
Lambert and Di Marzo, *Current Med. Chem.* 6:663-674, 1999.
Lambert et al., *Current Med. Chem.* 9:739-755, 2002.
Lapierre et al., *J. Wood Chem. Technol.* 5:277-292 1985.
Lapierre et al., *Res. Chem. Intermed.* 21: 397-412, 1995.
Lawton et al., *Plant Mol. Biol.* 9:315-324, 1987.
Lazzeri, *Methods Mol. Biol.* 49:95-106, 1995.
Lee et al., *Adv. Biochem. Engng. Biotech.* 65: 93-115, 1999
Lee et al., *Korean J. Genet.* 11(2):65-72, 1989.
Lehner et al., *Brief Funct Genomic Proteomic* 3(1):68-83, 2004.
Lewis, *Current Opinion in Plant Biology* 2:153-162, 1999.
Li et al., *Plant J.* 54:569-581, 2008.
Lorang et al., *Appl. Env. Microbiol.* 67:1987-1994, 2001.
Lorz et al., *Mol. Gen. Genet.* 199:178-182, 1985.
Lozovaya et al., *Crop. Sci.* 44:819-826, 2004.
Lyda, *Ann. Rev. Phytopathol.* 16:193-209, 1978.
Lyda et al., *Plant Dis. Rep.* 51:331-333, 1967.
Marcotte et al., *Nature* 335:454, 1988.
McCabe and Martinell, *Bio-Technology* 11(5):596-598, 1993.
McCormac et al., *Euphytica.* 99: 17-25, 1998.
McLaughlin, S. B. and M. E. Walsh. *Biomass Bioenergy* 14:317-324, 1998.
Mes-Hartree, et al. *Appl. Microbiol. Biotechnol.* 29:462-468, 1988.
Meyermans et al., *J Biol Chem.* 24:36899-36909, 2000.
Morjanoff and Gray, *Biotechnol. Bioeng.* 29:733-741, 1987.
Murakami et al., *Mol. Gen. Genet.* 205:42-50, 1986.
Murashige and Skoog, *Physiol. Plant.* 15:473-497, 1962.

Nagatani et al., *Biotech. Tech.* 11(7):471-473, 1997.
Nicholson and Hammerschmidt, *Annu Rev Phytopathol.* 30:369-389, 1992.
Odell et al., *Nature* 313:810-812, 1985.
Ogawa et al., *Sci. Rep.* 13:42-48, 1973.
Olsson and Hahn-Hagerdal, *Enzyme and Microb. Technol.* 18:312-331, 1996.
Omirulleh et al., *Plant Mol. Biol.* 21(3):415-428, 1993.
Ow et al., *Science* 234:856-859, 1986.
Pakusch et al., *Arch Biochem Biophys.* 271:488-494, 1989.
Pammel, L. H. *Texas Agric. Exp. Sta. Ann. Rpt.* 1:3-18, 1888.
Paria and Dey, *Chem. Phys. Lipids* 108:211-220, 2000.
Parvathi et al., *Plant J.* 25:193-202, 2001.
PCT Publication WO 92/17598; PCT Publication WO 94/09699; PCT Publication WO 95/06128; PCT Publication WO 97/41228; PCT Publication WO 97/4103; PCT Publication WO 01/53502; PCT Publication WO 01/73090; PCT Publication WO 06/12594.
Percy, R. G. *Plant Dis.* 67:981-983, 1983.
Pertwee et al., *Eur. J. Pharmacol.* 272:73-78, 1995.
Pertwee, *Prog. Neurobiol.* 63:569-611, 2001.
Pedersen et al., *Crop Sci.* 45: 812-819, 2005.
Pilat, *Nature Biotechnology* 20:607, 2002.
Potrykus et al., *Mol. Gen. Genet.* 199:183-188, 1985.
Prasher et al., *Biochem. Biophys. Res. Commun.* 126(3): 1259-1268, 1985.
Reddy et al., *Proc. Nat. Acad. Sci. U.S.A.* 102:16573-16578, 2005.
Reggio P H, *Tocris Reviews* 10:1-5, 1999.
Reichel et al., *Proc. Natl. Acad. Sci. USA* 93: 5888-5893. 1996.
Reynolds, *Nat. Biotechnol.* 22:326-330, 2004.
Rhodes et al., *Methods Mol. Biol.* 55:121-131, 1995.
Richards et al., *Plant Cell Rep.* 20:48-54, 2001.
Ritala et al., *Plant Mol. Biol.* 24(2):317-325, 1994.
Rogers et al., *Methods Enzymol.* 153:253-277, 1987.
Sambrook et al., In: *Molecular Cloning-A Laboratory Manual* (second edition), Cold Spring Harbour Laboratory Press, 1989.
Sarker et al., *FEBS Lett.* 472:39-44, 2000.
Schmid and Berdyshev, *Prostag. Leukotr. Essent. Fatty Acids* 66:363-376, 2002.
Schmid et al., *Chem. Phys. Lipids* 121:111-134, 2002.
Schmid et al., *Prog. Lipid Res.* 29:1-43, 1990.
Sederoff, et al, *Current Opinion in Plant Biology* 2:145-152, 1999.
Shadle, et al., "Effects Of Down-Regulation Of HCT On Lignin In Alfalfa." Phytochemical Society of North America Annual Meeting, Jul. 8-12, 2006, Oxford, Miss.
Sheen et al., *Plant Journal* 8(5):777-784, 1995.
Shrestha et al., *J. Biol. Chem.* 278: 34990-34997, 2003.
Shrestha et al., *Plant Physiol.* 130:391-401, 2002.
Singsit et al., *Transgenic Res.* 6(2):169-176, 1997.
Somleva et al. *Crop Science* 42:2080-2087, 2002.
Stalker et al., *Science* 242:419-422, 1988.
Sticklen, *Curr. Op. Biotechnol.* 17:315-319, 2006.
Straus, *Proc Natl Acad Sci USA* 97: 9363-9364, 2000.
Streets and Bloss, *Am. Phytopathol. Soc. Monogr.* 8:1-38, 1973.
Sullivan et al., *Mol. Gen. Genet.* 215(3):431-440, 1989.
Sun and Cheng, *Bioresource Technol.* 83:1-11, 2002.
Sutcliffe, *Proc. Natl. Acad. Sci. USA* 75:3737-3741, 1978.
Tabe, et al., *Genetica* 90:181-200, 1993.
Tahara, 2007. *Biosci Biotechnol Biochem.* 71:1387-1404, 2007.
Thillet et al., *J. Biol. Chem.* 263:12500-12508, 1988.
Thomas et al., *Plant Sci.* 69:189-198, 1990.
Thompson et al., *Euphytica* 85(1-3):75-80, 1995.
Thompson et al., *The EMBO Journal* 6:2519-2523, 1987.
Tian et al., *Plant Cell Rep.* 16:267-271, 1997.
Tingay et al., *The Plant Journal* 11:1369-1376, 1997.
Tivoli et al., *Ann. Bot.* 98:1117-1128, 2006.
Tomes et al., *Plant. Mol. Biol.* 14:261-268, 1990.
Torbet et al., *Crop Science* 38(1):226-231, 1998.
Torbet et al., *Plant Cell Reports* 14(10):635-640, 1995.
Toriyama et al., *Theor Appl. Genet.* 73:16, 1986.
Triparthy et al., *Plant Physiol* 131: 1781-1791, 2003a.
Tripathy et al., *In Advanced Research on Plant Lipids,* 2002: 315-318, N. Murata et al., (eds), 2003b.
Tripathy et al., *Plant Physiol.* 121:1299-1308, 1999.
Tsukada et al., *Plant Cell Physiol.* 30(4)599-604, 1989.
Tusnády and Simon, *J. Mol. Biol.* 283, 489-506, 1998.
Tusnády and Simon, *Bioinformatics* 17, 849-850, 2001.
Twell et al., *Plant Physiol.* 91:1270-1274, 1989.
Uchimiya et al., *Mol. Gen. Genet.* 204:204, 1986.
Van der Stelt et al., *J. Neurosci* 21:765-8771, 2001.
Van Eck et al., *Plant Cell Reports* 14(5):299-304, 1995.
Vance et al., *Ann. Rev. Phytopathol.* 18:259-288, 1980.
Vasil et al., *Plant Physiol.* 91:1575-1579, 1989.
Vijaybhaskar et al., *J. Biosci.* 33: 185-193, 2008.
Vogel et al., *Crop Sci.* 39:276-279, 1999.
Vogel and Jung, ORNL/Sub/90-90OR21954/1, 2000.
Walker et al., *Proc. Natl. Acad. Sci. USA* 84:6624-6628, 1987.
Wang et al., *Molecular and Cellular Biology* 12(8):3399-3406, 1992.
Whetten and Sederoff, *Forest Ecology and Management* 43:301-316, 1991.
Wilson and Nicoll, *Science* 296:678-682, 2002.
Wróbel-Kwiatkowska et al., *J. Biotechnol.* 128:919-934, 2007.
Wyman, *Annu. Rev. Energy Environ.* 24:189-226, 1999.
Yamada et al., *Plant Cell Rep.* 4:85, 1986.
Yamamizo et al., *Plant Physiol.* 140:681-692, 2006.
Yang and Russell, *Proc. Natl. Acad. Sci. USA* 87:4144-4148, 1990.
Ye et al., *Plant Cell* 6:1427-1439, 1994.
Ye et al., *Phytochemistry* 57:1177-1185, 2001.
Zhang et al., *Science* 267:240-243, 1995.
Zheng and Edwards, *J. Gen. Virol.* 71:1865-1868, 1990.
Zhong et al., *Plant Physiol.* 124:563-578, 2000.
Zhou et al., *Plant Cell Reports,* 12(11):612-616, 1993.
Zukowsky et al., *Proc. Natl. Acad. Sci. USA* 80:1101-1105, 1983.

What is claimed is:

1. A transgenic alfalfa plant comprising a first selected DNA that down-regulates the activity of caffeic acid 3-O-methyltransferase (COMT) or caffeoyl CoA 3-O-methyltransferase (CCoAOMT) in the plant through inhibition of transcription or translation of a COMT or CCoAOMT gene, wherein COMT or CCoAOMT activity is down-regulated (a) in the roots of the plant, (b) in response to infection by a root-infecting fungal plant pathogen, or (c) during infection by *Phymatotrichopsis omnivore* or *Colletotrichum* spp., wherein the first selected DNA is expressed primarily in the roots of the plant, and wherein the plant exhibits resistance to *Phymatotrichopsis omnivore* or *Colletotrichum* spp. as a result of the presence of said first selected DNA.

2. The plant of claim 1, wherein the *Colletotrichum* spp, is *C. trifolii*.

3. The plant of claim 1, wherein COMT is down-regulated.

4. The plant of claim 1, wherein CCoAOMT is down-regulated.

5. The plant of claim 4, further comprising a second selected DNA that down-regulates activity of COMT.

6. The plant of claim 1, wherein the plant exhibits increased resistance to *Phymatotrichopsis* Root Rot or to a disease caused by *Colletotrichum* spp., relative to the corresponding plant not comprising the first selected DNA.

7. The plant of claim 1, wherein the first selected DNA encodes an antisense or an RNAi transcript.

8. The plant of claim 1, wherein the first selected DNA is not expressed in the stem of the plant.

9. The plant of claim 1, wherein the first selected DNA is operably linked to a root-preferred promoter.

10. The plant of claim 9, wherein the root-preferred promoter is an RB7, RPE15, RPE14, RPE19, RPE29, RPE60, RPE2, RPE39, RPE61, SHR, ELG3, EXP7, EXP18 or At1g73160 promoter.

11. The plant of claim 1, wherein the first selected DNA is expressed primarily in response to infection by a root-infecting fungal plant pathogen.

12. The plant of claim 11, wherein the first selected DNA is operably linked to a fungal pathogen-inducible promoter.

13. The plant of claim 12, wherein the fungal pathogen-inducible promoter is an hsr203J, PVS3, N116, or STS8 stilbene synthase promoter.

14. The plant of claim 1, wherein the plant accumulates 7,4-dihydroxyflavone when contacted with *Phymatotrichopsis omnivora*.

15. A method of rendering an alfalfa plant that is otherwise susceptible to *Phymatotrichopsis* Root Rot, or to a disease caused by *Colletotrichum* sp., more resistant to such a disease, the method comprising:
    expressing in an alfalfa plant a first selected DNA that down-regulates the activity of caffeic acid 3-O-methyltransferase (COMT) or caffeoyl CoA 3-O-methyltransferase (CCoAOMT) in the modified plant through inhibition of transcription or translation of a COMT or CCoAOMT gene, wherein COMT or CCoAOMT activity is down-regulated (a) primarily in the roots of the modified plant, (b) primarily in response to infection by a root-infecting fungal plant pathogen; or (c) during infection by *Phymatotrichopsis omnivora*, or *Colletotrichum* spp.

16. The method of claim 15, wherein the first selected DNA is transformed into an alfalfa plant, and progeny of the alfalfa plant are grown such that a modified plant is produced that is homozygous for the first selected DNA.

17. The method of claim 15, wherein the first selected DNA is in a nucleic acid vector that is suitable for use in *Agrobacterium* transformation of the plant.

18. The method of claim 15, wherein the first selected DNA is in a nucleic acid vector that is suitable for use in transformation of the plant by microparticle bombardment.

19. A nucleic acid vector comprising a first selected DNA that down-regulates activity of caffeic acid 3-O-methyltransferase (COMT) or caffeoyl CoA 3-O-methyltransferase (CCoAOMT) in the plant through inhibition of transcription or translation of a COMT or CCoAOMT gene, such that, when the vector is transformed into an alfalfa plant, the first selected DNA is expressed (a) primarily in the roots of the resulting transgenic plant, (b) primarily in response to infection of the resulting transgenic plant by a root-infecting fungal plant pathogen; or (c) during infection by *Phymatotrichopsis omnivora*, or *Colletotrichum* spp.

20. The vector of claim 19, wherein the vector is suitable for use in *Agrobacterium* transformation of the plant.

21. The vector of claim 19, wherein the vector is suitable for use in transformation of the plant by microparticle bombardment.

22. A method of growing an alfalfa plant that is naturally susceptible to *Phymatotrichopsis* Root Rot or to a disease caused by *Colletotrichum* sp., in soil or a field or crop that comprises *Phymatotrichopsis omnivora* or *Colletotrichum* sp., the method comprising:

expressing a first selected DNA in the alfalfa plant that down-regulates the activity of caffeic acid 3-O-methyltransferase (COMT) or caffeoyl CoA 3-O-methyltransferase (CCoAOMT) in the alfalfa plant through inhibition of transcription or translation of a COMT or CCoAOMT gene, and growing the alfalfa plant expressing the first selected DNA in the soil or the field.

23. The method of claim 22, wherein, before expressing the first selected DNA, the first selected DNA is transformed into an alfalfa plant and progeny of the plant are grown such that a modified alfalfa plant is produced that is homozygous for the first selected DNA.

24. The method of claim 22, wherein the first selected DNA is constitutively expressed in the modified alfalfa plant.

25. The method of claim 22, wherein the first selected DNA is expressed primarily in the roots of the plant.

26. The method of claim 22, wherein the first selected DNA is expressed primarily in response to infection by a root-infecting fungal plant pathogen.

27. A method of treating an alfalfa plant that is susceptible to a fungal plant pathogen, the method comprising providing 7,4-dihydroxyflavone to the plant.

28. The method of claim 27, wherein the fungal plant pathogen is *Phymatotrichopsis omnivora* or a *Colletotrichum* sp.

29. The method of claim 27, wherein the fungal plant pathogen is a root-infecting fungal plant pathogen, or a foliar-infecting plant pathogen.

* * * * *